(12) United States Patent
Hauel et al.

(10) Patent No.: US 6,710,055 B2
(45) Date of Patent: *Mar. 23, 2004

(54) DISUBSTITUTED BICYCLIC HETEROCYCLES, THE PREPARATION THEREOF, AND THEIR USE AS PHARMACEUTICAL COMPOSITIONS

(75) Inventors: Norbert Hauel, Schemmerhofen (DE); Henning Priepke, Warthausen (DE); Uwe Ries, Biberach (DE); Jean Marie Stassen, Warthausen (DE); Wolfgang Wienen, Biberach (DE)

(73) Assignee: Boehringer Ingelheim Pharma GmbH & Co., KG, Ingelheim (DE)

( * ) Notice: Subject to any disclaimer, the term of this patent is extended or adjusted under 35 U.S.C. 154(b) by 9 days.

This patent is subject to a terminal disclaimer.

(21) Appl. No.: 10/192,041

(22) Filed: Jul. 10, 2002

(65) Prior Publication Data

US 2003/0004181 A1 Jan. 2, 2003

Related U.S. Application Data

(60) Continuation of application No. 09/544,931, filed on Apr. 6, 2000, now Pat. No. 6,469,039, which is a division of application No. 09/025,690, filed on Feb. 18, 1998, now Pat. No. 6,087,380.

(60) Provisional application No. 60/044,421, filed on Apr. 29, 1997.

(30) Foreign Application Priority Data

Feb. 18, 1997 (DE) .......................... 197 06 229
Nov. 24, 1997 (DE) .......................... 197 51 939

(51) Int. Cl.$^7$ .................... A61K 31/437; C07D 471/04
(52) U.S. Cl. ...................................... 514/303; 546/118
(58) Field of Search ........................... 546/118; 514/303

(56) References Cited

U.S. PATENT DOCUMENTS 6,414,008 B1 * 7/2002 Hauel et al. ................ 514/394

* cited by examiner

Primary Examiner—Patricia L. Morris
(74) Attorney, Agent, or Firm—Robert P. Raymond; Timothy X. Witkowski; Anthony P. Bottino

(57) ABSTRACT

Disubstituted bicyclic heterocycles of general formula I $$R_a-A-Het-B-Ar-E \qquad (I).$$

Compounds of general formula I, wherein E is an $R_b$NH—C(=NH)— group, have valuable pharmacological properties, particularly a thrombin-inhibiting effect and the effect of prolonging thrombin time, and those wherein E is a cyano group, are valuable intermediates for preparing the other compounds of general formula I.

21 Claims, No Drawings

DISUBSTITUTED BICYCLIC HETEROCYCLES, THE PREPARATION THEREOF, AND THEIR USE AS PHARMACEUTICAL COMPOSITIONS

RELATED APPLICATIONS

This is a continuation of U.S. Ser. No. 09/544,931, filed Apr. 6, 2000, now U.S. Pat. No. 6,469.039, issued Oct. 22, 2002, which is a division of U.S. Ser. No. 09/025,690, filed Feb. 18, 1998, now U.S. Pat. No. 6,087,380, issue Jul. 11, 2000, which claimed benefit of prior filed and copending U.S. provisional application Ser. No. 60/044,421, filed Apr. 29, 1997.

DESCRIPTION OF THE INVENTION

The present invention relates to new disubstituted bicyclic heterocycles of general formula $$R_a\text{—}A\text{—}Het\text{—}B\text{—}Ar\text{—}E \qquad (I)$$

the tautomers, stereoisomers and mixtures thereof and the salts thereof, particularly the physiologically acceptable salts thereof with organic or inorganic acids or bases which have valuable properties.

The compounds of general formula I above wherein E denotes a cyano group are valuable intermediates for preparing the other compounds of general formula I, and the compounds of general formula I above wherein E denotes an $R_b$NH—C(=NH)— group, and the tautomers and stereoisomers thereof have useful pharmacological properties, particularly a thrombin-inhibiting activity and the effect of extending thrombin time.

The present application thus relates to the new compounds of general formula I above and the preparation thereof, pharmaceutical compositions containing the pharmacologically active compounds and the use thereof.

In the above general formula:

A denotes a carbonyl or sulfonyl group linked to the benzo, pyrido, pyrimido, pyrazino, pyridazino or thieno moiety of the group Het, whilst moreover the abovementioned moieties may not contain an $R_1$ group, B denotes an ethylene group, wherein a methylene group, linked either to the group Het or Ar, may be replaced by an oxygen or sulfur atom or by a sulfinyl, sulfonyl, carbonyl or —$NR_1$ group, wherein $R_1$ denotes a hydrogen atom or a $C_{1-6}$-alkyl group, E denotes a cyano or $R_b$NH—C(=NH)— group wherein $R_b$ denotes a hydrogen atom, a hydroxy group, a $C_{1-3}$-alkyl group or a group which may be cleaved in vivo, Ar denotes a phenylene or naphthylene group optionally substituted by a fluorine, chlorine or bromine atom or by a trifluoromethyl, $C_{1-3}$-alkyl, or $C_{1-3}$-alkoxy group, a thienylene, thiazolylene, pyridinylene, pyrimidinylene, pyrazinylene or pyridazinylene group optionally substituted in the carbon skeleton by a $C_{1-3}$-alkyl group, Het denotes a bicyclic heterocycle of formula

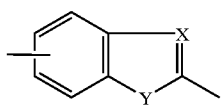

wherein
  X is a nitrogen atom and
  Y is an oxygen or sulfur atom or a nitrogen atom optionally substituted by a $C_{1-6}$-alkyl or $C_{3-7}$-cycloalkyl group, whilst additionally one or two non-angular methyne groups in the phenyl moiety of the abovementioned bicyclic heterocycle may each be replaced by a nitrogen atom, or X denotes a methyne group optionally substituted by the group $R_1$, wherein $R_1$ is as hereinbefore defined, and Y denotes a nitrogen atom optionally substituted by a $C_{1-6}$-alkyl or $C_{3-7}$-cycloalkyl group, or Het denotes a group of the formula

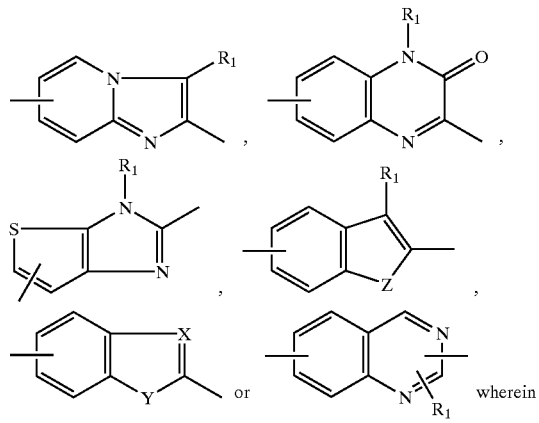

wherein $R_1$ is as hereinbefore defined,

Z denotes an oxygen or sulfur atom, one of the groups D or G denotes a nitrogen atom and the other group D or G denotes a methyne group, and $R_a$ denotes a $C_{1-6}$-alkyl group, a $C_{3-7}$-cycloalkyl group optionally substituted by a $C_{1-3}$-alkyl group, wherein the $C_{1-3}$-alkyl group may additionally be substituted by a carboxyl group or by a group which may be converted in vivo into a carboxy group, or an $R_2NR_3$— group wherein $R_2$ denotes a $C_{1-4}$-alkyl group, which may be substituted by a carboxy, $C_{1-6}$-alkyloxycarbonyl, benzyloxycarbonyl, $C_{1-3}$-alkylsulfonylaminocarbonyl, phenylsulfonylaminocarbonyl, trifluorosulfonylamino, trifluorosulfonylaminocarbonyl or 1H-tetrazolyl group, a $C_{2-4}$-alkyl group substituted by a hydroxy, phenyl-$C_{1-3}$-alkoxy, carboxy-$C_{1-3}$-alkylamino, $C_{1-3}$-alkoxycarbonyl-$C_{1-3}$-alkylamino, N—($C_{1-3}$-alkyl)-carboxy-$C_{1-3}$-alkylamino or N—($C_{1-3}$-alkyl)-$C_{1-3}$-alkoxycarbonyl-$C_{1-3}$-alkylamino group, whilst in the abovementioned groups the carbon atom in the a-position relative to the adjacent nitrogen atom may not be substituted, or a piperidinyl group optionally substituted by a $C_{1-3}$-alkyl group and $R_3$ denotes a hydrogen atom, a $C_{1-6}$-alkyl group, a $C_{3-7}$-cycloalkyl group optionally substituted by a $C_{1-3}$-alkyl group, a $C_{3-6}$-alkenyl or alkynyl group, wherein the unsaturated part may not be linked directly to the nitrogen atom of the $R_2NR_3$-group, a phenyl group optionally substituted by a fluorine, chlorine or bromine atom or by a $C_{1-3}$-alkyl or $C_{1-3}$-alkoxy group, a benzyl, oxazolyl, isoxazolyl, thiazolyl, isothiazolyl, pyrazolyl, pyridinyl, pyrimidinyl, pyrazinyl, pyridazinyl, pyrrolyl, thienyl or imidazolyl group or $R_2$ and $R_3$ together with the nitrogen atom between them denote a 5- to 7-membered cycloalkyleneimino group, optionally substituted by a carboxymethyl or $C_{1-4}$-alkoxycarbonyl group, onto which a phenyl ring may additionally be fused.

The compounds of the above general formula I which contain a group capable of being cleaved in vivo are thus prodrugs and compounds of general formula I which contain two groups capable of being cleaved in vivo are so-called double prodrugs.

The phrase "a group which may be converted in vivo into a carboxy group" denotes, for example, a hydroxymethyl group, a carboxy group esterified with an alcohol, in which the alcoholic moiety is preferably a $C_{1-6}$-alkanol, a phenyl-$C_{1-3}$-alkanol, a $C_{3-9}$-cycloalkanol, wherein a $C_{5-8}$-cycloalkanol may additionally be substituted by one or two $C_{1-3}$-alkyl groups, a $C_{5-8}$-cycloalkanol, in which a methylene group in the 3- or 4-position is replaced by an oxygen atom or by an imino group optionally substituted by a $C_{1-3}$-alkyl, phenyl-$C_{1-3}$-alkyl, phenyl-$C_{1-3}$-alkoxycarbonyl or $C_{2-6}$-alkanoyl group, and the cycloalkanol moiety may additionally be substituted by one or two $C_{1-3}$-alkyl groups, a $C_{4-7}$-cycloalkenol, a $C_{3-5}$-alkenol, a phenyl-$C_{3-5}$-alkenol, a $C_{3-5}$-alkynol or phenyl-$C_{3-5}$-alkynol, with the proviso that no bond to the oxygen atom emanates from a carbon atom which carries a double or triple bond, a $C_{3-8}$-cycloalkyl-$C_{1-3}$-alkanol, a bicycloalkanol having a total of 8 to 10 carbon atoms, which may additionally be substituted in the bicycloalkyl moiety by one or two $C_{1-3}$-alkyl groups, a 1,3-dihydro-3-oxo-1-isobenzofuranol or an alcohol of formula

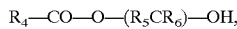

$$R_4\text{—CO—O—}(R_5CR_6)\text{—OH},$$

wherein:

$R_4$ denotes a $C_{1-8}$-alkyl, $C_{5-7}$-cycloalkyl, phenyl or phenyl-$C_{1-3}$-alkyl group;

$R_5$ denotes a hydrogen atom, a $C_{1-3}$-alkyl, $C_{5-7}$-cycloalkyl, or phenyl group; and $R_6$ denotes a hydrogen atom or a $C_{1-3}$-alkyl group, or the phrase "a group which may be cleaved in vivo from an imino or amino group" denotes for example a hydroxy group, an acyl group such as a benzoyl or pyridinoyl group or a $C_{1-16}$-alkanoyl group such as the formyl, acetyl, propionyl, butanoyl, pentanoyl or hexanoyl group, an allyloxycarbonyl group, a $C_{1-16}$-alkoxycarbonyl group such as the methoxycarbonyl, ethoxycarbonyl, propoxycarbonyl, isopropoxycarbonyl, butoxycarbonyl, tert-butoxycarbonyl, pentoxycarbonyl, hexoxycarbonyl, octyloxycarbonyl, nonyloxycarbonyl, decyloxycarbonyl, undecyloxycarbonyl, dodecyloxycarbonyl or hexadecyloxycarbonyl group, a phenyl-$C_{1-6}$-alkoxycarbonyl group such as the benzyloxycarbonyl, phenylethoxycarbonyl or phenylpropoxycarbonyl group, a $C_{1-3}$-alkylsulfonyl-$C_{2-4}$-alkoxycarbonyl, $C_{1-3}$-alkoxy-$C_{2-4}$-alkoxy-$C_{2-4}$-alkoxycarbonyl or $R_4CO\text{—O—}(R_5CR_6)\text{—O—CO—}$ group, wherein $R_4$ to $R_6$ are as hereinbefore defined.

Examples of preferred prodrug groups for a carboxy group include a $C_{1-6}$-alkoxycarbonyl group such as the methoxycarbonyl, ethoxycarbonyl, n-propyloxycarbonyl, isopropyloxycarbonyl, n-butyloxycarbonyl, n-pentyloxycarbonyl, n-hexyloxycarbonyl, or cyclohexyloxycarbonyl group or phenyl-$C_{1-3}$-alkoxycarbonyl group such as the benzyloxycarbonyl group and for an imino or amino group a $C_{1-9}$-alkoxycarbonyl group such as the methoxycarbonyl, ethoxycarbonyl, n-propyloxycarbonyl, isopropyloxycarbonyl, n-butyloxycarbonyl, n-pentyloxy-carbonyl, n-hexyloxycarbonyl, cyclohexyloxycarbonyl, n-heptyloxycarbonyl, n-octyloxycarbonyl or n-nonyloxycarbonyl group, a phenyl-$C_{1-3}$-alkoxycarbonyl group such as the benzyloxycarbonyl group, a phenylcarbonyl group optionally substituted by a $C_{1-3}$-alkyl group such as the benzoyl or 4-ethylbenzoyl group, a pyridinoyl group such as the nicotinoyl group, a $C_{1-3}$-alkylsulfonyl-n-$C_{2-3}$-alkoxycarbonyl or $C_{1-3}$-alkoxy-$C_{2-3}$-alkoxy-$C_{2-4}$-alkoxycarbonyl group such as the 2-methylsulfonylethoxycarbonyl or 2-(2-ethoxy) ethoxycarbonyl group.

Moreover, the saturated alkyl and alkoxy moieties containing more than 2 carbon atoms as well as alkanoyl and unsaturated alkyl moieties containing more than 3 carbon atoms as mentioned in the foregoing definitions also include the branched isomers thereof such as for example the isopropyl, tert-butyl and isobutyl group, etc.

Preferred compounds of the above general formula I, however, are those wherein:

A denotes a carbonyl or sulfonyl group linked to the benzo, pyrido, pyrimido, pyrazino, pyridazino or thieno moiety of the group Het, whilst moreover the abovementioned moieties may not contain an $R_1$ group, B denotes an ethylene group, in which a methylene group, linked either to the group Het or Ar, may be replaced by an oxygen or sulfur atom or by a sulfinyl, sulfonyl, carbonyl or —$NR_1$— group, wherein $R_1$ denotes a hydrogen atom or a $C_{1-5}$-alkyl group, E denotes an $R_b$NH—C(=NH)— group wherein $R_b$ denotes a hydrogen atom, a hydroxy group, a $C_{1-3}$-alkyl group or a group which may be cleaved in vivo, Ar denotes a phenylene group optionally substituted by a fluorine, chlorine or bromine atom or by a trifluoromethyl, $C_{1-3}$-alkyl or $C_{1-3}$-alkoxy group, a thienylene, thiazolylene, pyridinylene, pyrimidinylene, pyrazinylene or pyridazinylene group optionally substituted in the carbon skeleton by a $C_{1-3}$-alkyl group, Het denotes a bicyclic heterocycle of formula

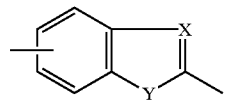

wherein

X is a nitrogen atom and

Y is an oxygen or sulfur atom or a nitrogen atom optionally substituted by a $C_{1-6}$-alkyl or $C_{3-7}$-cycloalkyl group, whilst additionally one or two non-angular methyne groups in the phenyl moiety of the abovementioned bicyclic heterocycle may each be replaced by a nitrogen atom, or X denotes a methyne group optionally substituted by the group $R_1$, wherein $R_1$ is as hereinbefore defined, and Y denotes a nitrogen atom optionally substituted by a $C_{1-6}$-alkyl or $C_{3-7}$-cycloalkyl group, or Het denotes a group of the formulae:

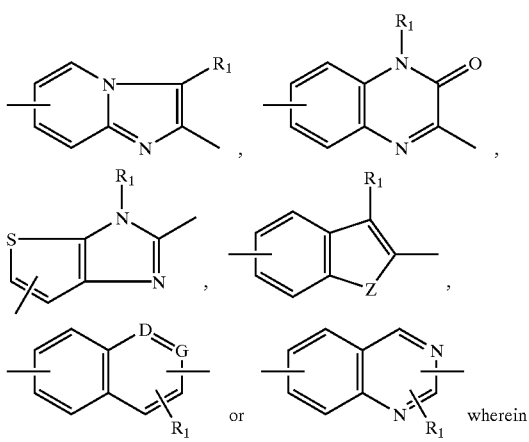

R₁ is as hereinbefore defined,

Z denotes an oxygen or sulfur atom, one of the groups D or G denotes a nitrogen atom and the other group D or G denotes a methyne group, and $R_a$ denotes a $C_{1-6}$-alkyl group, a $C_{3-7}$-cycloalkyl group optionally substituted by a $C_{1-3}$-alkyl group, wherein the $C_{1-3}$-alkyl group may additionally be substituted by a carboxyl group or by a group which may be converted in vivo into a carboxy group, or a $R_2NR_3$— group wherein $R_2$ denotes a $C_{1-4}$-alkyl group, which may be substituted by a carboxy, $C_{1-6}$-alkyloxycarbonyl, benzyloxycarbonyl, $C_{1-3}$-alkylsulfonylaminocarbonyl, phenylsulfonylaminocarbonyl, trifluorosulfonylamino, trifluorosulfonylaminocarbonyl or 1H-tetrazolyl group, a $C_{2-4}$-alkyl group substituted by a hydroxy, phenyl-$C_{1-3}$-alkoxy, carboxy-$C_{1-3}$-alkylamino, $C_{1-3}$-alkoxycarbonyl-$C_{1-3}$-alkylamino, N—($C_{1-3}$-alkyl)-carboxy-$C_{1-3}$-alkylamino or N—($C_{1-3}$-alkyl)-$C_{1-3}$-alkoxycarbonyl-$C_{1-3}$-alkylamino group, whilst in the abovementioned groups the carbon atom in the α-position relative to the adjacent nitrogen atom may not be substituted, or a piperidinyl group optionally substituted by a $C_{1-3}$-alkyl group and $R_3$ denotes a hydrogen atom, a $C_{1-6}$-alkyl group, a $C_{3-7}$-cycloalkyl group optionally substituted by a $C_{1-3}$-alkyl group, a $C_{3-6}$-alkenyl or alkynyl group, wherein the unsaturated part may not be linked directly to the nitrogen atom of the $R_2NR_3$— group, a phenyl group optionally substituted by a fluorine, chlorine or bromine atom or by a $C_{1-3}$-alkyl or $C_{1-3}$-alkoxy group, a benzyl, oxazolyl, isoxazolyl, thiazolyl, isothiazolyl, pyrazolyl, pyrrolyl, thienyl, pyridinyl, pyrimidinyl, pyrazinyl, pyridazinyl, imidazolyl or piperidinyl group or $R_2$ and $R_3$ together with the nitrogen atom between them denote a 5- to 7-membered cycloalkyleneimino group, optionally substituted by a carboxy or $C_{1-4}$-alkoxycarbonyl group, onto which a phenyl ring may additionally be fused, particularly those compounds wherein Het denotes one of the abovementioned benzimidazolylene, benzothiazolylene, benzoxazolylene, indolylene, quinazolinylene, quinoxazolinonylene, imidazo[4,5-b]pyridinylene, imidazo-[1,2-a]pyridinylene, thiazolo[5,4-b]pyridinylene or thieno[2,3-d]imidazolylene groups, the tautomers, the prodrugs, the double prodrugs, the stereoisomers and the salts thereof.

Particularly preferred compounds of general formula I above are those wherein

A denotes a carbonyl or sulfonyl group linked to the benzo, pyrido, pyrimido, pyrazino, pyridazino or thieno moiety of the group Het, whilst moreover the abovementioned moieties may not contain an $R_1$ group, B denotes an ethylene group in which the methylene group linked to the group Ar may be replaced by an oxygen or sulfur atom or by an —$NR_1$— group, wherein $R_1$ denotes a hydrogen atom or a $C_{1-4}$-alkyl group, E denotes an $R_bNH$—C(=NH)— group wherein $R_b$ denotes a hydrogen atom, a hydroxy, $C_{1-9}$-alkoxycarbonyl, cyclohexyloxycarbonyl, phenyl-$C_{1-3}$-alkoxycarbonyl, benzoyl, p-$C_{1-3}$-alkyl-benzoyl or pyridinoyl group, whilst the ethoxy moiety in the 2-position of the abovementioned $C_{1-9}$-alkoxycarbonyl group may additionally be substituted by a $C_{1-3}$-alkylsulfonyl or 2-($C_{1-3}$-alkoxy)ethyl group, Ar denotes a 1,4-phenylene group optionally substituted by a chlorine atom or by a methyl, ethyl or methoxy group or it denotes a 2,5-thienylene group, Het denotes a 1-($C_{1-3}$-alkyl)-2,5-benzimidazolylene, 1-cyclopropyl-2,5-benzimidazolylene, 2,5-benzothiazolylene, 1-($C_{1-3}$-alkyl)-2,5-indolylene, 1-($C_{1-3}$-alkyl)-2,5-imidazo[4,5-b]pyridinylene, 3-($C_{1-3}$-alkyl)-2,7-imidazo[1,2-a]pyridinylene, or 1-($C_{1-3}$-alkyl)-2,5-thieno[2,3-d]imidazolylene group, and $R_a$ denotes an $R_2NR_3$— group wherein $R_2$ is a $C_{1-4}$-alkyl group substituted by a carboxy, $C_{1-6}$-alkyloxycarbonyl, benzyloxycarbonyl, $C_{1-3}$-alkylsulfonylaminocarbonyl or 1H-tetrazol-5-yl group, a $C_{2-4}$-alkyl group substituted by a hydroxy, benzyloxy, carboxy-$C_{1-3}$-alkylamino, $C_{1-3}$-alkoxycarbonyl-$C_{1-3}$-alkylamino, N—($C_{1-3}$-alkyl)-carboxy-$C_{1-3}$-alkylamino or N—($C_{1-3}$-alkyl)-$C_{1-3}$-alkoxycarbonyl-$C_{1-3}$-alkylamino group, whilst in the abovementioned groups the carbon atom in the α-position to the adjacent nitrogen atom may not be substituted, $R_3$ denotes a $C_{3-7}$-cycloalkyl group, a propargyl group, wherein the unsaturated part may not be linked directly to the nitrogen atom of the $R_2NR_3$ group, a phenyl group optionally substituted by a fluorine or chlorine atom, or by a methyl or methoxy group, a pyrazolyl, pyridazolyl or pyridinyl group optionally substituted by a methyl group or $R_2$ and $R_3$ together with the nitrogen atom between them denote a 5- to 7-membered cycloalkyleneimino group, optionally substituted by a carboxy or $C_{1-4}$-alkoxycarbonyl group, to which a phenyl ring may additionally be fused, the tautomers, the stereoisomers and the salts thereof.

Most particularly preferred compounds of the above general formula I are those wherein A denotes a carbonyl or sulfonyl group linked to the benzo, pyrido, or thieno moiety of the group Het, whilst moreover the abovementioned moieties may not contain an $R_1$ group, B denotes an ethylene group in which the methylene group linked to the group Ar may be replaced by an oxygen or sulfur atom or by an —$NR_1$— group, wherein $R_1$ denotes a hydrogen atom or a methyl group, E denotes an R$_b$NH—C(=NH)— group, wherein
  R$_b$ denotes a hydrogen atom or a hydroxy, C$_{1-9}$-alkoxycarbonyl, cyclohexyloxycarbonyl, benzyloxycarbonyl, benzoyl, p-C$_{1-3}$-alkylbenzoyl or nicotinoyl group, whilst the ethoxy moiety in the 2-position of the abovementioned C$_{1-9}$-alkoxycarbonyl group may additionally be substituted by a C$_{1-3}$-alkylsulfonyl or 2-(C$_{1-3}$-alkoxy)ethyl group,
Ar denotes a 1,4-phenylene group optionally substituted by a chlorine atom or by a methyl, ethyl or methoxy group, or it denotes a 2,5-thienylene group,
Het denotes a 1-methyl-2,5-benzimidazolylene, 1-cyclopropyl-2,5-benzimidazolylene, 2,5-benzothiazolylene, 1-methyl-2,5-indolylene, 1-methyl-2,5-imidazo[4,5-b]pyridinylene, 3-methyl-2,7-imidazo[1,2-a]pyridinylene or 1-methyl-2,5-thieno[2,3-d]imidazolylene group and
R$_a$ denotes a R$_2$NR$_3$— group wherein
  R$_2$ denotes a C$_{1-3}$-alkyl group which may be substituted by a carboxy, C$_{1-6}$-alkyloxycarbonyl, benzyloxycarbonyl, methylsulfonylaminocarbonyl, or 1H-tetrazol-5-yl group,
  a C$_{2-3}$-alkyl group substituted by a hydroxy, benzyloxy, carboxy-C$_{1-3}$-alkylamino, C$_{1-3}$-alkoxycarbonyl-C$_{1-3}$-alkylamino, N—(C$_{1-3}$-alkyl)-carboxy-C$_{1-3}$-alkylamino, or N—(C$_{1-3}$-alkyl)-C$_{1-3}$-alkoxycarbonyl-C$_{1-3}$-alkylamino group, whilst in the abovementioned groups the carbon atom in the a-position to the adjacent nitrogen atom may not be substituted, and
  R$_3$ denotes a propargyl group, wherein the unsaturated moiety may not be linked directly to the nitrogen atom of the R$_2$NR$_3$ group, a phenyl group optionally substituted by a fluorine or chlorine atom, or by a methyl or methoxy group, or denotes a pyridinyl group,
particularly those wherein A denotes a carbonyl group linked to the benzo or thieno moiety of the group Het,
B denotes an ethylene group wherein the methylene group attached to the group Ar may be replaced by an —NR$_1$— group, wherein
  R$_1$ denotes a hydrogen atom or a methyl group,
E denotes an R$_b$NH—C(=NH)— group wherein
  R$_b$ is a hydrogen atom, a hydroxy, C$_{1-9}$-alkoxycarbonyl, cyclohexyloxycarbonyl, benzyloxycarbonyl, benzoyl, p-C$_{1-3}$-alkylbenzoyl or nicotinoyl group, whilst the ethoxy moiety in the 2-position of the abovementioned C$_{1-9}$-alkoxycarbonyl group may additionally be substituted by a methylsulfonyl or 2-ethoxyethyl group,
Ar denotes a 1,4-phenylene group optionally substituted by a methoxy group, or denotes a 2,5-thienylene group,
Het denotes a 1-methyl-2,5-benzimidazolylene, 2,5-benzothiazolylene, 1-methyl-2,5-indolylene, or 1-methyl-2,5-thieno[2,3-d]imidazolylene group and
R$_a$ denotes an R$_2$NR$_3$— group wherein
  R$_2$ denotes a C$_{1-3}$-alkyl group which may be substituted by a carboxy, C$_{1-6}$-alkyloxycarbonyl, benzyloxycarbonyl, methylsulfonylaminocarbonyl or 1H-tetrazol-5-yl group,
  a C$_{2-3}$-alkyl group substituted by a hydroxy, benzyloxy, carboxy-C$_{1-3}$-alkylamino, C$_{1-3}$-alkoxycarbonyl-C$_{1-3}$-alkylamino, N—(C$_{1-3}$-alkyl)-carboxy-C$_{1-3}$-alkylamino or N—(C$_{1-3}$-alkyl)-C$_{1-3}$-alkoxycarbonyl-C$_{1-3}$-alkylamino group, whilst in the abovementioned groups the carbon atom in the a-position to the adjacent nitrogen atom may not be substituted, and
  R$_3$ denotes a phenyl group optionally substituted by a fluorine atom, or denotes a 2-pyridinyl group,
the tautomers, stereoisomers and the salts thereof.

The following are mentioned as examples of particularly preferred compounds:

(a) 2-[N-(4-amidinophenyl)aminomethyl]benzthiazole-5-carboxylic acid-N-phenyl-N-(2-carboxyethyl)amide,
(b) 2-[N-(4-amidinophenyl)-N-methylaminomethyl]benzthiazol-5-yl-carboxylic acid-N-phenyl-N-(2-hydroxycarbonylethyl)amide,
(c) 1-Methyl-2-[N-(4-amidinophenyl)aminomethyl]benzimidazol-5-yl-carboxylic acid-N-phenyl-N-(2-hydroxycarbonylethyl)amide,
(d) 1-Methyl-2-[N-(4-amidinophenyl)aminomethyl]benzimidazol-5-yl-carboxylic acid-N-phenyl-N-(3-hydroxycarbonylpropyl)amide,
(e) 1-Methyl-2-[N-(4-amidinophenyl)aminomethyl]benzimidazol-5-yl-carboxylic acid-N-(2-pyridyl)-N-(hydroxycarbonylmethyl)amide,
(f) 1-Methyl-2-[2-(2-amidinothiophen-5-yl)ethyl]benzimidazol-5-yl-carboxylic acid-N-(2-pyridyl)-N-(2-hydroxycarbonylethyl)amide,
(g) 1-Methyl-2-[N-(4-amidinophenyl)aminomethyl]benzimidazol-5-yl-carboxylic acid-N-(2-pyridyl)-N-(2-hydroxycarbonylethyl)amide,
(h) 1-Methyl-2-[2-(4-amidinophenyl)ethyl]benzimidazol-5-yl-carboxylic acid-N-(2-pyridyl)-N-(2-hydroxycarbonylethyl)amide,
(i) 1-Methyl-2-[2-(4-amidinophenyl)ethyl]benzimidazol-5-yl-carboxylic acid-N-phenyl-N-(2-hydroxycarbonylethyl)amide,
(j) 1-Methyl-2-[2-(4-amidinophenyl)ethyl]benzimidazol-5-yl-carboxylic acid-N-phenyl-N-[2-(1H-tetrazol-5-yl)ethyl]amide,
(k) 1-Methyl-2-[N-(4-amidinophenyl)aminomethyl]benzimidazol-5-yl-carboxylic acid-N-phenyl-N-[2-(1H-tetrazol-5-yl)ethyl]amide,
(l) 1-Methyl-2-[N-(4-amidinophenyl)-N-methylaminomethyl]benzimidazol-5-yl-carboxylic acid-N-(2-pyridyl)-N-(2-hydroxycarbonylethyl)amide,
(m) 1-Methyl-2-[N-(4-amidinophenyl)-N-methylaminomethyl]benzimidazol-5-yl-carboxylic acid-N-(3-pyridyl)-N-(2-hydroxycarbonylethyl)amide,
(n) 1-Methyl-2-[N-(4-amidinophenyl)-N-methylaminomethyl]benzimidazol-5-yl-carboxylic acid-N-phenyl-N-(2-hydroxycarbonylethyl)amide,
(o) 1-Methyl-2-[N-(4-amidinophenyl)aminomethyl]benzimidazol-5-yl-carboxylic acid-N-phenyl-N-[(N-hydroxycarbonylethyl-N-methyl)-2-aminoethyl]amide,
(p) 1-Methyl-2-[N-(4-amidinophenyl)aminomethyl]benzimidazol-5-yl-carboxylic acid-N-(3-fluorophenyl)-N-(2-hydroxycarbonylethyl)amide,
(q) 1-Methyl-2-[N-(4-amidinophenyl)aminomethyl]benzimidazol-5-yl-carboxylic acid-N-(4-fluorophenyl)-N-(2-hydroxycarbonylethyl)amide,
(r) 1-Methyl-2-[N-(4-amidino-2-methoxyphenyl)aminomethyl]benzimidazol-5-yl-carboxylic acid-N-phenyl-N-(2-hydroxycarbonylethyl)amide,
(s) 1-Methyl-2-[N-(4-amidino-2-methoxyphenyl)aminomethyl]benzimidazol-5-yl-carboxylic acid-N-(2-pyridyl)-N-(2-hydroxycarbonylethyl)amide,
(t) 1-Methyl-2-[N-(4-amidinophenyl)aminomethyl]indol-5-yl-carboxylic acid-N-phenyl-N-(2-methoxycarbonylethyl)amide, and
(u) 1-Methyl-2-[N-(4-amidinophenyl)aminomethyl]thieno[2,3-d]imidazol-5-yl-carboxylic acid-N-phenyl-N-(2-hydroxycarbonylethyl)amide, the tautomers, prodrugs, double prodrugs, stereoisomers and the salts thereof.

The new compounds may be prepared by methods known per se, for example by the following methods:

a. In order to prepare a compound of general formula I, wherein E denotes an $R_b NH-C(=NH)-$ group, wherein $R_b$ is a hydrogen atom, a hydroxy or $C_{1-3}$-alkyl group:

By reacting a compound of general formula

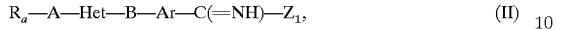

$$R_a-A-Het-B-Ar-C(=NH)-Z_1, \quad (II)$$

optionally formed in the reaction mixture, wherein:

A, B, Ar, Het and $R_a$ are as hereinbefore defined and $Z_1$ denotes an alkoxy or aralkoxy group such as the methoxy, ethoxy, n-propoxy, isopropoxy or benzyloxy group or an alkylthio or aralkylthio group such as the methylthio, ethylthio, n-propylthio or benzylthio group, with an amine of general formula

$$H_2N-R_b' \quad (III)$$

wherein $R_b'$ denotes a hydrogen atom or a hydroxy or $C_{1-3}$-alkyl group.

The reaction is conveniently carried out in a solvent such as methanol, ethanol, n-propanol, water, methanol/water, tetrahydrofuran or dioxane at temperatures between 0° C. and 150° C., preferably at temperatures between 20° C. and 120° C., with a compound of general formula III or with a corresponding acid addition salt such as ammonium carbonate, for example.

A compound of general formula II may be obtained, for example, by reacting a compound of general formula I wherein E denotes a cyano group, with a corresponding alcohol such as methanol, ethanol, n-propanol, isopropanol or benzyl alcohol in the presence of an acid such as hydrochloric acid or by reacting a corresponding amide with a trialkyloxonium salt such as triethyloxonium tetrafluoroborate in a solvent such as methylene chloride, tetrahydrofuran or dioxane at temperatures between 0° C. and 50° C., but preferably at 20° C., or a corresponding nitrile with hydrogen sulfide, appropriately in a solvent such as pyridine or dimethylformamide and in the presence of a base such as triethylamine and subsequent alkylation of the resulting thioamide with a corresponding alkyl or aralkyl halide.

b. In order to prepare a compound of general formula I wherein the $R_a-A-$ group and E are as hereinbefore defined, with the proviso that the $R_a-A-$ group contains a carboxy group and E as hereinbefore defined or that the $R_a-A-$ group is as hereinbefore defined and E denotes an $NH_2-C(=NH)-$ group, or that the $R_a-A-$ group contains a carboxy group and E denotes an $NH_2-C(=NH)-$ group:

Converting a compound of general formula

$$R_a'-A-Het-B-Ar-C-E', \quad (IV)$$

wherein

A, B, Ar and Het are as hereinbefore defined and the $R_a'-A-$ group and E' have the meanings given for the $R_a-A-$ group and E hereinbefore, with the proviso that the $R_a'-A-$ group contains a group which may be converted into a carboxyl group by hydrolysis, treatment with an acid or base, thermolysis or hydrogenolysis and E is as hereinbefore defined or E' denotes a group which may be converted into an $NH_2-C(=NH)-$ group by hydrolysis, treatment with an acid or base, thermolysis or hydrogenolysis and the $R_a'-A-$ group has the meanings given for the $R_a-A-$ group hereinbefore or the $R_a'-A-$ group contains a group which may be converted into a carboxyl group by hydrolysis, treatment with an acid or base, thermolysis or hydrogenolysis and E' denotes a group which may be converted into an $NH_2-C(=NH)-$ group by hydrolysis, treatment with an acid or base, thermolysis or hydrogenolysis, is converted by hydrolysis, treatment with an acid or base, thermolysis or hydrogenolysis into a compound of general formula I, wherein the $R_a-A-$ group and E are as hereinbefore defined, with the proviso that the $R_a-A-$ group contains a carboxy group and E is as hereinbefore defined or the $R_a-A-$ group has the meanings given above and E denotes an $NH_2-C(=NH)-$ group or the $R_a-A-$ group contains a carboxy group and E denotes an $NH_2-C(=NH)-$ group.

Examples of groups which may be converted into a carboxy group include a carboxyl group protected by a protecting group and the functional derivatives thereof, e.g., the unsubstituted or substituted amides, esters, thioesters, trimethylsilylesters, orthoesters or iminoesters which may conveniently be converted into a carboxyl group by hydrolysis, the esters thereof with tertiary alcohols, e.g., the tert-butylester, which are conveniently converted into a carboxyl group by treatment with an acid or by thermolysis, and the esters thereof with aralkanols, e.g., the benzylester, which are conveniently converted into a carboxyl group by hydrogenolysis.

The hydrolysis is expediently carried out either in the presence of an acid such as hydrochloric acid, sulfuric acid, phosphoric acid, acetic acid, trichloroacetic acid, trifluoroacetic acid or mixtures thereof or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane at temperatures between −10° C. and 120° C., e.g., at temperatures between room temperature and the boiling temperature of the reaction mixture.

If the $R_a'-A-$ group and/or E' in a compound of formula IV contains the tert-butyl or tert-butyloxycarbonyl group, for example, these may also be cleaved by treating with an acid such as trifluoroacetic acid, formic acid, p-toluenesulfonic acid, sulfuric acid, hydrochloric acid, phosphoric acid or polyphosphoric acid, optionally in an inert solvent such as methylene chloride, chloroform, benzene, toluene, diethylether, tetrahydrofuran or dioxane, preferably at temperatures between −10° C. and 120° C., e.g., at temperatures between 0° C. and 60° C., or thermally optionally in an inert solvent such as methylene chloride, chloroform, benzene, toluene, tetrahydrofuran or dioxane and preferably in the presence of a catalytic quantity of an acid such as p-toluenesulfonic acid, sulfuric acid, phosphoric acid, or polyphosphoric acid, preferably at the boiling temperature of the solvent used, e.g., at temperatures between 40° C. and 120° C.

If the $R_a'-A-$ group and/or E' in a compound of formula IV contains the benzyloxy or benzyloxycarbonyl group, for example, these may also be cleaved by hydrogenolysis in the presence of a hydrogenation catalyst such as palladium/charcoal in a suitable solvent such as methanol, ethanol, ethanol/water, glacial acetic acid, ethyl acetate, dioxane, or dimethylformamide, preferably at temperatures between 0° C. and 50° C., e.g., at room temperature, under a hydrogen pressure of 1 to 5 bar.

c. In order to prepare a compound of general formula I wherein the $R_a$—a— group contains one of the ester groups mentioned in the definition of the $R_a$—A— group hereinbefore:

Reaction of a compound of general formula

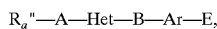  (V)

wherein

B, E, Ar, and Het are as hereinbefore defined, and the $R_a''$—A— group has the meanings given for the $R_a$—a— group hereinbefore, with the proviso that the $R_a''$—A— group contains a carboxyl group or a group which may be converted into a corresponding ester group by means of an alcohol, with an alcohol of general formula

  (VI)

wherein $R_7$ is the alkyl moiety of one of the above-mentioned groups which may be cleaved in vivo, with the exception of the $R_6$—CO—O—$(R_5CR_6)$— group for a carboxyl group, or with the formamide acetals thereof;

or with a compound of general formula

  (VII)

wherein $R_8$ denotes the alkyl moiety of one of the above-mentioned groups which may be cleaved in vivo, with the exception of the $R_6$—CO—O—$(R_5CR_6)$— group for a carboxyl group, and $Z_2$ denotes a leaving group such as a halogen atom, e.g., a chlorine or bromine atom.

The reaction with an alcohol of general formula VI is conveniently carried out in a solvent or mixture of solvents such as methylene chloride, benzene, toluene, chlorobenzene, tetrahydrofuran, benzene/tetrahydrofuran, or dioxane, but preferably in an alcohol of general formula VI, optionally in the presence of an acid such as hydrochloric acid or in the presence of a dehydrating agent, e.g., in the presence of isobutylchloroformate, thionyl chloride, trimethylchlorosilane, hydrochloric acid, sulfuric acid, methanesulfonic acid, p-toluenesulfonic acid, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole, N,N'-thionyldiimidazole, triphenylphosphine/carbon tetrachloride, or triphenylphosphine/diethylazodicarboxylate, optionally in the presence of a base such as potassium carbonate, N-ethyldiisopropylamine, or N,N-dimethylaminopyridine, conveniently at temperatures between 0° C. and 150° C., preferably at temperatures between 0° C. and 80° C.

With a compound of general formula VII the reaction is usefully carried out in a solvent such as methylene chloride, tetrahydrofuran, dioxane, dimethylsulfoxide, dimethylformamide, or acetone, optionally in the presence of a reaction accelerator such as sodium or potassium iodide and preferably in the presence of a base such as sodium carbonate or potassium carbonate or in the presence of a tertiary organic base such as N-ethyldiisopropylamine or N-methylmorpholine, which may act as solvent at the same time, or optionally in the presence of silver carbonate or silver oxide at temperatures between −30° C. and 100° C., but preferably at temperatures between −10° C. and 80° C.

d. In order to prepare a compound of general formula I wherein $R_b$ denotes a group which may be cleaved in vivo:

Reacting a compound of general formula:

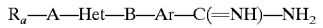  (VIII)

wherein $R_a$, A, Het, B, and Ar are as hereinbefore defined, with a compound of general formula:

  (IX)

wherein $R_5$ denotes a group which may be cleaved in vivo, and $Z_2$ denotes a nucleofugic leaving group such as a halogen atom, e.g., a chlorine, bromine, or iodine atom.

The reaction is preferably carried out in a solvent such as methanol, ethanol, methylene chloride, tetrahydrofuran, toluene, dioxane, dimethylsulfoxide, or dimethylformamide, optionally in the presence of an inorganic or tertiary organic base, preferably at temperatures between 20° C. and the boiling temperature of the solvent used.

With a compound of general formula IX, wherein $Z_2$ denotes a nucleofugic leaving group, the reaction is preferably carried out in a solvent such as methylene chloride, acetonitrile, tetrahydrofuran, toluene, dimethylformamide, or dimethylsulfoxide, optionally in the presence of a base such as sodium hydride, potassium carbonate, potassium tert-butoxide, or N-ethyldiisopropylamine at temperatures between 0° C. and 60° C.

e. In order to prepare a compound of general formula I wherein B denotes an ethylene group, in which a methylene group is replaced by a sulfinyl or sulfonyl group:

Oxidation of a compound of general formula:

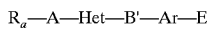  (X)

wherein

A, E, Ar, Het, and $R_a$ are as hereinbefore defined, and B' denotes an ethylene group, wherein a methylene group is replaced by a sulfenyl or sulfinyl group.

The oxidation is preferably carried out in a solvent or mixture of solvents, e.g., in water, water/pyridine, acetone, methylene chloride, glacial acetic acid, glacial acetic acid/acetic anhydride, dilute sulfuric acid, or trifluoroacetic acid, and depending on the oxidizing agent used, at temperatures between −80° C. and 100° C.

In order to prepare a corresponding sulfinyl compound of general formula I oxidation is conveniently carried out with one equivalent of the oxidizing agent used, e.g., with hydrogen peroxide in glacial acetic acid, trifluoroacetic acid, or formic acid at 0° C. to 20° C., or in acetone at 0° C. to 60° C., with a peracid such as performic acid in glacial acetic acid, or trifluoroacetic acid at 0° C. to 50° C., or with m-chloroperbenzoic acid in methylene chloride, chloroform, or dioxane at −20° C. to 80° C., with sodium metaperiodate in aqueous methanol, or ethanol at −15° C. to 25° C., with bromine in glacial acetic acid, or aqueous acetic acid, optionally in the presence of a weak base such as sodium acetate, with N-bromosuccinimide in ethanol, with tert-butylhypochlorite in methanol at −80° C. to −30° C., with iodobenzodichloride in aqueous pyridine at 0° C. to 50° C., with nitric acid in glacial acetic acid at 0° C. to 20° C., with chromic acid in glacial acetic acid, or in acetone at 0° C. to 20° C. and with sulfuryl chloride in methylene chloride at −70° C., the resulting thioether chlorine complex is conveniently hydrolyzed with aqueous ethanol.

In order to prepare a sulfonyl compound of general formula I, oxidation is carried out starting from a corresponding sulfinyl compound, conveniently with one or more equivalents of the oxidizing agent used, or starting from a corresponding sulfenyl compound, conveniently with two or more equivalents of the oxidizing agent used, e.g., with hydrogen peroxide in glacial acetic acid/acetic anhydride, trifluoroacetic acid, or in formic acid at 20 to 100° C., or in acetone at 0 to 60° C., with a peracid such as performic acid, or with m-chloroperbenzoic acid in glacial acetic acid, trifluoroacetic acid, methylene chloride, or chloroform at temperatures between 0° C. and 60° C., with nitric acid in glacial acetic acid at 0° C. to 20° C., with chromic acid, or potassium permanganate in glacial acetic acid, water/sulfuric acid, or in acetone at 0° C. to 20° C. Thus, by carrying out oxidation, for example, starting from a corresponding sulfenyl compound, preferably in methylene chloride, by treating with a corresponding amount of m-chloroperbenzoic acid at temperatures between 20° C. and the reflux temperature of the reaction mixture, a corresponding sulfonyl compound of general formula I is obtained which may still contain a small amount of the corresponding sulfinyl compound.

f. In order to prepare a compound of general formula I wherein E is a cyano group and B is an ethylene group in which a methylene group linked either to group Het or to Ar is replaced by an oxygen or sulfur atom or by a sulfinyl, sulfonyl, carbonyl, or —NR$_1$— group:

Reacting a compound of general formula:

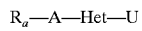

R$_a$—A—Het—U    (XI)

with a compound of general formula:

V—Ar—CN    (XII)

wherein

R$_a$, A, Ar, and Het are as hereinbefore defined,
one of the groups U or V denotes an HO—, HS—, HOSO—, HOSO$_2$—, or HNR$_1$— group, and the other group denotes a Z$_3$CH$_2$— group, wherein R$_1$ is as hereinbefore defined, and Z$_3$ denotes a nucleofugic leaving group such as a halogen atom, e.g., a chlorine, bromine, or iodine atom.

The reaction is preferably carried out in a solvent such as methanol, ethanol, methylene chloride, tetrahydrofuran, toluene, dioxane, dimethylsulfoxide, or dimethylformamide, optionally in the presence of an inorganic or a tertiary organic base, preferably at temperatures between 20° C. and the boiling temperature of the solvent used.

g. In order to prepare a compound of general formula I, wherein E is a cyano group and R$_a$ denotes an R$_2$NR$_3$— group:

Reacting a compound of general formula:

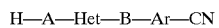

H—A—Het—B—Ar—CN    (XIII)

wherein

A, B, Het, and Ar are as hereinbefore defined, with an amine of general formula:

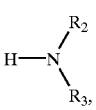

wherein

R$_2$ and R$_3$ are as hereinbefore defined, or with the reactive derivatives thereof.

The reaction of an acid of general formula XIII is optionally carried out in a solvent or mixture of solvents such as methylene chloride, dimethylformamide, benzene, toluene, chlorobenzene, tetrahydrofuran, benzene/tetrahydrofuran, or dioxane or in a corresponding amine of general formula III, optionally in the presence of a dehydrating agent, e.g., in the presence of isobutyl-chloroformate, tetraethylorthocarbonate, trimethylorthoacetate, 2,2-dimethoxypropane, tetramethoxysilane, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxybenzotriazole, 2-(1H-benzotriazol-1-yl)-1,1,3,3-tetramethyluronium tetrafluoroborate, 2-(1H-benzotriazol-1-yl)-1,1,3,3-tetramethyluronium tetrafluoroborate/1-hydroxybenzotriazole, N,N'-carbonyldiimidazole, or triphenylphosphine/carbon tetrachloride and optionally with the addition of a base such as pyridine, 4-dimethylaminopyridine, N-methylmorpholine, or triethylamine, conveniently at temperatures between 0° C. and 150° C., preferably at temperatures between 0° C. and 100° C.

The reaction of a corresponding reactive compound of general formula XIII such as the esters, imidazolides or halides thereof with an amine of general formula XIV is preferably carried out in a corresponding amine as solvent, optionally in the presence of another solvent such as methylene chloride or ether and preferably in the presence of a tertiary organic base such as triethylamine, N-ethyldiisopropylamine, or N-methylmorpholine at temperatures between 0° C. and 150° C., preferably at temperatures between 50° C. and 100° C.

h. In order to prepare a benzimidazolyl, benzothiazolyl, or benzoxazolyl compound of general formula I wherein B denotes an ethylene group:

Reacting a compound of general formula:

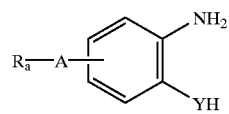

wherein R$_a$, A, and Y are as hereinbefore defined, with a compound of general formula:

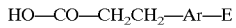

HO—CO—CH$_2$CH$_2$—Ar—E    (XVI)

wherein Ar and E are as hereinbefore defined, or with the reactive derivatives thereof.

The reaction is conveniently carried out in a solvent or mixture of solvents such as methylene chloride, dimethylformamide, benzene, toluene, chlorobenzene, tetrahydrofuran, benzene/tetrahydrofuran, or dioxane, optionally in the presence of a dehydrating agent, e.g., in the presence of isobutylchloroformate, tetraethylorthocarbonate, trimethylorthoacetate, 2,2-dimethoxypropane, tetramethoxysilane, thionyl chloride, trimethylchlorosilane, phosphorus tichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxybenzotriazole, 2-(1H-benzotriazol-1-yl)-1,1,3,3-tetramethyluronium tetrafluoroborate, 2-(1H-benzotriazol-1-yl)-,1,1,3,3-tetramethyluronium tetrafluoroborate/1-hydroxybenzotriazole, N,N'-carbonyldiimidazole, or triphenylphosphine/carbon tetrachloride, and optionally with the addition of a base such as pyridine, 4-dimethylaminopyridine, N-methylmorpholine, or triethylamine, appropriately at temperatures between 0° C. and 150° C., preferably at temperatures between 0° C. and 100° C.

The reaction of a corresponding reactive compound of general formula XVI such as the esters, imidazolides or halides thereof with an amine of general formula XV is preferably carried out in a solvent such as methylene chloride, ether, or tetrahydrofuran and preferably in the presence of a tertiary organic base such as triethylamine, N-ethyldiisopropylamine, or N-methylmorpholine, which may simultaneously be used as solvents, at temperatures between 0° C. and 150° C., preferably at temperatures between 50° C. and 100° C.

i. In order to prepare a quinoxalin-2-one compound of the general formula:

Reacting a compound of general formula:

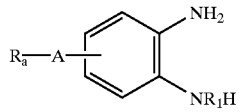

(XVII)

wherein $R_a$, $R_1$, and A are as hereinbefore defined, with a compound of general formula:

 (XVIII)

wherein

Ar and E are as hereinbefore defined, or with the reactive derivatives thereof.

The reaction is conveniently carried out in a solvent or mixture of solvents such as methylene chloride, dimethylformamide, benzene, toluene, chlorobenzene, tetrahydrofuran, benzene/tetrahydrofuran, ethanol, or dioxane, optionally in the presence of a dehydrating agent, e.g., in the presence of isobutyl chloroformate, tetraethyl orthocarbonate, trimethyl orthoacetate, 2,2-dimethoxypropane, tetramethoxysilane, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxybenzotriazole, 2-(1H-benzotriazol-1-yl)-1,1,3,3-tetramethyluronium tetrafluoroborate, 2-(1H-benzotriazol-1-yl)-1,1,3,3-tetramethyluronium tetrafluoroborate/1-hydroxybenzotriazole, N,N'-carbonyldulmidazole, or triphenylphosphine/carbon tetrachloride, and optionally with the addition of a base such as pyridine, 4-dimethylaminopyridine, N-methylmorpholine, or triethylamine, appropriately at temperatures of between 0° C. and 150° C., preferably at temperatures of between 0° C. and 100° C.

However, it is particularly preferred to carry out the reaction with a corresponding reactive compound of general formula XVIII such as the esters, imidazolides or halides thereof with an amine of general formula XVII in a solvent such as methylene chloride, ether, ethanol, or tetrahydrofuran and optionally in the presence of a tertiary organic base such as triethylamine, N-ethyldiisopropylamine, or N-methylmorpholine, which may simultaneously serve as solvent, at temperatures of between 0° C. and 150° C., preferably at temperatures of between 50° C. and 100° C.

j. In order to prepare a compound of general formula I wherein $R_2$ denotes a $C_{1-4}$-alkyl group substituted by an alkylsulfonylaminocarbonyl group:

Reacting a compound of general formula:

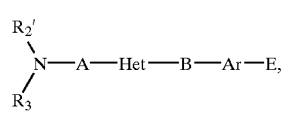

(IXX)

wherein $R_3$, A, B, E, and Het are as hereinbefore defined, and $R_2'$ denotes a $C_{1-4}$-alkyl group substituted by a carboxy group, or the reactive derivatives thereof, with a salt of a compound of general formula:

 (XX)

The reaction is preferably carried out with a corresponding reactive compound of general formula IXX such as the esters, imidazolides, or halides thereof with a salt of a compound of general formula XX, preferably with an alkali metal salt thereof such as a sodium salt, in a solvent such as methylene chloride, ether, ethanol, tetrahydrofuran, or dimethylformamide at temperatures between 0° C. and 150° C., preferably at temperatures of between 50° C. and 100° C.

In the reactions described hereinbefore, any reactive groups present such as hydroxy, carboxy, amino, alkylamino, or imino groups may be protected during the reaction by means of conventional protecting groups which are removed by cleaving after the reaction.

For example, the protecting group for a hydroxy group may be the trimethylsilyl, acetyl, benzoyl, tert-butyl, trityl, benzyl, or tetrabydropyranyl group, the protecting group for a carboxyl group may be the trimethylsilyl, methyl, ethyl, tert-butyl, benzyl, or tetrahydropyranyl group, and the protecting group for an amino, alkylamino, or imino group may be the acetyl, trifluoroacetyl, benzoyl, ethoxycarbonyl, tert-butoxycarbonyl, benzyloxycarbonyl, benzyl, methoxybenzyl, or 2,4-dimethoxybenzyl group and for the amino group the phthalyl group may also be considered.

The optional subsequent cleaving of a protecting group may, for example, be carried out hydrolytically in an aqueous solvent, e.g., in water, isopropanol/water, tetrahydrofuran/water, or dioxane/water, in the presence of an acid such as trifluoroacetic acid, hydrochloric acid, or sulfuric acid, or in the presence of an alkali metal base such as lithium hydroxide, sodium hydroxide, or potassium hydroxide or by ether cleaving, e.g., in the presence of iodotrimethylsilane, at temperatures between 0° C. and 100° C., preferably at temperatures between 10° C. and 50° C.

However, a benzyl, methoxybenzyl, or benzyloxycarbonyl group may for example be cleaved hydrogenolytically, e.g., using hydrogen in the presence of a catalyst such as palladium/charcoal in a solvent such as methanol, ethanol, ethyl acetate, dimethylformamide, dimethylformamide/acetone, or glacial acetic acid, optionally with the addition of an acid such as hydrochloric acid, at temperatures between 0° C. and 50° C., but preferably at room temperature, under a hydrogen pressure of 1 to 7 bar, preferably 3 to 5 bar.

A methoxybenzyl group may also be cleaved in the presence of an oxidizing agent such as cerium (IV) ammonium nitrate in a solvent such as methylene chloride, acetonitrile, or acetonitrile/water at temperatures between 0° C. and 50° C., but preferably at room temperature.

However, a 2,4-dimethoxybenzyl group is preferably cleaved in trifluoroacetic acid in the presence of anisole.

A tert-butyl or tert-butyloxycarbonyl group is preferably cleaved by treatment with an acid such as trifluoroacetic acid or hydrochloric acid, optionally using a solvent such as methylene chloride, dioxane, or ether.

A phthalyl group is preferably cleaved in the presence of hydrazine or a primary amine such as methylamine, ethylamine, or n-butylamine in a solvent such as methanol, ethanol, isopropanol, toluene/water, or dioxane, at temperatures between 20° C. and 50° C.

An allyloxycarbonyl group is cleaved by treating with a catalytic amount of tetrakis(triphenylphosphine)palladium (0), preferably in a solvent such as tetrahydrofuran and preferably in the presence of an excess of a base such as morpholine or 1,3-dimedone, at temperatures between 0° C. and 100° C., preferably at room temperature and under inert gas, or by treating with a catalytic amount of tris (triphenylphosphine)rhodium (I) chloride, in a solvent such as aqueous ethanol and optionally in the presence of a base such as 1,4-diazabicyclo[2,2,2]octane, at temperatures between 20° C. and 70° C.

The compounds of general formulae II to XX used as starting materials, some of which are known from the literature, may be obtained by methods known from the literature and moreover their production is described in the Examples.

Thus, for example, a compound of general formula II is obtained by reacting a corresponding nitrile which in turn is conveniently obtained by processes f to h, with a corresponding thio or alcohol in the presence of hydrogen chloride or bromide.

A compound of general formulae IV, V, VIII, X, and IXX used as starting material is conveniently obtained according to a process of the present invention.

A starting compound of general formula XI in which U denotes a halomethyl group is conveniently obtained by cyclization of a corresponding ester which is substituted in the o-position by a suitable halogen atom and a methoxyacetamido group, to form a corresponding bicyclic 2-alkoxymethyl compound, optionally subsequent hydrolysis and optionally subsequent amidation of a resulting carboxylic acid with a corresponding amine, converting the alkoxymethyl compound thus obtained into the corresponding halomethyl compound, which can if necessary be subsequently converted into the desired compound by means of a suitable compound. If the cyclization is carried out with a suitable carbonic acid derivative, a starting compound of general formula XI is obtained wherein U denotes a hydroxy, mercapto, or amino group.

A starting compound of general formula XIII is obtained by cyclization of a corresponding o-disubstituted ester, followed by saponification of the resulting ester and subsequent amidation of the carboxylic acid thus obtained with a corresponding amine.

Furthermore, an imidazopyridine substituted in the 5-position by a methyl group and obtained by cyclization can be converted, via the corresponding N-oxide, into the corresponding hydroxymethyl compound which is converted by oxidation into the desired carboxylic acid of general formula XIII.

The compounds of general formulae III, VI, VII, IX, and XII used as starting materials are obtained by conventional methods, for example by reducing an aromatic ester substituted in the o-position by an optionally substituted amino group and a nitro group, and optionally subsequent cyclization of the resulting o-diamino compound with a corresponding carboxylic acid.

Furthermore, the compounds of general formula I obtained may be separated into their enantiomers and/or diastereomers.

Thus, for example, the compounds of general formula I obtained which occur in racemate form may be separated by methods known per se (see N. L. Allinger and E. L. Eliel in "Topics in Stereochemistry", Vol. 6, Wiley Interscience, 1971) into their optical antipodes, and compounds of general formula I having at least 2 asymmetric carbon atoms may be separated on the basis of their physical-chemical differences using known methods, e.g., by chromatography and/or fractional crystallization, into the diastereomers thereof, which, if they occur in racemic form, may subsequently be separated into the enantiomers as mentioned above.

The separation of enantiomers is preferably effected by column separation on chiral phases or by recrystallization from an optically active solvent or by reacting with an optically active substance, especially acids and the activated derivatives thereof or alcohols, which forms salts or derivatives such as, e.g., esters or amides with the racemic compound, and separation of the diastereomeric salt mixture or derivative thus obtained, e.g., on the basis of their different solubilities, whilst the free antipodes may be released from the pure diastereomeric salts or derivatives by the action of suitable agents. Particularly common, optically active acids are, for example, the D- and L-forms of tartaric acid, and dibenzoyltartaric acid, di-o-tolyl tartaric acid, malic acid, mandelic acid, camphorsulfonic acid, glutamic acid, aspartic acid, and quinaldic acid. Examples of optically active alcohols include for example (+)- or (−)-menthol and examples of optically active acyl groups in amides include, for example, (+)- or (−)-menthyloxycarbonyl.

Moreover, the compounds of formula I obtained may be converted into the salts thereof, particularly for pharmaceutical use into the physiologically acceptable salts thereof with inorganic or organic acids. Examples of suitable acids include for example hydrochloric acid, hydrobromic acid, sulfuric acid, phosphoric acid, fumaric acid, succinic acid, lactic acid, citric acid, tartaric acid, or maleic acid.

In addition, the new compounds of formula I thus obtained, if they contain a carboxyl group, may subsequently, if desired, be converted into the salts thereof with inorganic or organic bases, more particularly, for pharmaceutical use, into the physiologically acceptable salts thereof. Examples of suitable bases include for example sodium hydroxide, potassium hydroxide, cyclohexylamine, ethanolamine, diethanolamine, and triethanolamine.

As already mentioned, the new compounds of general formula I and the salts thereof have valuable properties.

Thus, the compounds of general formula I wherein E denotes a cyano group are valuable intermediate products for preparing the other compounds of general formula I and the compounds of general formula I wherein E denotes an $R_b$NH—C(=NH)— group and the tautomers, the stereoisomers and the physiologically acceptable salts thereof have valuable pharmacological properties, particularly a thrombin-inhibiting effect, an effect of prolonging the thrombin time and an inhibitory effect on related serine proteases such as e.g., trypsin, urokinase factor VIIa, factor Xa, factor IX, factor XI, and factor XII, whilst a few compounds such as for example the compound of Example 16 simultaneously also have a slight inhibitory effect on thrombocyte aggregation.

For example, the following compounds:

A is 2-[N-(4-amidinophenyl)aminomethyl]benzthiazole-5-carboxylic acid-N-phenyl-N-(2-carboxyethyl)amide;

B is 1-methyl-2-[2-(4-amidinophenyl)ethyl]benzimidazol-5-yl-carboxylic acid-N-phenyl-N-(3-hydroxycarbonylpropyl)amide;

C is 1-methyl-2-[(4-amidinophenyl)oxymethyl]benzimidazol-5-yl-carboxylic acid-N-phenyl-N-(hydroxycarbonylmethyl)amide;

D is 1-methyl-2-[N-(4-amidinophenyl)aminomethyl]benzimidazol-5-yl-carboxylic acid-N-phenyl-N-(2-hydroxycarbonylethyl)amide;

E is 1-methyl-2-[N-(4-amidinophenyl)aminomethyl]benzimidazol-5-yl-carboxylic acid-N-(2-pyridyl)-N-(hydroxycarbonylmethyl)amide;

F is 1-methyl-2-[2-(4-amidinophenyl)ethyl]benzimidazol-5-yl-carboxylic acid-N-phenyl-N-[2-(1H-tetrazol-5-yl)ethyl]amide; and G is 1-methyl-2-[N-(4-amidinophenyl)aminomethyl]benzimidazol-5-yl-carboxylic acid-N-(2-pyridyl)-N-(2-hydroxycarbonylethyl)amide, were investigated as follows for their effects on thrombin time:

Materials: plasma, from human citrated blood.
  Test thrombin (bovine), 30U/mL, Behring Werke, Marburg
  Diethylbarbiturate acetate buffer, ORWH 60/61, Behring Werke, Marburg
  Biomatic B10 coagulometer, Sarstedt
Method:

The thrombin time was determined using a Biomatic B10 coagulometer made by Messrs. Sarstedt. As the test substance, 0.1 mL of human citrated plasma and 0.1 mL diethylbarbiturate buffer (DBA buffer) were added to the test strip prescribed by the manufacturer. The mixture was incubated for one minute at 37° C. The clotting reaction was started by the addition of 0.3 U test thrombin in 0.1 mL DBA buffer. The time is measured using the apparatus from the addition of the thrombin up to the clotting of the mixture. Mixtures to which 0.1 mL of DBA buffer were added were used as the controls.

According to the definition, a dosage-activity curve was used to determine the effective concentration of the substance, i.e., the concentration at which the thrombin time is double compared with the control.

The Table which follows contains the results found:

| Substance | Thrombin time (ED$_{200}$ in $\mu$M) |
|---|---|
| A | 0.04 |
| B | 0.06 |
| C | 0.15 |
| D | 0.03 |
| E | 0.09 |
| F | 0.03 |
| G | 0.03 |

By way of example, no acute toxic side effects were observed when compounds A, D, E, and G were administered to rats in doses of up to 10 mg/kg i.v. The compounds are thus well tolerated.

In view of their pharmacological properties, the new compounds and the physiologically acceptable salts thereof are suitable for the prevention and treatment of venous and arterial thrombotic diseases, such as for example the treatment of deep leg vein thrombosis, for preventing reocclusions after bypass operations or angioplasty (PT(C)A), and occlusion in peripheral arterial diseases such as pulmonary embolism, disseminated intravascular coagulation, for preventing coronary thrombosis, stroke and the occlusion of shunts or stents. In addition, the compounds according to the invention are suitable for antithrombotic support in thrombolytic treatment, such as for example with rt-PA or streptokinase, for preventing long-term restenosis after PT(C)A, for preventing metastasis and the growth of clot-dependent tumors and fibrin-dependent inflammatory processes.

The dosage required to achieve such an effect is appropriately 0.1 to 30 mg/kg, preferably 0.3 to 10 mg/kg by intravenous route, and 0.1 to 50 mg/kg, preferably 0.3 to 30 mg/kg by oral route, in each case administered 1 to 4 times a day. For this purpose, the compounds of formula I prepared according to the invention may be formulated, optionally together with other active substances, with one or more inert conventional carriers and/or diluents, e.g., with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, cetylstearyl alcohol, carboxymethylcellulose or fatty substances such as hard fat or suitable mixtures thereof, to produce conventional galenic preparations such as plain or coated tablets, capsules, powders, suspensions, or suppositories.

The Examples which follow are intended to illustrate the invention:
Preliminary Remarks Unless otherwise specified, the $R_f$ values were always determined using polygram silica gel plates produced by Messrs. E. Merck of Darmstadt. The EKA mass spectra (electrospray mass spectra of cations) are described, for example, in "Chemie unserer Zeit" 6, 308–316 (1991).

EXAMPLE 1

3-Methyl-2-[2-(4-amidinophenyl)ethyl]imidazo[4,5-b]pyridine-6-carboxylic acid-N-phenyl-N-(2-ethoxycarboxylethyl)amide a) Methyl 6-methylamino-5-nitronicotinate 1.6 g (7.4 mmol) of methyl 6-chloro-5-nitronicotinate (see Bernie et al., J. Chem. Soc. 1951, 2590) were stirred in 20 mL of 40% aqueous methylamine solution at room temperature for 30 minutes. The reaction mixture was then diluted with ice water, the yellow precipitate formed was filtered off and dried. Yield: 1.2 g (80% of theory); $R_f$ value: 0.66 (silica gel; ethyl acetate/ethanol/glacial acetic acid=90:5:5).

b) Methyl 5-amino-6-methylaminonicotinate

To a solution of 3.1 g (15 mmol) of methyl 6-methylamino-5-nitronicotinate in 100 mL of ethanol/dichloromethane (3:1) was added 1 g of palladium on charcoal (10%) and the resulting suspension was hydrogenated at room temperature under 5 bar of hydrogen pressure for 1.5 hours. The catalyst was then filtered off and the solvent was distilled off in vacuo. The crude oily product obtained was further reacted directly. Yield: 2.4 g (92% of theory); $R_f$ value: 0.44 (silica gel; ethyl acetate/ethanol/ammonia=90:10:1).

c) Methyl 5-[2-(4-cyanophenyl)ethylcarbonylamino]-6-methylaminonicotinate

A solution of 2.6 g (15 mmol) of 3-(4-cyanophenyl) propionic acid in 25 mL of absolute tetrahydrofuran was mixed with 2.4 g (15 mmol) of N,N'-carbonyldiimidazole and stirred for 20 minutes at room temperature. Then the imidazolide was mixed with a solution of 2.3 g (13 mmol) of methyl 5-amino-6-methylaminonicotinate in 25 mL of dimethylformamide and heated for 3 hours to 100° C. After the removal of the solvent in vacuo, the crude product obtained was taken up in ethyl acetate, the organic phase was washed with water and after drying over sodium sulfate it was again freed from solvent. The residue obtained was purified by flash chromatography (silica gel; gradient: dichloromethane to dichloromethane/ethanol=19:1). Yield: 2.1 g (50% of theory) of beige solid; $R_f$ value: 0.54 (silica gel; ethyl acetate/ethanol/ammonia=90:10:1).

d) Methylyl 3-methyl-2-[2-(4-cyanophenyl)ethyl]imidazo[4,5-b]pyridine-6-carboxylate A solution of 2.0 g (5.9 mmol) of methyl 5-[2-(4-cyanophenyl)ethylcarbonylamino]-6-methylaminonicotinate in 50 mL glacial acetic acid was heated to 100° C. for one hour. After removal of the solvent, the residue was taken up in dichloromethane, washed with sodium hydrogen carbonate solution, dried with sodium sulfate, and the solvent was distilled off again. Yield: 1.7 g brown solid (89% of theory); $R_f$ value: 0.50 (silica gel; ethyl acetate/ethanol/ammonia=90:10:1).

e) 3-Methyl-2-[2-(4-cyanophenyl)ethyl]imidazo[4,5-b]pyridine-6-carboxylic acid

A solution of 3.2 g (10 mmol) of 3-methyl-2-[2-(4-cyanophenyl)ethyl]imidazo[4,5-b]pyridine-6-carboxylate in 150 mL methanol was mixed with a solution of 1.5 g lithium hydroxide in 20 mL water and stirred for 24 hours at room temperature. Then the mixture was diluted with 50 mL of water, the alcohol was distilled off and the aqueous phase was washed with ethyl acetate. After acidification with dilute hydrochloric acid, the mixture was extracted several times with dichloromethane/methanol (9:1), the organic phase was dried with sodium sulfate and the solvent was distilled off. Yield: 2.1 g beige solid (70% of theory); $R_f$ value: 0.38 (silica gel; ethyl acetate/ethanol/ammonia= 50:45:5).

f) 3-Methyl-2-[2-(4-cyanopbenylethyl]imidazo[4,5-b]pyridine-6-carboxylic acid-N-phenyl-N-(2-ethoxycarbonylethyl)amide A solution of 2.0 g (6.5 mmol) of 3-methyl-2-[2-(4-cyanophenyl)ethyl]imidazo[4,5-b]pyridine-6-carboxylic acid in 100 mL dichloromethane was mixed with 20 mL thionyl chloride and refluxed for 2 hours. After the liquid components had been distilled off, the crude product was taken up twice more in dichloromethane and the solvent was distilled off each time. The crude acid chloride thus obtained (2 g) was suspended in 100 mL of tetrahydrofuran and mixed with 1.2 g (6.5 mmol) of N-(2-ethoxycarbonylethyl) aniline. Then within 5 minutes 0.73 g (7.2 mmol) of triethylamine were added dropwise. After 1 hour's stirring, the solvent was distilled off in vacuo, the residue was taken up in ethyl acetate, the organic phase was washed with water and dried with sodium sulfate. After distillation of the solvent and flash chromatography (silica gel; dichloromethane to dichloromethane/ethanol=49:1), the desired compound was isolated as a brownish oil. Yield: 1.9 g (65% of theory); $R_f$ value: 0.44 (silica gel; ethyl acetate/ethanol/ammonia=90:10:1).

g) 3-Methyl-2-[2-(4-amidinophenyl)ethyl]imidazo[4,5-b]pyridine-6-carboxylic acid-N-phenyl-N-(2-ethoxycarbonylethyl)amide 1.8 g (3.7 mmol) of 3-methyl-2-[2-(4-cyanophenyl)ethyl]idazo[4,5-b]pyridine-6-carboxylic acid-N-phenyl-N-(2-ethoxycarbonylethyl)amide were stirred into 100 l of ethanol saturated with hydrogen chloride for 16 hours, first at 0° C. and then at room temperature, until no more starting material could be detected by thin layer chromatography. Then the solvent was distilled off, the oily residue was taken up in 50 mL of absolute ethanol and mixed with 3.6 g (37 mmol) of ammonium carbonate. After 4 hours, the solvent was distilled off in vacuo; the crude product obtained was purified by flash chromatography (silica gel; gradient: dichloromethane/ethanol 19:1 to 4:1) and evaporated down again. Yield: 1.6 g of beige solid (80% of theory); $R_f$ value: 0.30 (silica gel; ethyl acetate/ethanol/ammonia=90:5:5).

EXAMPLE 2

3-Methyl-2-[2-(4-amidinophenyl)ethyl]imidazo[4,5-b]pyridine-6-carboxylic acid-N-phenyl-N-(2-hydroxycarbonylethyl)amide A solution of 535 mg (1.0 mmol) of 3-methyl-2-[2-(4-amidinophenyl)ethyl]imidazo[4,5-b]pyridine-6-carboxylic acid-N-phenyl-N-(2-ethoxycarbonylethyl)amide in 10 mL ethanol was mixed with 5 mL of 2N sodium hydroxide solution and stirred for 2 hours at room temperature. Then the mixture was diluted with 10 mL water, the alcohol was distilled off, the aqueous phase was washed with 20 mL ethyl acetate and acidified with concentrated hydrochloric acid, whereupon the desired compound was precipitated in the form of white crystals. Yield: 375 mg (74% of theory), $C_{26}H_{26}N_6O_3$ (470.54); $R_f$ value: 0.23 (silica gel; ethyl acetate/ethanol/ammonia=90:5:5); mass spectrum: $(M+H)^+=471$.

EXAMPLE 3

3-Methyl-2-[2-(4-amidinophenyl)ethyl]imidazo[4,5-b]pyridin-6-yl-carboxylic acid-N-(2-pyridyl)-N-(2-methoxycarbonylethyl)amide hydrochloride Prepared analogously to Example 1 from 3-methyl-2-[2-(4-cyanophenyl)ethyl]imidazo[4,5-b]pyridin-6-yl-carboxylic acid-N-(2-pyridyl)-N-(2-methoxycarbonylethyl) amide, methanolic hydrochloric acid, methanol, and ammonium carbonate. Yield: 75% of theory, $C_{26}H_{27}N_7O_3$ (485.55); $R_f$ value: 0.31 (silica gel; ethyl acetate/ethanol/ammonia=50:45:5); EKA mass spectrum: $(M+H)^+=486$.

EXAMPLE 4

3-Methyl-2-[2-(4-amidinophenyl)ethyl]imidazo[4,5-b]pyridin-6-yl-carboxylic acid-N-phenyl-N-ethoxycarbonylmethylamide hydrochloride Prepared analogously to Example 1 from 3-methyl-2-[2-(4-cyanophenyl)ethyl]imidazo[4,5-b]pyridin-6-ylcarboxylic acid-N-phenyl-N-ethoxycarbonylmethylamide, ethanolic hydrochloric acid, ethanol, and ammonium carbonate. Yield: 84% of theory, $C_{27}H_{28}N_6O_3$ (484.56); $R_f$ value: 0.44 (silica gel; ethyl acetate/ethanol/ammonia= 50:45:5); EKA mass spectrum: $(M+H)^+=485$.

EXAMPLE 5

3-Methyl-2-[2-(4-amidinophenyl)ethyl]imidazo[4,5-b]pyridin-6-yl-carboxylic acid-N-phenyl-N-hydroxycarbonylmethylamide hydrochloride Prepared analogously to Example 2 from 3-methyl-2-[2-(4-amidinophenyl)ethyl]imidazo[4,5-b]pyridin-6-yl-carboxylic acid-N-phenyl-N-ethoxycarbonylmethylamide hydrochloride and sodium hydroxide solution. Yield: 85% of theory, $C_{25}H_{24}N_6O_3$ (456.51); $R_f$ value: 0.19 (silica gel; ethyl acetate/ethanol/ammonia=50:45:5); EKA mass spectrum: $(M+H)^+=457$.

EXAMPLE 6

2-[2-(4-amidinophenyl)ethyl]-3-methyl-6-(2-methoxycarbonyl-2,3-dihydroindol-1-yl-carbonyl)imidazo[4,5-b]pyridine hydrochloride Prepared analogously to Example 1 from 2-[2-(4-cyanophenyl)ethyl]-3-methyl-6-(2-methoxycarbonyl-2,3-dihydroindol-1-yl-carbonyl)imidazo[4,5-b]pyridine, methanolic hydrochloric acid, methanol, and ammonium carbonate. Yield: 20% of theory, $C_{27}H_{26}N_6O_3$ (482.54); $R_f$ value: 0.30 (silica gel; ethyl acetate/ethanol/ammonia= 50:45:5); EKA mass spectrum: $(M+H)^+=483$.

EXAMPLE 7

2-[2-(4-amidinophenyl)ethyl]-3-methyl-6-(2-carboxy-2,3-dihydroindol-1-yl-carbonyl)imidazo[4,5-b]pyridine hydrochloride Prepared analogously to Example 2 from 2-[2-(4-amidinophenyl)ethyl]-3-methyl-6-(2-methoxycarbonyl-2,3-dihydroindol-1-yl-carbonyl)imidazo[4,5-b]pyridine hydrochloride and sodium hydroxide solution. Yield: 90% of theory, $C_{26}H_{24}N_6O_3$ (468.52); $R_f$ value: 0.24 (silica gel; ethyl acetate/ethanol/ammonia=50:45:5); EKA mass spectrum: $(M+H)^+=469$; $(M+Na)^+=491$.

EXAMPLE 8

1-Methyl-2-[(4-amidinophenyl)oxymethyl]imidazo[4,5-b]pyridin-5-yl-carboxylic acid-N-(2-pyridyl)-N-(2-ethoxycarbonylethyl)amide a) 2-Amino-3-methylamino-6-methylpyridine 8.35 g (50 mmol) of 2-Methyl-5-methylamino-6-nitropyridine (Heterocycles 38, 529 (1994)) were dissolved in 300 l ethyl acetate and hydrogenated with 1.5 g Raney nickel for 3.5 hours at room temperature. Then the catalyst was filtered off and the filtrate was evaporated down. After crystallization of the resulting residue from petroleum ether, 5.75 g (84% of theory) were obtained as olive-green crystals. $C_7H_{11}N_3$ (137.20). Melting point: 112–113° C.

b) 1,5-Dimethyl-2-[(4-cyanophenyl)oxymethyl]imidazo[4,5-b]pyridine 11.4 g (63 mmol) of 4-cyanophenoxyacetic acid were dissolved in 200 mL of absolute tetrahydrofuran and mixed at room temperature with 10.2 g (63 mmol) of N,N'-carbonyldiimidazole. After 15 minutes at 60° C., 5.70 g (41.5 mmol) of 2-amino-3-methylamino-6-methylpyridine were added. After 2 hours at 60° C., the solvent was distilled off and the crystalline residue was mixed with water, washed with water, and dried. After crystallization from ethanol, 9.95 g (91% of theory) were obtained in the form of white crystals. $C16H_{14}N_4O$ (278.32). Mass spectrum: $M^+=278$.

c) 1,5-Dimethyl-2-[(4-cyanophenyl)oxymethyl]imidazo[4,5-b]pyridin-4-N-oxide 2.62 g (10 mmol) of 1,5-dimethyl-2-[(4-cyanophenyl)oxymethyl]imidazo[4,5-b]pyridine were suspended in 125 mL dichloromethane and mixed with 2.62 g (12.7 mmol) of m-chloroperbenzoic acid, whereupon a clear solution was obtained. After 2 hours at room temperature, the solvent was distilled off and the residue obtained was mixed with a sodium hydrogen carbonate solution. After 30 minutes, the white crystalline product obtained was suction filtered, washed with water, and dried at 40° C. Yield: 2.45 g (83% of theory), $C_{16}H_{14}N_4O_2$ (294.30); mass spectrum: $M^+=294$.

d) 1-Methyl-2-[(4-cyanophenyl)oxymethyl]-5-hydroxymethylimidazo[4,5-b]pyridine 2.40 g (8.2 mmol) of 1,5-dimethyl-2-[(4-cyanophenyl)oxymethyl]imidazo[4,5-b]pyridin-4-N-oxide were suspended in 75 mL dichloromethane and mixed with 2.4 mL of trifluoroacetic acid anhydride (16.9 mmol), whereupon a clear solution was obtained. After 16 hours at room temperature, the solvent was distilled off, the viscous residue obtained was taken up in 50 mL dichloromethane and covered with 50 mL of 2M sodium hydrogen carbonate solution. After 3 hours' vigorous stirring, the precipitate formed was suction filtered, washed with water, and dried at 40° C. Yield: 1.85 g white powder (78% of theory), $C_{16}H_{14}N_4O_2$ (294.30); melting point: 172° C.

e) 1-Methyl-2-[(4-cyanophenyl)oxymethyl]imidazo[4,5-b]pyridine-5-carbaldehyde 3.65 g (12.5 mmol) of 1-methyl-2-[(4-cyanophenyl)oxymethyl]-5-hydroxymethylimidazo[4,5-b]pyridine were dissolved in 500 mL of dichloromethane and mixed with 15.0 g of manganese dioxide. After 96 hours at room temperature, the mixture was filtered through kieselguhr and the solvent was distilled off. The filtrate obtained was evaporated down, the crystalline precipitate was triturated with ether, suction filtered, and dried. Yield: 3.05 g white powder (84% of theory), $C_{16}H_{12}N_4O_2$ (292.30); melting point: 231° C.–234° C.

f) 1-Methyl-2-[(4-cyanophenyl)oxymethyl]-5-carboxyimidazo[4,5-b]pyridine 1.25 g (4.3 mmol) of 1-methyl-2-[(4-cyanophenyl)oxymethyl]imidazo[4,5-b]pyridine-5-carbaldehyde were dissolved in 10 mL formic acid and mixed at 0° C. with 1.0 mL hydrogen peroxide (33% strength). After 12 hours at 4° C., the white precipitate formed was suction filtered, washed with water, and dried at 40° C. Yield: 0.81 g (61% of theory), $C_{16}H_{12}N_4O_3$ (308.7).

g) 1-Methyl-2-[(4-cyanophenyl)oxymethyl]imidazo[4,5-b]pyridin-5-yl-carboxlic acid-N-(2-pyridyl)-N-(2-methoxycarbonylethyl)amide 308 mg (1.0 mmol) of 1-methyl-2-[(4-cyanophenyl)oxymethyl]-5-carboxyimidazo[4,5-b]pyridine were suspended in 5 mL of dimethylformamide and mixed with 303 mg (3.0 mmol) of N-methylmorpholine and 321 mg (1.0 mmol) of O-(benzotriazol-1-yl)-N,N,N',N'-tetramethyluronium tetrafluoroborate. After 10 minutes at room temperature, a solution of 215 mg (1.2 mmol) of methyl N-(2-pyridyl)-3-aminopropionate in 2 mL of dimethylformamide was added, whereupon a clear solution was obtained. After 12 hours at room temperature, the reaction solution was stirred into ice-water. After extracting 3 times with ethyl acetate, the combined organic extracts were washed with a saline solution, dried over sodium sulfate, and evaporated down. The residue obtained was chromatographed on silica gel with dichloromethane/ethanol (90:1 to 25:1). Yield: 165 mg of white powder (35% of theory), $C_{25}H_{12}N_6O_4$ (407.50); melting point: 139° C.–140° C.

h) 1-Methyl-2-[(4-amidinophenyl)oxymethyl]imidazo[4,5-b]pyridin-5-yl-carboxylic acid-N-(2-pyridyl)-N-(2-ethoxycarbonylethyl)amide Prepared by reacting 140 mg (0.3 mmol) of 1-methyl-2-[(4-cyanophenyl)oxymethyl]imidazo[4,5-b]pyridin-5-yl-carboxylic acid-N-(2-pyridyl)-N-(2-methoxycarbonylethyl)amide with ethanol saturated by hydrogen chloride and with ammonium carbonate/ethanol analogously to Example 1g. The resulting product was purified by chromatography over silica gel with dichloromethane/ethanol (19:1 to 4:1). Yield: 48 mg of white powder (36% of theory), $C_{26}H_{27}N_7O_4$ (501.57); mass spectrum: $(M+H)^+$=502.

EXAMPLE 9

2-[N-(4-amidinophenyl)aminomethyl]benzothiazole-5-carboxylic acid-N-phenyl-N-(2-ethoxycarbonylethyl)amide a) Ethyl 4-fluoro-3-methoxyacetamidobenzoate A solution of 2.8 g (15.3 mmol) of ethyl 3-amino-4-fluorobenzoate (cf L. S. Fosdick and A. F. Dodds in J. Amer. Chem. Soc. 65, 2305 (1943)) and 1.56 mL (1.85 g=17.0 mmol) of methoxyacetylchloride in 50 mL chlorobenzene was stirred for 1 hour at 50° C. and then refluxed for 15 minutes. Then the solvent was distilled off in vacuo and the crude product obtained was purified by flash chromatography (silica gel; dichloromethane/ethanol=100:1). The desired compound, initially oily, solidified within a few days. Yield: 3.8 g (98% of theory); $R_f$ value: 0.38 (silica gel; dichloromethane/ethanol=19:1).

b) Ethyl-2-methoxymethylbenzothiazole-5-carboxylate

A mixture of 3.0 g (11.7 mmol) of 4-fluoro-3-methoxyacetamidobenzoic acid and 2.1 g (5.2 mmol) of Lawesson's reagent was refluxed for 6 hours in 90 mL toluene, mixed with 1.0 g Lawesson's reagent and heated to 120° C. for another 6 hours. After the solvent was replaced with xylene, the mixture was heated to 180° C. for a further 8 hours in a pressurised vessel. Then the solvent was distilled off in vacuo, the crude product obtained was purified by flash chromatography (silica gel; ethyl acetate/petroleum ether=5:95), and evaporated down again. Yield: 2.1 g of yellow crystals (72% of theory); $R_f$ value: 0.55 (silica gel; ethyl acetate/petroleum ether=3:7).

c) 2-Methoxymethylbenzothiazole-5-carboxylic acid

A mixture of 2.1 g (8.36 mmol) of ethyl 2-methoxymethylbenzothiazole-5-carboxylate and 16 mL of 2N sodium hydroxide solution was stirred into 60 mL ethanol for 1 hour at room temperature. Then the alcohol was distilled off, the crude product was taken up in 20 mL water, washed with 50 mL diethylether, and the aqueous phase was acidified with concentrated hydrochloric acid while being cooled with ice. The pinkish-beige compound thereby precipitated was suction filtered, washed with water, and dried. Yield: 1.6 g (86% of theory); $R_f$ value: 0.12 (silica gel; dichloromethane/ethanol=29:1).

d) 2-Methoxymethylbenzothiazole-5-carboxylic acid-N-phenyl-N-(2-ethoxycarbonylethyl)amide A suspension of 1.6 g (7.2 mmol) of 2-methoxymethylbenzothiazole-5-carboxylic acid in 60 mL dichloromethane was mixed with 1.6 mL (22 mmol) of thionyl chloride and refluxed for 1 hour. The solid dissolved after 20 minutes. After distillation of the liquid components, the crude product was taken up in dichloromethane twice more and each time the solvent was distilled off. The crude acid chloride thus obtained was taken up in 50 mL of tetrahydrofuran, added dropwise to a mixture of 1.4 g (7.2 mmol) of N-(2-ethoxycarbonylethyl)aniline and 3.0 mL (21 mmol) of triethylamine in 50 mL of tetrahydrofuran and stirred overnight at room temperature. Then the solvent was distilled off in vacuo, the residue was taken up in 30 mL of dichloromethane, this solution was washed with water, and dried with sodium sulfate. After distillation of the solvent and flash chromatography (silica gel; gradient: dichloromethane/ethanol 98.5:1.5 to 80:20), the desired compound was isolated as a brownish oil. Yield: 2.05 (72% of theory); $R_f$ value: 0.40 (silica gel; ethyl acetate/petroleum ether=1:1).

e) 2-[N-(4-Cyanophenyl)aminomethyl]benzothiazole-5-carboxylic acid-N-phenyl-N-(2-ethoxycarbonylethyl)amide A mixture of 2.05 g (5.14 mmol) of 2-methoxymethylbenzothiazole-5-carboxylic acid-N-phenyl-N-(2-ethoxycarbonylethyl)amide and 5.7 mL (5.7 mmol) of a 1M solution of boron tribromide in dichloromethane was dissolved in a further 60 mL of dichloromethane and stirred for 16 hours at room temperature. Then the mixture was washed with 40 mL of saturated sodium hydrogen carbonate solution, the organic phase was dried with sodium sulfate, and the solvent was distilled off. The crude 2-bromomethylbenzothiazole-5-carboxylic acid-N-phenyl-N-(2-ethoxycarbonylethyl)amide thus obtained (2.4 g) was taken up in 5.0 mL of N,N-diisopropylethylamine and mixed with 0.64 g (5.4 mmol) of 4-aminobenzonitrile. After 1 hour's heating to 130° C., the solvent was distilled off in vacuo and the crude product obtained was purified by flash chromatography (silica gel; gradient: ethyl acetate/petroleum ether=1:3 to 1:1), whilst an orange foam was obtained when the eluates were evaporated down. Yield: 1.1 g (44% of theory); $R_f$ value: 0.35 (silica gel; ethyl acetate/petroleum ether=7:3).

f) 2-[N-(4-amidinophenyl)aminomethyl]benzothiazole-5-carboxylic acid-N-phenyl-N-(2-ethoxycarbonylethyl)amide 1.1 g (2.27 mmol) of 2-[N-(4-cyanophenyl)aminomethyl] benzothiazole-5-carboxylic acid-N-phenyl-N-(2-ethoxycarbonylethyl)amide was stirred in 100 mL of ethanol saturated with hydrogen chloride for 5 hours, first at 0° C. and then at room temperature, until no more starting material could be detected by thin layer chromatography. Then the solvent was distilled off at a maximum bath temperature of 30° C. and the oily residue was taken up in 100 mL of absolute ethanol and mixed with 1.6 g (22 mmol) of ammonium carbonate. After 18 hours stirring at room temperature, the solvent was distilled off in vacuo and the crude product was purified by flash chromatography (silica gel; gradient: water/methanol=19:1 to 4:1). When the eluates are evaporated down the desired compound is obtained as a white foam. Yield: 0.77 g (63% of theory), $C_{27}H_{27}N_5O_3S$ (501.60); $R_f$ value: 0.19 (silica gel; dichloromethane/ethanol=3:7); mass spectrum: $(M+H)^+$=502.

EXAMPLE 10

2-[N-(4-amidinophenyl)aminomethyl]benzothiazole-5-carboxylic acid-N-phenyl-N-(2-carboxyethyl)amide 0.45 g (0.84 mmol) of 2-[N-(4-amidinophenyl) aminomethyl]benzothiazole-5-carboxylic acid-N-phenyl-N-(2-ethoxycarbonylethyl)amide were dissolved in 15 mL of ethanol, mixed with 2 mL of 2N sodium hydroxide solution, and stirred for 4 hours at room temperature. Then the mixture was acidified with 3 mL of 2N hydrochloric acid and the solvent was distilled off. The crude product obtained was taken up in 5 mL dichloromethane/ethanol (2:1) and filtered to remove the insoluble sodium chloride. After the distillation of the solvent, the desired compound was obtained as a yellow foam. Yield: 0.26 g (67% of theory), $C_{25}H_{23}N_5O_3S$ (473.55); $R_f$ value: 0.47 (silica gel; methanol/5% aqueous sodium chloride=6:4); mass spectrum: $(M+H)^+=474$.

EXAMPLE 11

2-[N-(4-amidinophenyl)aminomethyl]benzothiazol-5-yl-carboxylic acid-N-(2-pyridyl)-N-(2-methoxycarbonylethyl)amide dihydrochloride Prepared analogously to Example 9 from 2-[N-(4-cyanophenyl)aminomethyl]benzothiazol-5-yl-carboxylic acid-N-(2-pyridyl)-N-(2-methoxycarbonylethyl)amide, methanolic hydrochloric acid, methanol, and ammonium carbonate. Yield: 68% of theory, $C_{25}H_{24}N_6O_3S$ (488.57); $R_f$ value: 0.13 (silica gel; methylene chloride/ethanol=4:1+a few drops of acetic acid); EKA mass spectrum: $(M+H)^+=489$.

EXAMPLE 12

2-[2-(4-amidinophenyl)ethyl]benzothiazol-5-yl-carboxylic acid-N-(2-pyridyl)-N-(ethoxycarbonylmethyl)amide dihydrochloride Prepared analogously to Example 9 from 2-[2-(4-cyanophenyl)ethyl]benzothiazol-5-yl-carboxylic acid-N-(2-pyridyl)-N-(ethoxycarbonylmethyl)amide, ethanolic hydrochloric acid, ethanol, and ammonium carbonate. Yield: 95% of theory, $C_{26}H_{25}N_5O_3S$ (487.58); $R_f$ value: 0.20 (silica gel; methylene chloride/ethanol=4:1+a few drops of acetic acid); EKA mass spectrum: $(M+H)^+=488$.

EXAMPLE 13

2-[N-(4-amidinophenyl)aminomethyl]benzothiazol-5-yl-carboxylic acid-N-(2-pyridyl)-N-(ethoxycarbonylmethyl)amide dihydrochloride Prepared analogously to Example 9 from 2-[N-(4-cyanophenyl)aminomethyl]benzothiazol-5-yl-carboxylic acid-N-(2-pyridyl)-N-(ethoxycarbonylmethyl)amide, ethanolic hydrochloric acid, ethanol, and ammonium carbonate. Yield: 68% of theory, $C_{25}H_{24}N_6O_3S$ (488.57); $R_f$ value: 0.14 (silica gel; methylene chloride/ethanol=4:1+a few drops of acetic acid); EKA mass spectrum: $(M+H)^+=489$.

EXAMPLE 14

2-[N-(4-amidinophenyl)aminomethyl]benzothiazol-5-yl-carboxylic acid-N-(2-pyridyl)-N-(hydroxycarbonylmethyl) amide dihydrochloride Prepared analogously to Example 10 from 2-[N-(4-amidinophenyl)aminomethyl]benzothiazol-5-yl-carboxylic acid-N-(2-pyridyl)-N-(ethoxycarbonylmethyl)amide dihydrochloride and sodium hydroxide solution. Yield: 90% of theory, $C_{23}H_{20}N_6O_3S$ (460.52); EKA mass spectrum: $(M+H)^+=461$; $(M+Na)^+=483$; $(M+2Na)^{++}=253$.

EXAMPLE 15

2-[N-(4-amidinophenyl)-N-methylaminomethyl]benzothiazol-5-yl-carboxylic acid-N-phenyl-N-(2-ethoxycarbonylethyl)amide hydrochloride
a) 2-[N-(4-Cyanophenyl)-N-methylaminomethyl]benzothiazol-5-yl-carboxylic acid-N-phenyl-N-(2-ethoxycarbonylethyl)amide Prepared analogously to Example 9e from 4-cyano-N-methylaniline and 2-methoxymethylbenzothiazole-5-carboxylic acid-N-phenyl-N-(2-ethoxycarbonylethyl)amide. Yield: 57% of theory; $R_f$ value: 0.46 (silica gel; dichloromethane/ethanol=19:1).
b) 2-[N-(4-amidinophenyl)-N-methylaminomethyl]benzothiazol-5-yl-carboxylic acid-N-phenyl-N-(2-ethoxycarbonylethyl)amide hydrochloride Prepared analogously to Example 9 from 2-[N-(4-cyanophenyl)-N-me-thylaminomethyl]benzothiazol-5-yl-carboxylic acid-N-phenyl-N-(2-ethoxycarbonylethyl)amide, ethanolic hydrochloric acid, ethanol, and ammonium carbonate. Yield: 73% of theory, $C_{28}H_{29}N_5O_3S$ (515.64); $R_f$ value: 0.29 (silica gel; methylene chloride/ethanol=4:1+a few drops of acetic acid); EKA mass spectrum: $(M+H)^+=516$.

EXAMPLE 16

2-[N-(4-amidinophenyl)-N-methylaminomethyl]benzothiazol-5-yl-carboxyiic acid-N-phenyl-N-(2-hydroxycarbonylethyl)amide hydrochloride Prepared analogously to Example 10 from 2-[N-(4-amidinophenyl)-N-methylaminomethyl]benzothiazol-5-yl-carboxylic acid-N-phenyl-N-(2-ethoxycarbonylethyl)amide hydrochloride and sodium hydroxide solution. Yield: 96% of theory, $C_{26}H_{25}N_5O_3S$ (487.58); $R_f$ value: 0.48 (Merck RP-8, methanol/5% NaCl solution=6:4); EKA mass spectrum: $(M+H)^+=488$; $(M+2Na)^{++}=266.5$.

EXAMPLE 17

2-[(4-amidinophenyl)thiomethyl]benzothiazol-5-yl-carboxylic acid-N-phenyl-N-(2-ethoxycarbonylethyl)amide hydrochloride Prepared analogously to Example 9 from 2-[(4-cyanophenyl)thiomethyl]benzothiazol-5-yl-carboxylic acid-N-phenyl-N-(2-ethoxycarbonylethyl)amide, ethanolic hydrochloric acid, ethanol, and ammonium carbonate. Yield: 61% of theory, $C_{27}H_{26}N_4O_3S_2$ (518.66); $R_f$ value: 0.27 (silica gel; methylene chloride/ethanol=4:1+a few drops of acetic acid); EKA mass spectrum: $(M+H)^+=519$.

EXAMPLE 18

2-[(4-amidinophenylthiomethyl]benzothiazol-5-yl-carboxylic acid-N-phenyl-N-(2-hydroxycarbonylethyl)amide hydrochloride Prepared analogously to Example 10 from 2-[(4-amidinophenyl)thiomethyl]benzothiazol-5-yl-carboxylic acid-N-phenyl-N-(2-ethoxycarbonylethyl)amide hydrochloride and sodium hydroxide solution. Yield: 95% of theory, $C_{25}H_{22}N_4O_3S_2$ (490.61); $R_f$ value: 0.25 (Merck RP-8, methanol/5% NaCl solution=6:4); EKA mass spectrum: $(M+H)^+=491$; $(M+Na)^+=513$.

EXAMPLE 19

2-[N-(4-amidinophenyl)aminomethyl]benzothiazol-5-yl-carboxylic acid-N-phenyl-N-(ethoxycarbonylmethyl)amide hydrochloride Prepared analogously to Example 9 from 2-[N-(4-cyanophenyl)aminomethyl]benzothiazol-5-yl-carboxylic acid-N-phenyl-N-(ethoxycarbonylmethyl)amide, ethanolic hydrochloric acid, ethanol, and ammonium carbonate. Yield: 82% of theory, $C_{26}H_{25}N_5O_3S$ (487.58); $R_f$ value: 0.21 (silica gel; methylene chloride/ethanol=4:1+a few drops of acetic acid); EKA mass spectrum: (M+H)$^+$=488.

EXAMPLE 20

2-[N-(4-amidinophenyl)aminomethyl]benzothiazol-5-yl-carboxylic acid-N-phenyl-N-(hydroxycarbonylmethyl)amide hydrochloride Prepared analogously to Example 10 from 2-[N-(4-amidinophenyl)aminomethyl]benzothiazol-5-yl-carboxylic acid-N-phenyl-N-(ethoxycarbonylmethyl)amide hydrochloride and sodium hydroxide solution. Yield: 75% of theory, $C_{24}H_{21}N_5O_3S$ (459.53); $R_f$ value: 0.14 (silica gel; methylene chloride/ethanol=4:1+a few drops of acetic acid); EKA mass spectrum: (M+H)$^+$=460; (M+Na)$^+$=482.

EXAMPLE 21

2-[2-(4-amidinophenyl)ethyl]benzothiazol-5-yl-carboxylic acid-N-phenyl-N-(2-ethoxycarbonylethyl)amide hydrochloride Prepared analogously to Example 9 from 2-[2-(4-cyanophenyl)ethyl]benzothiazol-5-yl-carboxylic acid-N-phenyl-N-(2-ethoxycarbonylethyl)amide, ethanolic hydrochloric acid, ethanol, and ammonium carbonate. Yield: 80% of theory, $C_{28}H_{28}N_4O_3S$ (500.62); $R_f$ value: 0.30 (silica gel; methylene chloride/ethanol=4:1+a few drops of acetic acid); EKA mass spectrum: (M+H)$^+$=501.

EXAMPLE 22

2-[2-(4-amidinophenyl)ethyl]benzothiazol-5-yl-carboxylic acid-N-phenyl-N-(2-hydroxycarbonylethyl)amide hydrochloride Prepared analogously to Example 10 from 2-[2-(4-amidinophenyl)ethyl]benzothiazol-5-yl-carboxylic acid-N-phenyl-N-(2-ethoxycarbonylethyl)amide hydrochloride and sodium hydroxide solution. Yield: 77% of theory, $C_{26}H_{24}N_4O_3S$ (472.57); $R_f$ value: 0.18 (silica gel; methylene chloride/ethanol=4:1+a few drops of acetic acid); EKA mass spectrum: (M+H)$^+$=473; (M+Na)$^+$=495; (M+H+Na)$^{++}$=259.

EXAMPLE 23

2-[N-(4-amidinophenyl)aminomethyl]benzothiazol-5-yl-carboxylic acid-N-(n-propyl)-N-(2-ethoxycarbonylethyl)amide hydrochloride Prepared analogously to Example 9 from 2-[N-(4-cyanophenyl)aminomethyl]benzothiazol-5-yl-carboxylic acid-N-(n-propyl)-N-(2-ethoxycarbonylethyl)amide, ethanolic hydrochloric acid, ethanol, and ammonium carbonate. Yield: 83% of theory, $C_{24}H_{29}N_5O_3$ (467.59); $R_f$ value: 0.31 (silica gel; methylene chloride/ethanol=4:1+a few drops of acetic acid); EKA mass spectrum: (M+H)$^+$=468; (2M+H)$^+$=935.

EXAMPLE 24

2-[N-(4-amidinophenyl)aminomethyl]benzothiazol-5-yl-carboxylic acid-N-(n-propyl)-N-(2-hydroxycarbonylethyl)amide hydrochloride Prepared analogously to Example 10 from 2-[N-(4-amidinophenyl)aminomethyl]benzothiazol-5-yl-carboxylic acid-N-(n-propyl)-N-(2-ethoxycarbonylethyl)amide hydrochloride and sodium hydroxide solution. Yield: 75% of theory, $C_{22}H_{25}N_5O_3S$ (439.54); $R_f$ value: 0.14 (silica gel; methylene chloride/ethanol=4:1+a few drops of acetic acid); EKA mass spectrum: (M+H)$^+$=440; (M+H+Na)$^{++}$=231.6.

EXAMPLE 25

1-Methyl-2-[N-(4-amidinophenyl)aminomethyl]benzimidazol-5-yl-carboxylic acid-N-phenyl-N-(2-ethoxycarbonylethyl)amide hydrochloride a) 4-Methylamino-3-nitrobenzoic acid-N-phenyl-N-(2-ethoxycarbonylethyl)amide To a solution of 24.7 g (0.115 mol) of 4-methylamino-3-nitrobenzoic acid chloride and 22.3 g (0.115 mol) of N-(2-ethoxycarbonylethyl)aniline in 300 mL of tetrahydrofuran, 13.1 g (0.13 mol) of triethylamine were added dropwise in 15 minutes, with stirring, at room temperature. After 2 hours stirring, the solvent was distilled off in a water-jet vacuum and the residue was mixed with 700 mL of water with stirring. The mixture was extracted 3 times with 200 mL of dichloromethane, the organic extract was washed twice with 200 mL of 2N hydrochloric acid and twice with 300 mL of water and dried over sodium sulfate. The solvent was then distilled off and the oily product thus obtained was purified by column chromatography (1 kg silica gel; eluant: petroleum ether/ethyl acetate=2:1). Yield: 35.0 g (82% of theory); $R_f$ value: 0.28 (silica gel; dichloromethane/ethanol=50:1).

b) 3-Amino-4-methylaminobenzoic acid-N-phenyl-N-(2-ethoxycarbonylethyl)amide 12.1 g (0.0326 mol) of 4-methylamino-3-nitrobenzoic acid-N-phenyl-N-(2-ethoxycarbonylethyl)amide were hydrogenated in 300 mL ethanol and 150 mL dichloromethane after the addition of about 4 g of palladium/charcoal (10%) at room temperature and under a hydrogen pressure of 5 bar. Then the catalyst was filtered off and the filtrate was evaporated down. The crude product thus obtained was reacted without further purification. Yield: 10.6 g (95% of theory); $R_f$ value: 0.19 (silica gel; dichloromethane/ethanol=50:1).

c) 1-Methyl-2-[N-(4-cyanophenyl)aminomethyl]benzimidazol-5-yl-carboxylic acid-N-phenyl-N-(2-ethoxycarbonylethyl)amide 6.17 g (0.035 mol) of N-(4-cyanophenyl)glycine and 5.68 g (0.035 mol) of N,N'-carbonyldiimidazole were refluxed in 300 mL of tetrahydrofuran for 30 minutes, then 10.6 g (0.032 mol) of 3-amino-4-methylaminobenzoic acid-N-phenyl-N-(2-ethoxycarbonylethyl)amide were added, and the mixture was refluxed for a further five hours. Then the solvent was distilled off in vacuo, the residue was dissolved in 150 mL of glacial acetic acid and refluxed for one hour. Then the glacial acetic acid was distilled off in vacuo, the residue was dissolved in about 300 mL of dichloromethane, the solution was washed twice with about 150 mL water and then dried over sodium sulfate. After evaporation of the solvent, the crude product thus obtained was purified by column chromatography (800 g silica gel; eluant: dichloromethane with 1–2% ethanol). Yield: 8.5 g (57% of theory); $R_f$ value: 0.51 (silica gel; dichloromethane/ethanol=19:1).

d) 1-Methyl-2-[N-(4-amidinophenl)aminomethyl]benzimidazol-5-yl-carboxylic acid-N-phenyl-N-(2-ethoxycarbonylethyl)amide hydrochloride 1.2 g (2.49 mmol) of 1-methyl-2-[N-(4-cyanophenyl)aminomethyl]benzimidazol-5-yl-carboxylic acid-N-phenyl-N-(2-ethoxycarbonylethyl)amide were stirred in 100 mL of saturated ethanolic hydrochloric acid for 6 hours at room temperature. Then the mixture was evaporated to dryness in vacuo, the residue was dissolved in 100 mL of ethanol, mixed with 2.5 g (26 mmol) of ammonium carbonate and stirred overnight at room temperature. After distillation of the solvent, the crude product thus obtained was purified by column chromatography (100 g silica gel; eluant: dichloromethane/ethanol=4:1). By concentrating the eluates the desired compound was obtained as a white, amorphous solid. Yield: 1.10 g (83% of theory), $C_{28}H_{30}N_6O_3 \times HCl$ (498.6); $R_f$ value: 0.18 (silica gel; dichloromethane/ethanol= 4:1); EKA mass spectrum: $(M+H)^+=499$; $(M+2H)^{++}=250$; $(M+H+Na)^{++}=261$.

EXAMPLE 26

1-Methyl-2-[N-(4-amidinophenyl)aminomethyl] benzimidazol-5-yl-carboxylic acid-N-phenyl-N-(2-hydroxycarbonylethyl)amide A mixture of 300 mg (0.56 mmol) of 1-methyl-2-[N-(4-amidinophenyl)aminomethyl]benzimidazol-5-yl-carboxylic acid-N-phenyl-N-(2-ethoxycarbonylethyl)amide hydrochloride, 15 mL of ethanol, 4 mL of water and 120 mg (3.0 mmol) of sodium hydroxide was stirred for two hours at room temperature. Then the mixture was diluted with about 20 mL of water and made weakly alkaline with glacial acetic acid. The product which crystallized out was suction filtered, washed with water, and dried at 60° C. in vacuo. Yield: 250 mg (95% of theory), $C_{26}H_{26}N_6O_3$ (470.5); EKA mass spectrum: $(M+H)^+=471$; $(M+H+Na)^{++}=247$; $(M+2Na)^{++}=258$.

EXAMPLE 27

1-Methyl-2-[(4-amidinophenyl)thiomethyl] benzimidazol-5-yl-carboxylic acid-N-(n-propyl)-N-(2-ethoxycarbonylethylamide hydrochloride a) 4-Methylamino-3-chloracetamidobenzoic acid-N-(n-propyl)-N-(2-ethoxycarbonylethyl)amide A solution of 1.8 g (5.9 mmol) of 3-amino-4-methylaminobenzoic acid-N-(n-propyl)-N-(2-ethoxycarbonylethyl)amide [prepared analogously to 3-amino-4-ethylaminobenzoic acid-N-phenyl-N-(2-ethoxycarbonylethyl)amide], 1.1 g (6.8 mmol) of N,N'-carbonyldiimidazole, and 0.65 g (6.9 mmol) of chloroacetic acid in 75 mL tetrahydrofuran was stirred for 1 hour at room temperature. Then the solvent was distilled off in vacuo, and the crude product was purified by flash chromatography (silica gel; methylene chloride/ethanol=49:1). Yield: 1.7 g (77% of theory) yellow oil; $R_f$ value: 0.58 (silica gel; ethyl acetate/ethanol/ammonia=90:10:1).

b) 2-Chloromethyl-1-methylbenzimidazol-5-yl-carboxylic acid-N-(n-propyl)-N-(2-ethoxycarbonylethyl)amide 1.6 g (4.3 mmol) of 4-methylamino-3-chloracetamidobenzoic acid-N-(n-propyl)-N-(2-ethoxycarbonylethyl)amide were heated to 100° C. in 25 mL of acetic acid for 30 minutes. Then the solvent was distilled off, the crude product was taken up in 40 mL methylene chloride/ethanol (9:1) and washed with 20 mL saturated sodium hydrogen carbonate solution. The organic phase was dried with sodium sulfate and evaporated down. Yield: 1.5 g (100% of theory) of brown oil; $R_f$ value: 0.63 (silica gel; ethyl acetate/ethanol/ammonia=90:10:1).

c) 1-Methyl-2-[(4-cyanophenyl)thiomethyl]benzimidazol-5-yl-carboxylic acid-N-(n-propyl)-N-(2-ethoxycarbonylethyl)amide A mixture of 1.5 g (4.1 mmol) of 2-chloromethyl-1-methylbenzimidazol-5-yl-carboxylic acid-N-(n-propyl)-N-(2-ethoxycarbonylethyl)amide and 0.65 g (4.8 mmol) of p-cyanothiophenol was heated in 10 mL of dimethylformamide and 10 mL of diisopropylethylamine for 1 hour to 100° C. The solvent was distilled off in vacuo, the crude product was dissolved in 30 mL ethyl acetate, washed with 30 mL water, and after concentration purified by flash chromatography (silica gel; methylene chloride/ethanol (49:1 to 19:1). Yield: 1.5 g (79% of theory) of brown oil; $R_f$ value: 0.65 (silica gel; ethyl acetate/ethanol/ammonia=90:10:1).

d) 1-Methyl-2-[(4-amidinophenyl)thiomethyl] benzimidazol-5-yl-carboxylic acid-N-(n-propyl)-N-(2-ethoxycarbonylethyl)amide hydrochloride 1.4 g (3.01 mmol) of 1-methyl-2-[(4-cyanophenyl) thiomethyl]benzimidazol-5-yl-carboxylic acid-N-(n-propyl)-N-(2-ethoxycarbonylethyl)amide were stirred in 50 mL of ethanol saturated with hydrogen chloride for 5 hours first at 0° C., later at room temperature, until no more starting material could be detected by thin layer chromatography. Then the solvent was distilled off at a maximum bath temperature of 30° C., the oily residue was taken up in 40 mL of absolute ethanol and mixed with 2.8 g of ammonium carbonate. After 18 hours, the solvent was distilled off in vacuo and the crude product was purified by flash chromatography (silica gel; methylene chloride/ethanol=19:1 to 4:1). Yield: 1.3 g (83% of theory) as a light beige solid, $C_{25}H_{31}N_6O_3S$ (481.62); $R_f$ value: 0.29 (silica gel; ethyl acetate/ethanol/ammonia=50:45:5); EKA mass spectrum: $(M+H)^+=482$.

EXAMPLE 28

1-Methyl-2-[(4-amidinophenylthiomethyl]benzimidazol-5-yl-carboxylic acid-N-(n-propyl)-N-(2-hydroxycarbonylethyl)amide hydrochloride 0.52 g (1.0 mmol) of 1-Methyl-2-[(4-amidinophenyl) thiomethyl]benzimidazol-5-yl-carboxylic acid-N-(n-propyl)-N-(2-ethoxycarbonylethyl)amide hydrochloride was dissolved in 15 mL ethanol, mixed with 5 mL of 2N sodium hydroxide solution and stirred for 2 hours at room temperature. Then 5 mL of water were added, the alcohol was distilled off, and it was acidified with concentrated hydrochloric acid. The water was distilled off in vacuo, and the crude product was taken up in 5 mL of ethanol and filtered to remove the insoluble sodium chloride. After the solvent had been distilled off, the title compound was obtained as a white solid. Yield: 0.43 g (88% of theory), $C_{23}H_{27}N_3O_3S$ (453.57); $R_f$ value: 0.19 (silica gel; ethyl acetate/ethanol/ammonia=50:45:5); EKA mass spectrum: $(M+H)^{+=}454$; $(M+Na)^+=476$.

EXAMPLE 29

1-Methyl-2-[(4-amidinophenyl)thiomethyl] benzimidazol-5-yl-carboxylic acid-N-(2-methylpropyl)-N-(2-ethoxycarbonylethyl)amide hydrochloride Prepared analogously to Example 27 from 1-methyl-2-[(4-cyanophenyl)thiomethyl]benzimidazol-5-yl-carboxylic acid-(N-(2-methylpropyl-N-(2-ethoxycarbonylethyl)amide, ethanolic hydrochloric acid, ethanol, and ammonium carbonate. Yield: 83% of theory, $C_{25}H_{31}N_6O_3S$ (495.65); $R_f$ value: 0.30 (silica gel; ethyl acetate/ethanol/ammonia= 50:45:5); EKA mass spectrum: $(M+H)^+=496$.

EXAMPLE 30

1-Methyl-2-[(4-amidinophenyl)thiomethyl] benzimidazol-5-yl-carboxlic acid-N-phenyl-N-(2-ethoxycarbonylethyl)amide hydrochloride Prepared analogously to Example 27 from 1-methyl-2-[(4-cyanophenyl)thiomethyl]benzimidazol-5-yl-carboxylic acid-N-phenyl-N-(2-ethoxycarbonylethyl)amide, and ethanolic hydrochloric acid, ethanol, and ammonium carbonate. Yield: 90% of theory, $C_{28}H_{29}N_5O_3S$ (515.64); $R_f$ value: 0.24 (silica gel; ethyl acetate/ethanol/ammonia=50:45:5); EKA mass spectrum: $(M+H)^+=516$; $(M+H+Na)^{++}=269.7$.

EXAMPLE 31

1-Methyl-2-[(4-amidinophenyl)thiomethyl]benzimidazol-5-yl-carboxylic acid-N-phenyl-N-(2-hydroxycarbonylethyl)amide hydrochloride Prepared analogously to Example 28 from 1-methyl-2-[(4-amidinophenyl)thiomethylbenzimidazol-5-yl-carboxylic acid-N-phenyl-N-(2-ethoxycarbonylethyl)amide hydrochloride and sodium hydroxide solution. Yield: 76% of theory, $C_{26}H_{25}N_5O_3S$ (487.58); $R_f$ value: 0.31 (silica gel; ethyl acetate/ethanol/ammonia=50:45:5); EKA mass spectrum: $(M+H)^+=488$; $(M+Na)^+=510$.

EXAMPLE 32

1-Methyl-2-[(4-amidinophenyl)oxymethyl]benzimidazol-5-yl-sulfonic acid-N-(1-methyl-piperidin-4-yl)-N-methylamide hydrochloride a) 4-Chloro-3-nitrobenzenesulfonic acid-N-(1-methylpiperidin-4-yl)-N-methylamide To a solution of 2.2 mL (15 mmol) of 1-methyl-4-methylaminopiperidine in 60 mL pyridine, 3.8 g (15 mmol) of 4-chloro-3-nitrobenzenesulfonic acid chloride were added, in batches, whilst cooling with ice. The mixture was then stirred for two hours with cooling, then evaporated to dryness, the residue was mixed with about 50 mL of water and made alkaline with concentrated ammonia whilst stirring vigorously. The crude product precipitated was suction filtered and purified by column chromatography (250 g silica gel, eluant: dichloromethane with 1.5% ethanol). Yield: 1.6 g (31% of theory), $C_{13}H_{18}ClN_3O_4S$ (347.8); $R_f$ value: 0.19 (silica gel; dichloromethane/ethanol=19:1).

b) 4-Methylamino-3-nitrobenzenesulfonic acid-N-methyl-N-(1-methylpiperidin-4-yl)amide 1.6 g (4.6 mmol) of 4-chloro-3-nitrobenzenesulfonic acid-N-methyl-N-(1-methylpiperidin-4-yl)amide was mixed with 30 mL of 40% methylamine solution and stirred in a sealed flask for four hours at room temperature. Then the mixture was diluted with about 40 mL of water, the product precipitated was suction filtered, washed with water, and dried. Yield: 1.5 g (95% of theory), $C_{14}H_{22}N_4O_4S$ (343.4); $R_f$ value: 0.45 (silica gel; dichloromethane/ethanol=4:1).

c) 3-Amino-4-methylaminobenzenesulfonic acid-N-methyl-N-(1-methylpiperidin-4-yl)amide 1.5 g (4.4 mmol) of 4-methylamino-3-nitrobenzenesulfonic acid-N-methyl-N-(1-methylpiperidin-4-yl)amide were dissolved in 100 mL methanol and catalytically hydrogenated at room temperature and under 5 bar hydrogen pressure (10% palladium on charcoal). Then the catalyst was filtered off and the filtrate was evaporated down. The resulting oily product was further reacted without any purification. Yield: 1.4 g (100% of theory), $C_{14}H_{24}N_4O_2S$ (312.4); $R_f$ value: 0.33 (silica gel; dichloromethane/ethanol=4:1).

d) 1-Methyl-2-[(4-cyanophenyl)oxymethyl]benzimidazol-5-yl-sulfonic acid-N-methyl-N-(1-methyl-piperidin-4-yl)amide 532 mg (3.0 mmol) of 4-cyanophenyloxyacetic acid and 486 mg (3.0 mmol) of 1,1'-carbonyldiimidazole were dissolved in 40 mL of tetrahydrofuran and refluxed for 15 minutes. Then 700 mg (2.24 mmol) of 3-amino-4-methylaminobenzenesulfonic acid-N-methyl-N-(1-methylpiperidin-4-yl)amide were added and boiling was continued for a further eight hours. Then the mixture was evaporated down and the resulting oily residue was refluxed in 30 mL of glacial acetic acid for one hour. The glacial acetic acid was distilled off, the residue was mixed with about 30 mL of water and made alkaline with concentrated ammonia, and the solution was extracted three times with about 20 mL of dichloromethane. The organic phases were dried and evaporated down. The resulting product was further reacted without any purification. Yield: 400 mg (39% of theory), $C_{23}H_{27}N_5O_3S$ (453.6); $R_f$ value: 0.37 (silica gel; dichloromethane/ethanol=4:1).

e) 1-Methyl-2-[(4-amidinophenyl)oxymethyl]benzimidazol-5-yl-sulfonic acid-N-methyl-N-(1-methylpiperidin-4-yl)amide hydrochloride Prepared analogously to Example 25d from 400 mg of 1-methyl-2-[(4-cyanophenyl)oxymethyl]benzimidazol-5-yl-sulfonic acid-N-methyl-N-(1-methylpiperidin-4-yl)amide with ethanolic hydrochloric acid and ammonium carbonate. Yield: 370 mg (83% of theory), $C_{23}H_{30}N_6O_3S$ (470.6); EKA mass spectrum: $(M+H)^+=471$; $(M+2H)^{++}=236$.

EXAMPLE 33

1-Methyl-2-[(4-amidinophenyl)oxymethyl]benzimidazol-5-yl-sulfonic acid-N-methyl-N-phenylamide hydrochloride Prepared analogously to Example 32 from 1-methyl-2-[(4-cyanophenyl)oxymethyl]benzimidazol-5-yl-sulfonic acid-N-methyl-N-phenylamide and ethanolic hydrochloric acid, ethanol, and ammonium carbonate. Yield: 46% of theory, $C_{23}H_{23}N_5O_3S$ (449.5); EKA mass spectrum: $(M+H)^+=450$; $(M+H+methanol)^+=482$; $(M+2H)^{++}=223$.

EXAMPLE 34

1-Methyl-2-[(4-amidinophenyl)oxymethyl]benzimidazol-5-yl-sulfonic acid-N-(3-ethoxycarbonyl-n-propyl)-N-phenylamide hydrochloride Prepared analogously to Example 32 from 1-methyl-2-[(4-cyanophenyl)oxymethyl]benzimidazol-5-yl-sulfonic acid-N-(3-ethoxycarbonyl-n-propyl)-N-phenylamide, ethanolic hydrochloric acid, ethanol, and ammonium carbonate. Yield: 57% of theory, $C_{28}H_{31}N_5O_5S$ (549.7); EKA mass spectrum: $(M+H)^+=550$.

EXAMPLE 35

1-Methyl-2-[(3-amidinophenyl)oxymethyl]benzimidazol-5-yl-sulfonic acid-pyrrolidide hydrochloride Prepared analogously to Example 32 from 1-methyl-2-[(3-cyanophenyl)oxymethyl]benzimidazol-5-yl-sulfonic acid-pyrrolidide, ethanolic hydrochloric acid, ethanol, and ammonium carbonate. Yield: 71% of theory, $C_{20}H_{23}N_5O_3S$ (413.5); EKA mass spectrum: $(M+H)^+=414$.

EXAMPLE 36

1-Methyl-2-[2-(4-amidinophenyl)ethyl]benzimidazol-5-yl-carboxylic acid-N-phenyl-N-(3-methoxycarbonylpropyl)amide dihydrochloride Prepared analogously to Example 25d from 1-methyl-2-[2-(4-cyanophenyl)ethyl]benzimidazol-5-yl-carboxylic acid-N-phenyl-N-(3-tert-butyloxycarbonylpropyl)amide and methanolic hydrochloric acid, methanol, and ammonium carbonate. Yield: 83.5% of theory, $C_{29}H_{31}N_5O_3$ (497.6); $R_f$ value: 0.17 (silica gel; dichloromethane/ethanol= 4:1); EKA mass spectrum: $(M+H)^+=498$; $(M+H+Na)^{++}=260.7$.

EXAMPLE 37

1-Methyl-2-[2-(4-amidinophenyl)ethyl] benzimidazol-5-yl-carboxylic acid-N-phenyl-N-(3-hydroxycarbonylpropyl)amide hydrochloride Prepared analogously to Example 26 from 1-methyl-2-[(4-amidinophenyl)aminomethyl]benzimidazol-5-yl-carboxylic acid-N-phenyl-N-(3-methoxycarbonylpropyl) amide dihydrochloride and sodium hydroxide solution. Yield: 92% of theory, $C_{28}H_{29}N_5O_3$ (483.6); $R_f$ value: 0.09 (silica gel; dichloromethane/ethanol=4:1); EKA mass spectrum: $(M+H)^+=484$; $(M+Na)^+=506$; $(M+H+Na)^{++}=253.7$.

EXAMPLE 38

1-Methyl-2-[N-(4-amidinophenyl)aminomethyl] benzimidazol-5-yl-carboxylic acid-N-phenyl-N-(3-ethoxycarbonylpropyl)amide dihydrochloride a) 1-Methyl-2-[N-(4-cyanophenyl)aminomethyl] benzimidazol-5-yl-carboxylic acid-N-phenyl-N-(3-tert-butyloxycarbonylpropyl)amide Prepared analogously to Example 25c from N-(4-cyanophenyl)glycine and 3-amino-4-methylaminobenzoic acid-N-phenyl-N-(3-tert-butyloxycarbonylpropyl)amide. Yield: 65% of theory; $R_f$ value: 0.17 (silica gel; dichloromethane/methanol=19:1).

b) 1-Methyl-2-[N-(4-amidinophenyl)aminomethyl] benzimidazol-5-yl-carboxylic acid-N-phenyl-N-(3-ethoxycarbonylpropyl)amide dihydrochloride Prepared analogously to Example 25d from 1-methyl-2-[N-(4-cyanophenyl)aminomethyl]benzimidazol-5-yl-carboxylic acid-N-phenyl-N-(3-tert-butyloxycarbonylpropyl)amide and ethanolic hydrochloric acid, ethanol, and ammonium carbonate. Yield: 68% of theory, $C_{29}H_{32}N_6O_3$ (512.6); $R_f$ value: 0.12 (silica gel; dichloromethane/ethanol=4:1); EKA mass spectrum: $(M+H)^+=513$; $(M+H+Na)^{++}=268$.

EXAMPLE 39

1-Methyl-2-[N-(4-amidinophenyl)aminomethyl] benzimidazol-5-yl-carboxylic acid-N-phenyl-N-(3-hydroxycarbonylpropyl)amide hydrochloride Prepared analogously to Example 26 from 1-methyl-2-[N-(4-amidinophenyl)aminomethyl]benzimidazol-5-yl-carboxylic acid-N-phenyl-N-(3-ethoxycarbonylpropyl) amide dihydrochloride and sodium hydroxide solution. Yield: 73.5% of theory, $C_{27}H_{28}N_6O_3$ (484.6); EKA mass spectrum: $(M+H)^+=485$; $(M+2H)^{++}=243$; $(M+H+Na)^{++}=254$.

EXAMPLE 40

1-Methyl-2-[2-(4-amidinophenyl)ethyl] benzimidazol-5-yl-carboxylic acid-N-phenyl-N-(ethoxycarbonylmethyl) amide hydrochloride Prepared analogously to Example 25d from 1-methyl-2-[2-(4-cyanophenyl)ethyl]benzimidazol-5-yl-carboxylic acid-N-phenyl-N-(ethoxycarbonylmethyl)amide and ethanolic hydrochloric acid, ethanol, and ammonium carbonate. Yield: 73% of theory, $C_{28}H_{29}N_5O_3$ (483.6); $R_f$ value: 0.15 (silica gel; dichloromethane/ethanol=4:1); EKA mass spectrum: $(M+H)^+=484$; $(M+H+Na)^{++}=253.7$.

EXAMPLE 41

1-Methyl-2-[2-(4-amidinophenyl)ethyl] benzimidazol-5-yl-carboxylic acid-N-phenyl-N-(hydroxycarbonylmethyl)amide hydrochloride Prepared analogously to Example 26 from 1-methyl-2-[2-(4-amidinophenyl)ethyl]benzimidazol-5-yl-carboxylic acid-N-phenyl-N-(ethoxycarbonylmethyl)amide hydrochloride and sodium hydroxide solution. Yield: 97% of theory, $C_{26}H_{25}N_5O_3$ (455.5); EKA mass spectrum: $(M+H)^+=456$; $(M+Na)^+=478$; $(M+2Na)^{++}=250.6$.

EXAMPLE 42

1-Methyl-2-[(4-amidinophenyloxymethyl] benzimidazol-5-yl-carboxylic acid-N-phenyl-N-(ethoxycarbonylmethyl)amide hydrochloride Prepared analogously to Example 25d from 1-methyl-2-[(4-cyanophenyl)oxymethyl]benzimidazol-5-yl-carboxylic acid-N-phenyl-N-(ethoxycarbonylmethyl)amide and ethanolic hydrochloric acid, ethanol, and ammonium carbonate. Yield: 76% of theory, $C_{27}H_{27}N_5O_4$ (485.6); $R_f$ value: 0.17 (silica gel; dichloromethane/ethanol=4:1); EKA mass spectrum: $(M+H)^+=486$; $(M+H+Na)^{++}=254.7$.

EXAMPLE 43

1-Methyl-2-[(4-amidinophenyl)oxymethyl] benzimidazol-5-yl-carboxylic acid-N-phenyl-N-(hydroxycarbonylmethyl) amide hydrochloride Prepared analogously to Example 26 from 1-methyl-2-[(4-amidinophenyl)oxymethyl]benzimidazol-5-yl-carboxylic acid-N-phenyl-N-(ethoxycarbonylmethyl)amide hydrochloride and sodium hydroxide solution. Yield: 58% of theory, $C_{25}H_{23}N_5O_4$ (457.5); EKA mass spectrum: $(M+H)^+=458$; $(M+Na)^+=480$; $(M+2Na)^{++}=251.6$.

EXAMPLE 44

1-Methyl-2-[N-(4-amidinophenyl)aminomethy)] benzimidazol-5-yl-carboxylic acid-N-phenyl-N-(ethoxycarbonylmethyl) amide hydrochloride Prepared analogously to Example 25d from 1-methyl-2-[N-(4-cyanophenyl)aminomethyl]benzimidazol-5-yl-carboxylic acid-N-phenyl-N-(ethoxycarbonylmethyl)amide and ethanolic hydrochloric acid, ethanol, and ammonium carbonate. Yield: 74% of theory, $C_{27}H_{28}N_6O_3$ (484.6); $R_f$ value: 0.12 (silica gel; dichloromethane/ethanol=4:1); EKA mass spectrum: $(M+H)^+=485$; $(M+H+Na)^{++}=254$.

EXAMPLE 45

1-Methyl-2-[N-(4-amidinophenyl)-aminomethyl] benzimidazol-5-yl-carboxylic acid-N-phenyl-N-(hydroxycarbonylmethyl)amide hydrochloride Prepared analogously to Example 26 from 1-methyl-2-[N-(4-amidinophenyl)aminomethyl]benzimidazol-5-yl-carboxylic acid-N-phenyl-N-(ethoxycarbonylmethyl)amide hydrochloride and sodium hydroxide solution. Yield: 84% of theory, $C_{25}H_{24}N_6O_3$ (456.5); EKA mass spectrum: $(M+H)^+=457$; $(M+Na)^+=479$; $(M+2Na)^{++}=251$.

EXAMPLE 46

1-Methyl-2-[(4-amidinophenyl)oxymethyl]
benzimidazol-5-yl-carboxylic acid-N-(4-pyrimidyl)-
N-(2-ethoxycarbonylethylamide hydrochloride Prepared analogously to Example 25d from 1-methyl-2-[(4-cyanophenyl)oxymethyl]benzimidazol-5-yl-carboxylic acid-N-(4-pyrimidyl)-N-(2-ethoxycarbonylethyl)amide and ethanolic hydrochloric acid, ethanol, and ammonium carbonate. Yield: 14% of theory, $C_{26}H_{27}N_7O_4$ (501.6); mass spectrum: $(M+H)^+=502$.

EXAMPLE 47

1-Methyl-2-[(4-amidinophenyl)oxymethyl]
benzimidazol-5-yl-carboxylic acid-N-(2-pyridyl)-N-
(ethoxycarbonylmethyl)amide dihydrochloride Prepared analogously to Example 25d from 1-methyl-2-[(4-cyanophenyl)oxymethyl]benzimidazol-5-yl-carboxylic acid-N-(2-pyridyl)-N-(ethoxycarbonylmethyl)amide and ethanolic hydrochloric acid, ethanol, and ammonium carbonate. Yield: 44% of theory, $C_{26}H_{26}N_6O_4$ (486.5); $R_f$ value: 0.12 (silica gel; dichloromethane/ethanol=4:1); EKA mass spectrum: $(M+H)^+=487$; $(M+2H)^{++}=244$; $(M+H+Na)^{++}=255$.

EXAMPLE 48

1-Methyl-2-[(4-amidinophenyl)oxymethyl]
benzimidazol-5-yl-carboxylic acid-N-(2-pyridyl)-N-
(hydroxycarbonylmethyl)amide hydrochloride Prepared analogously to Example 26 from 1-methyl-2-[(4-amidinophenyl)oxymethyl]benzimidazol-5-yl-carboxylic acid-N-(2-pyridyl)-N-(ethoxycarbonylmethyl)amide dihydrochloride and sodium hydroxide solution. Yield: 85% of theory, $C_{24}H_{22}N_6O_4$ (458.5); EKA mass spectrum: $(M+H)^+=459$; $(M+Na)^+=481$; $(M+2Na)^{++}=252$.

EXAMPLE 49

1-Methyl-2-[N-(4-amidinophenyl)aminomethyl]
benzimidazol-5-yl-carboxylic acid-N-(2-pyridyl-N-
(ethoxycarbonylmethyl)amide dihydrochloride a) 1-Methyl-2-[N-(4-cyanophenyl)aminomethyl]benzimidazol-5-yl-carboxylic acid-N-(2-pyridyl)-N-ethoxycarbonylmethylamide Prepared analogously to Example 25c from N-(4-cyanophenyl)glycine and 3-amino-4-methylaminobenzoic acid-N-(2-pyridyl)-N-ethoxycarbonylmethylamide. Yield: 24% of theory; $R_f$ value: 0.56 (silica gel; dichloromethane/methanol=4:1).

b) 1-Methyl-2-[N-4-amidinophenyl)aminomethyl]benzimidazol-5-yl-carboxylic acid-N-(2-pyridyl)-N-(ethoxycarbonylmethyl)amide dihydrochloride Prepared analogously to Example 25d from 1-methyl-2-[N-(4-cyanophenyl)aminomethyl]benzimidazol-5-yl-carboxylic acid-N-(2-pyridyl)-N-(ethoxycarbonylmethyl) amide and ethanolic hydrochloric acid, ethanol, and ammonium carbonate. Yield: 70% of theory, $C_{26}H_{27}N_7O_3$ (485.6); $R_f$ value: 0.16 (silica gel; dichloromethane/ethanol= 4:1); EKA mass spectrum: $(M+H)^+=486$; $(M+2H)^{++}=243.7$; $(M+H-Na)^{++}=254.6$.

EXAMPLE 50

1-Methyl-2-[N-(4-amidinophenyl aminomethyl]
benzimidazol-5-yl-carboxylic acid-N-(2-pyridyl)-N-
(hydroxycarbonylmethyl)amide hydrochloride Prepared analogously to Example 26 from 1-methyl-2-[N-(4-amidinophenyl)aminomethyl]benzimidazol-5-yl-carboxylic acid-N-(2-pyridyl)-N-(ethoxycarbonylmethyl) amide dihydrochloride and sodium hydroxide solution. Yield: 91% of theory, $C_{24}H_{23}N_7O_3$ (457.5); EKA mass spectrum: $(M+H)^+=458$; $(M+Na)^+=480$; $(M+2Na)^{++}=251.7$.

EXAMPLE 51

1-Methyl-2-[2-(4-amidinophenyl)ethyl]
benzimidazol-5-yl-carboxylic acid-N-(2-pyridyl)-N-
(ethoxycarbonylmethyl)amide Dihydrochloride Prepared analogously to Example 25d from 1-methyl-2-[2-(4-cyanophenyl)ethyl]benzimidazol-5-yl-carboxylic acid-N-(2-pyridyl)-N-(ethoxycarbonylmethyl)amide, ethanolic hydrochloric acid, ethanol, and ammonium carbonate. Yield: 90% of theory, $C_{27}H_{28}N_6O_3$ (484.6); $R_f$ value: 0.17 (silica gel; dichloromethane/ethanol=4:1); EKA mass spectrum: $(M+H)^+=485$; $(M+2H)^{++}=243$; $(M+H+Na)^{++}=254$.

EXAMPLE 52

1-Methyl-2-[2-(4-amidinophenyl)ethyl]
benzimidazol-5-yl-carboxylic acid-N-(2-pyridyl)-N-
(hydroxycarbonylmethyl)amide hydrochloride Prepared analogously to Example 26 from 1-methyl-2-[2-(4-amidinophenyl)ethyl]benzimidazol-5-yl-carboxylic acid-N-(2-pyridyl)-N-(ethoxycarbonylmethyl)amide dihydrochloride and sodium hydroxide solution. Yield: 89% of theory, $C_{25}H_{24}N_6O_3$ (456.5); EKA mass spectrum: $(M+H)^+=457$; $(M+Na)^+=479$.

EXAMPLE 53

1-Methyl-2-[N-(4-amidinophenyl)aminomethyl]
benzimidazol-5-yl-carboxylic acid-N-phenyl-N-(2-
methoxycarbonylethyl)amide hydrochloride Prepared analogously to Example 25d from 1-methyl-2-[N-(4-cyanophenyl)aminomethyl]benzimidazol-5-yl-carboxylic acid-N-phenyl-N-(2-ethoxycarbonylethyl)amide and methanolic hydrochloric acid, methanol, and ammonium carbonate. Yield: 87% of theory, $C_{27}H_{28}N_6O_3$ (484.6); $R_f$ value: 0.11 (silica gel; dichloromethane/ethanol=4:1); EKA mass spectrum: $(M+H)^+=485$; $(M+2H)^{++}=243$; $(M+H+Na)^{++}=254$.

EXAMPLE 54

1-Methyl-2-[(4-amidinophenyl)oxymethyl]
benzimidazol-5-yl-carboxylic acid-N-phenyl-N-(2-
ethoxycarbonylethyl)amide hydrochloride Prepared analogously to Example 25d from 1-methyl-2-[(4-cyanophenyl)oxymethyl]benzimidazol-5-yl-carboxylic acid-N-phenyl-N-(2-ethoxycarbonylethyl)amide and ethanolic hydrochloric acid, ethanol, and ammonium carbonate. Yield: 79.5% of theory, $C_{28}H_{29}N_5O_4$ (499.6); $R_f$ value: 0.15 (silica gel; dichloromethane/ethanol=4:1); EKA mass spectrum: $(M+H)^+=500.0$; $(M+H+Na)^{++}=261.7$.

EXAMPLE 55

1-Methyl-2-[(4-amidinophenyl)oxymethyl]
benzimidazol-5-yl-carboxylic acid-N-phenyl-N-(2-
hydroxycarbonylethyl)amide hydrochloride Prepared analogously to Example 26 from 1-methyl-2-[(4-amidinophenyl)oxymethyl]benzimidazol-5-yl-carboxylic acid-N-phenyl-N-(2-ethoxycarbonylethyl)amide hydrochloride and sodium hydroxide solution. Yield: 82% of theory, $C_{26}H_{25}N_5O_4$ (471.5); $R_f$ value: 0.11 (silica gel; dichloromethane/ethanol=4:1); EKA mass spectrum: $(M+H)^+$=472; $(M+H+Na)^{++}$=247.6; $(M+Na)^+$=494; $(M+2Na)^{++}$=258.6.

EXAMPLE 56

1-Methyl-2-[2-(2-amidinothiophen-5-yl)ethyl] benzimidazol-5-yl-carboxylic acid-N-(2-pyridyl-N-(2-ethoxycarbonylethyl)amide hydrochloride a) 1-Methyl-2-[2-(2-cyanothiophen-5-yl)ethyl] benzimidazol-5-yl-carboxylic acid-N-(2-pyridyl-N-(2-ethoxycarbonylethyl)amide Prepared analogously to Example 25c from 3-(2-cyanothiophen-5-yl)propionic acid and 3-amino-4-methylaminobenzoic acid-N-(2-pyridyl)-N-(2-ethoxycarbonylethyl)amide. Yield: 18% of theory; $R_f$ value: 0.66 (silica gel; dichloromethane/methanol=9:1).

b) 1-Methyl-2-[2-(2-amidinothiophen-5-yl)ethyl] benzimidazol-5-yl-carboxylic acid-N-(2-pyridyl)-N-(2-ethoxycarbonylethyl)amide hydrochloride Prepared analogously to Example 25d from 1-methyl-2-[2-(2-cyanothiophen-5-yl)ethyl]benzimidazol-5-yl-carboxylic acid-N-(2-pyridyl)-N-(2-ethoxycarbonylethyl) amide and ethanolic hydrochloric acid, ethanol, and ammonium carbonate. Yield: 53% of theory, $C_{26}H_{28}N_6O_3S$ (504.6); $R_f$ value: 0.22 (silica gel; dichloromethane/methanol=5:1); EKA mass spectrum: $(M+H)^+$=505; $(M+H+Na)^{++}$=264.

EXAMPLE 57

1-Methyl-2-[2-(2-amidinothiophen-5-yl)ethyl] benzimidazol-5-yl-carboxylic acid-N-(pyridyl-N-(2-hydroxycarbonylethyl)amide Prepared analogously to Example 26 from 1-methyl-2-[2-(2-amidinothiophen-5-yl)ethyl]benzimidazol-5-yl-carboxylic acid-N-(2-pyridyl)-N-(2-ethoxycarbonylethyl) amide hydrochloride and sodium hydroxide solution. Yield: 98% of theory, $C_{24}H_{24}N_6O_3S$ (476.6); EKA mass spectrum: $(M+H)^+$=477; $(M+Na)^+$=499; $(M+2H)^{++}$=239.

EXAMPLE 58

1-Methyl-2-[N-(4-amidinophenyl)aminomethyl] benzimidazol-5-yl-carboxylic acid-N-(2-pyridyl)-N-(2-ethoxycarbonylethyl)amide hydrochloride a) 1-Methyl-2-[N-(4-cyanophenyl)aminomethyl] benzimidazol-5-yl-carboxylic acid-N-(2-pyridyl)-N-(2-ethoxycarbonylethyl)amide Prepared analogously to Example 25c from N-(4-cyanophenyl)glycine and 3-amino-4-methylaminobenzoic acid-N-(2-pyridyl)-N-(2-ethoxycarbonylethyl)amide. Yield: 61% of theory; $R_f$ value: 0.62 (silica gel; dichloromethane/methanol=19:1).

b) 1-Methyl-2-[N-(4-amidinophenyl)aminomethyl] benzimidazol-5-yl-carboxylic acid-N-(2-pyridyl)-N-(2-ethoxycarbonylethyl)amide hydrochloride Prepared analogously to Example 25d from 1-methyl-2-[N-(4-cyanophenyl)aminomethyl]benzimidazol-5-yl-carboxylic acid-N-(2-pyridyl)-N-(2-ethoxycarbonylethyl) amide and ethanolic hydrochloric acid, ethanol, and ammonium carbonate. Yield: 71% of theory, $C_{27}H_{29}N_7O_3$ (499.6); $R_f$ value: 0.28 (silica gel; dichloromethane/methanol=5:1); EKA mass spectrum: $(M+H)^+$=500; $(M+H+Na)^{++}$=261.8; $(M+2H)^{++}$=250.8.

EXAMPLE 59

1-Methyl-2-[N-(4-amidinophenyl)aminomethyl] benzimidazol-5-yl-carboxylic acid-N-(2-pyridyl)-N-(2-hydroxycarbonylethyl)amide Prepared analogously to Example 26 from 1-methyl-2-[N-(4-amidinophenyl)aminomethyl]benzimidazol-5-yl-carboxylic acid-N-(2-pyridyl)-N-(2-ethoxycarbonylethyl) amide hydrochloride and sodium hydroxide solution. Yield: 91% of theory, $C_{25}H_{25}N_7O_3$ (471.5); EKA mass spectrum: $(M+H)^+$=472; $(M+H+Na)^{++}$=247.6; $(M+2H)^{++}$=236.7; $(M+2Na)^{++}$=258.6.

EXAMPLE 60

1-Methyl-2-[2-(4-amidinophenyl)ethyl] benzimidazol-5-yl-carboxylic acid-N-(2-pyridyl)-N-(2-ethoxycarbonylethyl)amide hydrochloride a) 1-Methyl-2-[2-(4-cyanophenyl)ethyl]benzimidazol-5-yl-carboxylic acid-N-(2-pyridyl)-N-(2-ethoxycarbonylethyl) amide Prepared analogously to Example 149a from 3-(4-cyanophenyl)propionic acid and 3-amino-4-methylaminobenzoic acid-N-(2-pyridyl)-N-(2-ethoxycarbonylethyl)amide. Yield: 22% of theory; $R_f$ value: 0.68 (silica gel; dichloromethane/methanol=19:1).

b) 1-Methyl-2-[2-(4-amidinophenyl)ethyl]benzimidazol-5-yl-carboxylic acid-N-(2-pyridyl)-N-(2-ethoxycarbonylethyl)amide hydrochloride Prepared analogously to Example 25d from 1-methyl-2-[2-(4-cyanophenyl)ethyl]benzimidazol-5-yl-carboxylic acid-N-(2-pyridyl)-N-(2-ethoxycarbonylethyl)amide and ethanolic hydrochloric acid, ethanol, and ammonium carbonate. Yield: 85% of theory, $C_{28}H_{30}N_6O_3$ (498.6); $R_f$ value: 0.30 (silica gel; dichloromethane/methanol=5:1); EKA mass spectrum: $(M+H)^+$=499; $(M+H+Na)^{++}$=261.

EXAMPLE 61

1-Methyl-2-[2-(4-amidinophenyl)ethyl] benzimidazol-5-yl-carboxylic acid-N-(2-pyridyl)-N-(2-hydroxycarbonylethyl)amide Prepared analogously to Example 26 from 1-methyl-2-[2-(4-amidinophenyl)ethyl]benzimidazol-5-yl-carboxylic acid-N-(2-pyridyl)-N-(2-ethoxycarbonylethyl)amide hydrochloride and sodium hydroxide solution. Yield: 97% of theory, $C_{26}H_{26}N_6O_3$ (470.5); EKA mass spectrum: $(M+H)^+$=471; $(M+H+Na)^{++}$=247; $(M+Na)^+$=493.

EXAMPLE 62

1-Methyl-2-[2-(4-amidinophenyl)ethyl] benzimidazol-5-yl-carboxylic acid-N-phenyl-N-(2-ethoxycarbonylethyl)amide hydrochloride Prepared analogously to Example 25d from 1-methyl-2-[2-(4-cyanophenyl)ethyl]benzimidazol-5-yl-carboxylic acid-N-phenyl-N-(2-ethoxycarbonylethyl)amide and ethanolic hydrochloric acid, ethanol, and ammonium carbonate. Yield: 86% of theory, $C_{29}H_{31}N_5O_3$ (497.6); $R_f$ value: 0.11 (silica gel; dichloromethane/ethanol=4:1); EKA mass spectrum: $(M+H)^+$=498; $(M+2H)^{++}$=249.8.

EXAMPLE 63

1-Methyl-2-[2-(4-amidinophenyl)ethyl] benzimidazol-5-yl-carboxylic acid-N-phenyl-N-(2-hydroxycarbonylethyl)amide hydrochloride Prepared analogously to Example 26 from 1-methyl-2-[2-(4-amidinophenyl)ethyl]benzimidazol-5-yl-carboxylic acid-N-phenyl-N-(2-ethoxycarbonylethyl)amide hydrochloride and sodium hydroxide solution. Yield: 71% of theory, $C_{27}H_{27}N_5O_3$ (469.6); EKA mass spectrum: $(M+H)^+=470$; $(M+H+Na)^{++}=246.6$; $(M+Na)^+=492$; $(M+2H)^{++}=235.6$.

EXAMPLE 64

1-Methyl-2-[N-(4-amidinophenyl)aminomethyl] benzimidazol-5-yl-carboxylic acid-N-(2-pyridyl)-N-(methoxycarbonylmethyl)amide dihydrochloride Prepared analogously to Example 25d from 1-methyl-2-[N-(4-cyanophenyl)aminomethyl]benzimidazol-5-yl-carboxylic acid-N-(2-pyridyl)-N-(methoxycarbonylmethyl) amide and methanolic hydrochloric acid, methanol, and ammonium carbonate. Yield: 73% of theory, $C_2H_{25}N_7O_3$ (471.5); $R_f$ value: 0.12 (silica gel; dichloromethane/ethanol= 4:1); EKA mass spectrum: $(M+H)^+=472$; $(M+H+Na)^{++}=247.8$.

EXAMPLE 65

1-Methyl-2-[N-(4-amidinophenyl)aminomethyl] benzimidazol-5-yl-carboxylic acid-N-(2-pyridyl)-N-(2-methoxycarbonylethyl)amide hydrochloride Prepared analogously to Example 25d from 1-methyl-2-[N-(4-cyanophenyl)aminomethyl]benzimidazol-5-yl-carboxylic acid-N-(2-pyridyl)-N-(2-methoxycarbonylethyl) amide and methanolic hydrochloric acid, methanol, and ammonium carbonate. Yield: 78% of theory, $C_{26}H_{27}N_7O_3$ (485.6); $R_f$ value: 0.31 (silica gel; dichloromethane/methanol=5:1); EKA mass spectrum: $(M+H)^+=486$; $(M+H+Na)^{++}=254.8$.

EXAMPLE 66

1-Methyl-2-[2-(4-amidinophenyl)ethyl] benzimidazol-5-yl-carboxylic acid-N-phenyl-N-[2-(1H-tetrazol-5-yl)ethyl]amide hydrochloride a) 1-Methyl-2-[2-(4-cyanophenyl)ethyl]benzimidazol-5-yl-carboxylic acid-N-phenyl-N-[2-(1H-tetrazol-5-yl)ethyl] amide Prepared analogously to Example 25c from 3-(4-cyanophenyl)propionic acid and 3-amino-4-methylaminobenzoic acid-N-phenyl-N-[2-(1H-tetrazol-5-yl)ethyl]amide. Yield: 67% of theory; IR mass spectrum (KBr): characteristic bands at 3439.5 cm$^{-1}$ (N—H); 2235.5 cm$^{-1}$ (C≡N) 1631.6 cm$^{-1}$ (C=O).

b) 1-Methyl-2-[2-(4-amidinophenyl)ethyl]benzimidazol-5-yl-carboxylic acid-N-phenyl-N-[2-(1H-tetrazol-5-yl)ethyl] amide hydrochloride Prepared analogously to Example 25d from 1-methyl-2-[2-(4-cyanophenyl)ethyl]benzimidazol-5-yl-carboxylic acid-N-phenyl-N-[2-(1H-tetrazol-5-yl)ethyl]amide and ethanolic hydrochloric acid, ethanol, and ammonium carbonate. Yield: 92% of theory, $C_{27}H_{27}N_9O$ (493.6); EKA mass spectrum: $(M+H)^+=494$; $(M+Na)^+=516$; $(M+2H)^{++}=258.7$.

EXAMPLE 67

1-Methyl-2-[N-(4-amidinophenyl)aminomethyl] benzimidazol-5-yl-carboxylic acid-N-phenyl-N-[2-(1H-tetrazol-5-yl)ethyl]amide hydrochloride Prepared analogously to Example 25d from 1-methyl-2-[N-(4-cyanophenyl)aminomethyl]benzimidazol-5-yl-carboxylic acid-N-phenyl-N-[2-(1H-tetrazol-5-yl)ethyl] amide and ethanolic hydrochloric acid, ethanol, and ammonium carbonate. Yield: 29% of theory, $C_{26}H_{26}N_{10}O$ (494.6); EKA mass spectrum: $(M+H)^+=495$.

EXAMPLE 68

1-Methyl-2-[N-(4-amidinophenyl)aminomethyl] benzimidazol-5-yl-carboxylic acid-N-(2-pyridyl)-N-(2-n-hexyloxycarbonylethyl)amide hydrochloride 0.60 g (1.1 mmol) of 1-methyl-2-[N-(4-amidinophenyl) aminomethyl]benzimidazol-5-yl-carboxylic acid-N-(2-pyridyl)-N-(2-ethoxycarbonylethyl)amide hydrochloride were added to about 30 mL of n-hexanol saturated with hydrogen chloride and the mixture was stirred for 19 hours at room temperature. Then the hexanol was distilled off in vacuo, the residue was mixed with about 5 mL of 1N ammonia solution with stirring, and evaporated down once more. The crude product thus obtained was purified by column chromatography (silica gel, dichloromethane/methanol=5:1). Yield: 53% of theory, $C_{31}H_{37}N_7O_3$ (555.7); $R_f$ value: 0.36 (silica gel; dichloromethane/methanol=5:1); EKA mass spectrum: $(M+H)^+=556$.

EXAMPLE 69

1-Methyl-2-[N-(4-amidinophenyl)-N-methylaminomethyl]benzimidazol-5-yl-carboxylic acid-N-(2-pyridyl)-N-(2-ethoxycarbonylethyl)amide hydrochloride a) 1-Methyl-2-[N-(4-cyanophenyl)-N-methylaminomethyl] benzimidazol-5-yl-carboxylic acid-N-(2-pyridyl)-N-(2-ethoxycarbonylethyl)amide Prepared analogously to Example 25c from N-(4-cyanophenyl)-N-methylglycine and 3-amino-4-methylaminobenzoic acid-N-(2-pyridyl)-N-(2-ethoxycarbonylethyl)amide. Yield: 71% of theory; $R_f$ value: 0.66 (silica gel; dichloromethane/methanol=19:1).

b) 1-Methyl-2-[N-(4-amidinophenyl)-N-methylaminomethyl]benzimidazol-5-yl-carboxylic acid-N-(2-pyridyl)-N-(2-ethoxycarbonylethyl)amide hydrochloride Prepared analogously to Example 25d from 1-methyl-2-[N-(4-cyanophenyl)-N-methylaminomethyl]benzimidazol-5-yl-carboxylic acid-N-(2-pyridyl)-N-(2-ethoxycarbonylethyl)amide and ethanolic hydrochloric acid, ethanol, and ammonium carbonate. Yield: 77% of theory, $C_{28}H_{31}N_7O_3$ (513.6); EKA mass spectrum: $(M+H)^+=514$; $(M+H+Na)^{++}=268.7$.

EXAMPLE 70

1-Methyl-2-[N-(4-amidinophenyl)-N-methylaminomethyl]benzimidazol-5-yl-carboxylic acid-N-(2-pyridyl)-N-(2-hydroxycarbonylethyl) amide Prepared analogously to Example 26 from 1-methyl-2-[N-(4-amidinophenyl)-N-methylaminomethyl] benzimidazol-5-yl-carboxylic acid-N-(2-pyridyl)-N-(2-ethoxycarbonylethyl)amide hydrochloride and sodium hydroxide solution. Yield: 66% of theory, $C_{26}H_{27}N_7O_3$ (485.6); EKA mass spectrum: $(M+H)^+=486$; $(M+Na)^+=508$; $(M+2Na)^{++}=265.6$.

EXAMPLE 71

1-Methyl-2-[2-(4-amidinophenyl)ethyl] benzimidazol-5-yl-carboxylic acid-N-cyclopentyl-N-(2-ethoxycarbonylethyl)amide hydrochloride Prepared analogously to Example 25d from 1-methyl-2-[2-(4-cyanophenyl)ethyl]benzimidazol-5-yl-carboxylic acid-N-cyclopentyl-N-(2-ethoxycarbonylethyl)amide and ethanolic hydrochloric acid, ethanol, and ammonium carbonate. Yield: 65% of theory, $C_{28}H_{35}N_5O_3$ (489.6); EKA mass spectrum: $(M+H)^+=490$.

EXAMPLE 72

1-Methyl-2-[2-(4-amidinophenyl)ethyl] benzimidazol-5-yl-carboxylic acid-N-cyclopentyl-N-(2-hydroxycarbonylethyl)amide Prepared analogously to Example 26 from 1-methyl-2-[2-(4-amidinophenyl)ethyl]benzimidazol-5-yl-carboxylic acid-N-cyclopentyl-N-(2-ethoxycarbonylethyl)amide hydrochloride and sodium hydroxide solution. Yield: 89% of theory, $C_{26}H_{31}N_5O_3$ (461.6); EKA mass spectrum: $(M+H)^+=462$; $(M+H+Na)^{++}=242.6$; $(M+Na)^+=484$; $(M+2H)^{++}=231.6$.

EXAMPLE 73

1-Methyl-2-[N-(4-amidinophenyl)aminomethyl] benzimidazol-5-yl-carboxylic acid-N-cyclopentyl-N-(2-ethoxycarbonylethyl)amide hydrochloride Prepared analogously to Example 25d from 1-methyl-2-[N-(4-cyanophenyl)aminomethyl]benzimidazol-5-yl-carboxylic acid-N-cyclopentyl-N-(2-ethoxycarbonylethyl)amide and ethanolic hydrochloric acid, ethanol, and ammonium carbonate. Yield: 60% of theory, $C_{27}H_{34}N_6O_3$ (490.6); EKA mass spectrum: $(M+H)^+=491$.

EXAMPLE 74

1-Methyl-2-[N-(4-amidinophenyl)aminomethyl] benzimidazol-5-yl-carboxylic acid-N-cyclopentyl-N-(2-hydroxycarbonylethyl)amide Prepared analogously to Example 26 from 1-methyl-2-[N-(4-amidinophenyl)aminomethyl]benzimidazol-5-yl-carboxylic acid-N-cyclopentyl-N-(2-ethoxycarbonylethyl)amide hydrochloride and sodium hydroxide solution. Yield: 45% of theory, $C_{25}H_{30}N_3O_4$ (462.6); EKA mass spectrum: $(M+H)^+=463$; $(M+H+Na)^{++}=243$; $(M+Na)^+=485$; $(M+2Na)^{++}=254$.

EXAMPLE 75

1-Methyl-2-[N-(4-amidinophenyl)-N-methylaminomethyl]benzimidazol-5-yl-carboxylic acid-N-(2-pyridyl)-N-(ethoxycarbonylmethyl)amide hydrochloride Prepared analogously to Example 25d from 1-methyl-2-[N-(4-cyanophenyl)-N-methylaminomethyl]benzimidazol-5-yl-carboxylic acid-N-(2-pyridyl)-N-(ethoxycarbonylmethyl)amide and ethanolic hydrochloric acid, ethanol, and ammonium carbonate. Yield: 54% of theory, $C_{27}H_{29}N_7O_3$ (499.6); EKA mass spectrum: $(M+H)^+=500$; $(M+2H)^{++}=250.7$.

EXAMPLE 76

1-Methyl-2-[N-4-amidinophenyl)-N-methylaminomethyl]benzimidazol-5-yl-carboxylic acid-N-(2-pyridyl)-N-(hydroxycarbonylmethyl) amide Prepared analogously to Example 26 from 1-methyl-2-[N-(4-amidinophenyl)-N-methylaminomethyl] benzimidazol-5-yl-carboxylic acid-N-(2-pyridyl)-N-(ethoxycarbonylmethyl)amide hydrochloride and sodium hydroxide solution. Yield: 68% of theory, $C_{25}H_{25}N_7O_3$ (471.5); EKA mass spectrum: $(M+H)^+=472$; $(M+Na)^+=494$; $(M+2Na)^{++}=258.6$.

EXAMPLE 77

1-Methyl-2-[2-(4-amidinophenyl)ethyl] benzimidazol-5-yl-carboxylic acid-N-(3-pyridyl)-N-(2-ethoxycarbonylethyl)amide hydrochloride Prepared analogously to Example 25d from 1-methyl-2-[2-(4-cyanophenyl)ethyl]benzimidazol-5-yl-carboxylic acid-N-(3-pyridyl)-N-(2-ethoxycarbonylethyl)amide and ethanolic hydrochloric acid, ethanol, and ammonium carbonate. Yield: 91% of theory, $C_{28}H_{30}N_6O_3$ (498.6); $R_f$ value: 0.19 (silica gel; dichloromethane/ethanol=4:1); EKA mass spectrum: $(M+H)^+=499$.

EXAMPLE 78

1-Methyl-2-[N-(4-amidinophenyl)aminomethyl] benzimidazol-5-yl-carboxylic acid-N-(3-pyridyl)-N-(2-ethoxycarbonylethyl)amide dihydrochloride Prepared analogously to Example 25d from 1-methyl-2-[N-(4-cyanophenyl)aminomethyl]benzimidazol-5-yl-carboxylic acid-N-(3-pyridyl)-N-(2-ethoxycarbonylethyl) amide and ethanolic hydrochloric acid, ethanol, and ammonium carbonate. Yield: 86% of theory, $C_{27}H_{29}N_7O_3$ (499.6); $R_f$ value: 0.09 (silica gel; dichloromethane/ethanol=4:1); EKA mass spectrum: $(M+H)^+=500$.

EXAMPLE 79

1-Methyl-2-[N-(4-amidinophenyl)aminomethyl] benzimidazol-5-yl-carboxylic acid-N-(3-pyridyl)-N-(2-hydroxycarbonylethyl)amide Prepared analogously to Example 26 from 1-methyl-2-[N-(4-amidinophenyl)aminomethyl]benzimidazol-5-yl-carboxylic acid-N-(3-pyridyl)-N-(2-ethoxycarbonylethyl) amide dihydrochloride and sodium hydroxide solution. Yield: 85% of theory, $C_{25}H_{25}N_7O_3$ (471.5); EKA mass spectrum: $(M+H)^+=472$; $(M+2H)^{++}=236.6$; $(M+2Na)^{++}=258.6$.

EXAMPLE 80

1-Methyl-2-[N-(4-amidinophenyl)-N-methylaminomethyl]benzimidazol-5-yl-carboxylic acid-N-(3-pyridyl)-N-(2-ethoxycarbonylethyl)amide hydrochloride Prepared analogously to Example 25d from 1-methyl-2-[N-(4-cyanophenyl)-N-methylaminomethyl]benzimidazol-5-yl-carboxylic acid-N-(3-pyridyl)-N-(2-ethoxycarbonylethyl)amide and ethanolic hydrochloric acid, ethanol, and ammonium carbonate. Yield: 64% of theory, $C_{28}H_{31}N_7O_3$ (513.6); EKA mass spectrum: $(M+H)^+=514$.

EXAMPLE 81

1-Methyl-2-[N-(4-amidinophenyl)-N-methylaminomethyl]benzimidazol-5-yl-carboxylic acid-N-(3-pyridyl)-N-(2-hydroxycarbonylethyl) amide Prepared analogously to Example 26 from 1-methyl-2-[N-(4-amidinophenyl)-N-methylaminomethyl]

benzimidazol-5-yl-carboxylic acid-N-(3-pyridyl)-N-(2-ethoxycarbonylethyl)amide hydrochloride and sodium hydroxide solution. Yield: 70% of theory, $C_{26}H_{27}N_7O_3$ (485.6); EKA mass spectrum: (M+H)$^+$=486; (M+Na)$^+$=508; (M+2Na)$^{++}$=265.6.

EXAMPLE 82

1-Methyl-2-[N-(4-amidinophenyl-N-methylaminomethyl]benzimidazol-5-yl-carboxylic acid-N-phenyl-N-(2-ethoxycarbonylethyl)amide hydrochloride a) 1-Methyl-2-[N-(4-cyanophenyl)-N-methylaminomethyl]benzimidazol-5-yl-carboxylic acid-N-phenyl-N-(2-pyridyl)-N-(2-ethoxycarbonylethyl)amide Prepared analogously to Example 25c from N-(4-cyanophenyl)-N-methylglycine and 3-amino-4-methylaminobenzoic acid-N-phenyl-N-(2-ethoxycarbonylethyl)amide. Yield: 71% of theory; $R_f$ value: 0.38 (silica gel; dichloromethane/methanol=19:1).

b) 1-Methyl-2-[N-(4-amidinophenyl)-N-methylaminomethyl]benzimidazol-5-yl-carboxylic acid-N-phenyl-N-(2-ethoxycarbonylethyl)amide hydrochloride Prepared analogously to Example 25d from 1-methyl-2-[N-(4-cyanophenyl)-N-methylaminomethyl]benzimidazol-5-yl-carboxylic acid-N-phenyl-N-(2-ethoxycarbonylethyl)amide and ethanolic hydrochloric acid, ethanol, and ammonium carbonate. Yield: 74% of theory, $C_{29}H_{32}N_6O_3$ (512.6); EKA mass spectrum: (M+H)$^+$=513; (M+H+Na)$^{++}$=268; (M+2H)$^{++}$=257.

EXAMPLE 83

1-Methyl-2-[N-(4-amidinophenyl)-N-methylaminomethyl]benzimidazol-5-yl-carboxylic acid-N-phenyl-N-(2-hydroxycarbonylethyl)amide Prepared analogously to Example 26 from 1-methyl-2-[N-(4-amidinophenyl)-N-methylaminomethyl]benzimidazol-5-yl-carboxylic acid-N-phenyl-N-(2-ethoxycarbonylethyl)amide hydrochloride and sodium hydroxide solution. Yield: 80% of theory, $C_{27}H_{28}N_6O_3$ (484.6); EKA mass spectrum: (M+H)$^+$=485; (M+H+Na)$^{++}$=254; (M+Na)$^+$=507; (M+2Na)$^+$=265.

EXAMPLE 84

1-methyl-2-[-(4-amidinophenyl)aminomethyl]benzimidazol-5-yl-carboxylic acid-N-(2-pyridyl)-N-(2-ethoxycarbonylethyl)amide hydrochloride Prepared analogously to Example 25d from 1-ethyl-2-[N-(4-cyanophenyl)aminomethyl]benzimidazol-5-yl-carboxylic acid-N-(2-pyridyl)-N-(2-ethoxycarbonylethyl)amide and ethanolic hydrochloric acid, ethanol, and ammonium carbonate. Yield: 85% of theory, $C_{28}H_{31}N_7O_3$ (513.6); $R_f$ value: 0.21 (silica gel; dichloromethane/methanol=5:1); EKA mass spectrum: (M+H)$^+$=514; (M+H+Na)$^{++}$=268.6; (M+2H)$^{++}$=257.7.

EXAMPLE 85

1-ethyl-2-[N-(4-amidinophenyl)aminomethyl]benzimidazol-5-yl-carboxylic acid-N-(2-pyridyl)-N-(2-hydroxycarbonylethyl)amide Prepared analogously to Example 26 from 1-ethyl-2-[N-(4-amidinophenyl)aminomethyl]benzimidazol-5-yl-carboxylic acid-N-(2-pyridyl)-N-(2-ethoxycarbonylethyl) amide hydrochloride and 2N sodium hydroxide solution. Yield: 49% of theory, $C_{26}H_{27}N_7O_3$ (485.6); EKA mass spectrum: (M+H)$^+$=486; (M+H+Na)$^{++}$=254.6; (M+2H)$^{++}$=243.6; (M+2Na)$^{++}$=265.7.

EXAMPLE 86

1-Methyl-2-[N-(4-amidinophenyl)aminomethyl]benzimidazol-5-yl-carboxylic acid-N-(2-fluorophenyl)-N-(2-ethoxycarbonylethyl)amide hydrochloride Prepared analogously to Example 25d from 1-methyl-2-[N-(4-cyanophenyl)aminomethyl]benzimidazol-5-yl-carboxylic acid-N-(2-fluorophenyl)-N-(2-ethoxycarbonylethyl)amide and ethanolic hydrochloric acid, ethanol, and ammonium carbonate. Yield: 88% of theory, $C_{28}H_{29}FN_6O_3$ (516.6); $R_f$ value: 0.08 (silica gel; dichloromethane/ethanol=4:1); EKA mass spectrum: (M+H)$^+$=517; (M+H+Na)$^{++}$=270; (M+2H)$^{++}$=259.

EXAMPLE 87

1-Methyl-2-[N-(4-amidinophenyl)aminomethyl]benzimidazol-5-yl-carboxylic acid-N-(2-fluorophenyl)-N-(2-hydroxycarbonylethyl)amide Prepared analogously to Example 26 from 1-methyl-2-[N-(4-amidinophenyl)aminomethyl]benzimidazol-5-yl-carboxylic acid-N-(2-fluorophenyl)-N-(2-ethoxycarbonylethyl)amide hydrochloride and sodium hydroxide solution. Yield: 45% of theory, $C_{26}H_{25}FN_6O_3$ (488.5); $R_f$ value: 0.05 (silica gel; dichloromethane/ethanol=4:1); EKA mass spectrum: (M+H)$^+$=489; (M+H+Na)$^{++}$=267; (M+2H)$^{++}$=256.

EXAMPLE 88

1-Methyl-2-[N-(4-amidinophenyl)aminomethyl]benzimidazol-5-yl-carboxylic acid-N-(3-methylphenyl)-N-(2-ethoxycarbonylethyl)amide hydrochloride Prepared analogously to Example 25d from 1-methyl-2-[N-(4-cyanophenyl)aminomethyl]benzimidazol-5-yl-carboxylic acid-N-(3-methylphenyl)-N-(2-ethoxycarbonylethyl)amide and ethanolic hydrochloric acid, ethanol, and ammonium carbonate. Yield: 79% of theory, $C_{29}H_{32}N_6O_3$ (512.6); $R_f$ value: 0.10 (silica gel; dichloromethane/ethanol=4:1); EKA mass spectrum: (M+H)$^+$=513; (M+H+Na)$^{++}$=268.

EXAMPLE 89

1-Methyl-2-[N-(4-amidinophenyl)aminomethyl]benzimidazol-5-yl-carboxylic acid-N-(3-methylphenyl)-N-(2-hydroxycarbonylethyl)amide Prepared analogously to Example 26 from 1-methyl-2-[N-(4-amidinophenyl)aminomethyl]benzimidazol-5-yl-carboxylic acid-N-(3-methylphenyl)-N-(2-ethoxycarbonylethyl)amide hydrochloride and sodium hydroxide solution. Yield: 62% of theory, $C_{27}H_{28}N_6O_3$ (484.6); EKA mass spectrum: (M+H)$^+$=485; (M+H+Na)$^{++}$=254; (M+Na)$^+$=507; (M+2Na)$^{++}$=265.

EXAMPLE 90

1-Methyl-2-[N-[4-(N-n-hexyloxycarbonylamidino)phenyl]aminomethyl]benzimidazol-5-yl-carboxylic acid-N-phenyl-N-(2-ethoxycarbonylethyl)amide 1.1 g (2.06 mmol) of 1-methyl-2-[N-(4-amidinophenyl)aminomethyl]benzimidazol-5-yl-carboxylic acid-N-phenyl- N-(2-ethoxycarbonylethyl)amide hydrochloride was dissolved in a mixture of 40 mL of tetrahydrofuran and 10 mL of water, then 570 mg (4.12 mmol) of potassium carbonate and 362 mg (2.2 mmol) of n-hexyl chloroformate were added and stirred for two hours at room temperature. The solvent was then distilled off, the residue was mixed with about 50 mL of saturated saline solution and the resulting solution was extracted three times with 20 mL of dichloromethane. The extracts were dried over sodium sulfate and evaporated down. The crude product thus obtained was purified by column chromatography (100 g silica gel; dichloromethane+5% ethanol). Yield: 78% of theory, $C_{35}H_{42}N_6O_5$ (626.8); $R_f$ value: 0.49 (silica gel; dichloromethane/ethanol=19:1); EKA mass spectrum: $(M+H)^+=627$; $(M+H+Na)^{++}=325$; $(M+2H)^{++}=314$.

EXAMPLE 91

1-Methyl-2-[N-[4-(N-methoxycarbonylamidino) phenyl]aminomethyl]benzimidazol-5-yl-carboxylic acid-N-phenyl-N-(2-ethoxycarbonylethyl)amide Prepared analogously to Example 90 from 1-methyl-2-[N-(4-amidinophenyl)aminomethyl]benzimidazol-5-yl-carboxylic acid-N-phenyl-N-(2-ethoxycarbonylethyl)amide hydrochloride and methyl chloroformate. Yield: 41% of theory, $C_{30}H_{32}N_6O_5$ (556.6); $R_f$ value: 0.85 (silica gel; dichloromethane/ethanol=4:1); EKA mass spectrum: $(M+H)^+=557$; $(M+H+Na)^{++}=290$; $(M+Na)^+=579$.

EXAMPLE 92

1-Methyl-2-[N-[4-(N-ethoxycarbonylamidino) phenyl]aminomethyl]benzimidazol-5-yl-carboxylic acid-N-phenyl-N-(2-methoxycarbonylethyl)amide Prepared analogously to Example 90 from 1-methyl-2-[N-(4-amidinophenyl)aminomethyl]benzimidazol-5-yl-carboxylic acid-N-phenyl-N-(2-methoxycarbonylethyl)amide hydrochloride and ethyl chloroformate. Yield: 62% of theory, $C_{30}H_{32}N_6O_5$ (556.6); $R_f$ value: 0.51 (silica gel; dichloromethane/ethanol=19:1); EKA mass spectrum: $(M+H)^+=557$; $(M+H+Na)^{++}=290$; $(M+2H)^{++}=279$.

EXAMPLE 93

1-Methyl-2-[N-[4-(N-cyclohexyloxycarbonylamidino)phenyl] aminomethyl]benzimidazol-5-yl-carboxylic acid-N-phenyl-N-(2-methoxycarbonylethyl)amide Prepared analogously to Example 90 from 1-methyl-2-[N-(4-amidinophenyl)aminomethyl]benzimidazol-5-yl-carboxylic acid-N-phenyl-N-(2-methoxycarbonylethyl)amide hydrochloride and cyclohexyl chloroformate. Yield: 25% of theory, $C_{34}H_{38}N_6O_5$ (610.7); $R_f$ value: 0.44 (silica gel; dichloromethane/ethanol=19:1); EKA mass spectrum: $(M+H)^+=611$; $(M+2H)^{++}=306$.

EXAMPLE 94

1-Methyl-2-[N-[4-[N-(2-(methylsulfonyl) ethyloxycarbonyl]amidino]phenyl]aminomethyl]-benzimidazol-5-yl-carboxylic acid-N-phenyl-N-(2-ethoxycarbonylethyl)amide Prepared analogously to Example 90 from 1-methyl-2-[N-(4-amidinophenyl)aminomethyl]benzimidazol-5-yl-carboxylic acid-N-phenyl-N-(2-ethoxycarbonylethyl)amide hydrochloride and 2-(methylsulfonyl)ethyl chloroformate. Yield: 66% of theory, $C_{32}H_{36}N_6O_7S$ (648.8); $R_f$ value: 0.44 (silica gel; dichloromethane/ethanol=19:1); EKA mass spectrum: $(M+H)^+=649$; $(M+H+Na)^{++}=336(M+2H)^{++}=325$.

EXAMPLE 95

1-Methyl-2-[N-[4-(N-n-octyloxycarbonylamidino) phenyl]aminomethyl]benzimidazol-5-yl-carboxylic acid-N-phenyl-N-(2-methoxycarbonylethyl)amide Prepared analogously to Example 90 from 1-methyl-2-[N-(4-amidinophenyl)aminomethyl]benzimidazol-5-yl-carboxylic acid-N-phenyl-N-(2-methoxycarbonylethyl) amide hydrochloride and n-octyl chloroformate. Yield: 41% of theory, $C_{36}H_{44}N_6O_5$ (640.8); $R_f$ value: 0.43 (silica gel; dichloromethane/ethanol=19:1); EKA mass spectrum: $(M+H)^+=641$; $(M+Na)^+=663$.

EXAMPLE 96

1-Methyl-2-[N-[4-(N-hydroxylamidino)phenyl] aminomethyl]benzimidazol-5-yl-carboxylic acid-N-phenyl-N-(2-ethoxycarbonylethyl)amide 1.44 g (3.0 mmol) of 1-methyl-2-[N-(4-cyanophenyl) aminomethyl]benzimidazol-5-yl-carboxylic acid-N-phenyl-N-(2-ethoxycarbonylethyl)amide, 0.625 g (9.0 mmol) of hydroxylamine hydrochloride and 0.425 g (4.0 mmol) of sodium carbonate were dissolved in 80 mL of ethanol and refluxed for 7 hours. Then a further 210 mg of hydroxylamine hydrochloride and 170 mg of sodium carbonate were added, the mixture was boiled for a further 5 hours and then evaporated down in vacuo. The residue was dissolved in about 30 mL of dichloromethane, the solution obtained was washed with 20 mL of water, the organic phase was dried and evaporated down. The crude product thus obtained was purified by column chromatography (200 g silica gel, dichloromethane +4% ethanol). Yield: 39% of theory, $C_{28}H_{30}N_6O_4$ (514.6); $R_f$ value: 0.15 (silica gel; dichloromethane/ethanol=19:1); EKA mass spectrum: $(M+H)^+=515$; $(M+Na)^+=537$; $(2M+H)^+=1029$; $(2M+Na)^+=1051$.

EXAMPLE 97

1-Methyl-2-[N-[4-(N-n-heptyloxycarbonylamidino) phenyl]aminomethyl]benzimidazol-5-yl-carboxylic acid-N-phenyl-N-(2-methoxycarbonylethyl)amide Prepared analogously to Example 90 from 1-methyl-2-[N-(4-amidinophenyl)amino methyl]benzimidazol-5-yl-carboxylic acid-N-phenyl-N-(2-methoxycarbonylethyl) amide hydrochloride and n-heptyl chloroformate. Yield: 43% of theory, $C_{35}H_{42}N_6O_5$ (626.8); $R_f$ value: 0.40 (silica gel; dichloromethane/ethanol=19:1); EKA mass spectrum: $(M+H)^+=627$; $(M+H+Na)^{++}=325$; $(M+Na)^+=649$.

EXAMPLE 98

1-Methyl-2-[N-[4(N-benzoylamidino)phenyl] aminomethyl]benzimidazol-5-yl-carboxylic acid-N-phenyl-N-(2-methoxycarbonylethyl)amide Prepared analogously to Example 90 from 1-methyl-2-[N-(4-amidinophenyl)aminomethyl]benzimidazol-5-yl-carboxylic acid-N-phenyl-N-(2-methoxycarbonylethyl) amide hydrochloride and benzoyl chloride. Yield: 88% of theory, $C_{34}H_{32}N_6O_4$ (588.7); $R_f$ value: 0.37 (silica gel; dichloromethane/ethanol=19:1); $^1$H-NMR spectrum ($D_6$-DMSO): 2.61 (t,2H), 3.54 (s,3H), 3.76 (s,3H), 4.10 (t,2H), 4.61 (d,2H), 6.83 (d,2H), 7.05 to 7.55 (m,12H),8.03 (d,2H), 8.25 (dd,2H), 8.98 (s,1H), 10.48 (s,1H).

EXAMPLE 99

1-Methyl-2-[N-[4-(N-n-hexyloxycarbonylamidino) phenyl]aminomethyl]benzimidazol-5-yl-carboxylic acid-N-phenyl-N-(2-methoxycarbonylethyl)amide Prepared analogously to Example 90 from 1-methyl-2-[N-(4-amidinophenyl)aminomethyl]benzimidazol-5-yl-carboxylic acid-N-phenyl-N-(2-methoxy-carbonylethyl) amide hydrochloride and n-hexyl chloroformate. Yield: 54% of theory, $C_{34}H_{40}N_6O_5$ (612.7); $R_f$ value: 0.45 (silica gel; dichloromethane/ethanol=19:1); EKA mass spectrum: $(M+H)^+=613$.

EXAMPLE 100

1-Methyl-2-[N-[4-(N-n-hexyloxycarbonylamidino) phenyl]aminomethyl]benzimidazol-5-yl-carboxylic acid-N-phenyl-N-(2-n-propyloxycarbonylethyl) amide Prepared analogously to Example 90 from 1-methyl-2-[N-(4-amidinophenyl)aminomethyl]benzimidazol-5-yl-carboxylic acid-N-phenyl-N-(2-n-propyloxycarbonylethyl) amide hydrochloride and n-hexyl chloroformate. Yield: 31% of theory, $C_{36}H_{44}N_6O_5$ (640.8); $R_f$ value: 0.42 (silica gel; dichloromethane/ethanol=19:1); EKA mass spectrum: $(M+H)^+=641$; $(M+H+Na)^{++}=332$; $(M+Na)^+=663$.

EXAMPLE 101

1-Methyl-2-[N-[4-(N-ethoxycarbonylamidino) phenyl]aminomethyl]benzimidazol-5-yl-carboxylic acid-N-(2-pyridyl)-N-(2-methoxycarbonylethyl) amide Prepared analogously to Example 90 from 1-methyl-2-[N-(4-amidinophenyl)aminomethyl]benzimidazol-5-yl-carboxylic acid-N-(2-pyridyl)-N-(2-methoxycarbonylethyl) amide hydrochloride and ethyl chloroformate. Yield: 72% of theory, $C_{29}H31N_7O_5$ (557.6); $R_f$ value: 0.58 (silica gel; dichloromethane/methanol=9:1); EKA mass spectrum: $(M+H)^+=558$; $(M+H+Na)^{++}=290.8$; $(M+Na)^+=580$.

EXAMPLE 102

1-Methyl-2-[N-[4-(N-n-octyloxycarbonylamidino) phenyl]aminomethyl]benzimidazol-5-yl-carboxylic acid-N-(2-pyridyl)-N-(2-methoxycarbonylethyl) amide Prepared analogously to Example 90 from 1-methyl-2-[N-(4-amidinophenyl)aminomethyl]benzimidazol-5-yl-carboxylic acid-N-(2-pyridyl)-N-(2-methoxycarbonylethyl) amide hydrochloride and n-octyl chloroformate. Yield: 57% of theory, $C_{35}H_{43}N_7O_5$ (641.8); $R_f$ value: 0.60 (silica gel; dichloromethane/methanol=9:1); EKA mass spectrum: $(M+H)^+=642$; $(M+H+Na)^{++}=332.8$; $(M+Na)^+=664$.

EXAMPLE 103

1-Methyl-2-[N-[4-(N-methoxycarbonylamidino) phenyl]aminomethyl]benzimidazol-5-yl-carboxylic acid-N-(2-pyridyl)-N-(2-ethoxycarbonylethyl)amide Prepared analogously to Example 90 from 1-methyl-2-[N-(4-amidinophenyl)aminomethyl]benzimidazol-5-yl-carboxylic acid-N-(2-pyridyl)-N-(2-ethoxycarbonylethyl) amide hydrochloride and methyl chloroformate. Yield: 48% of theory, $C_{29}H_{31}N_7O_5$ (557.6); $R_f$ value: 0.62 (silica gel; dichloromethane/methanol=9:1); EKA mass spectrum: $(M+H)^+=558$; $(M+H+Na)^{++}=290.7$; $(M+Na)^+=580$.

EXAMPLE 104

1-Methyl-2-[N-[4-(N-n-octyloxycarbonylamidino) phenyl]aminomethyl)benzimidazol-5-yl-carboxylic acid-N-(2-pyridyl)-N-(2-hydroxycarbonylethyl) amide 0.7 g (1.1 mmol) of 1-methyl-2-[N-[4-(N-n-octyloxycarbonylamidino)phenyl]aminomethyl]-benzimidazol-5-yl-carboxylic acid-N-(2-pyridyl)-N-(2-methoxycarbonylethyl)amide was stirred in a mixture of 0.12 g (3.0 mmol) of sodium hydroxide, 5 mL of water, and 10 mL of methanol for one hour at room temperature. Then the mixture was diluted with 20 mL of water and adjusted to pH 6 with glacial acetic acid. Then about 5 mL of diethylether were added and the mixture was vigorously stirred for one hour. The product thus precipitated was suction filtered, washed with a little water, then with diethylether and dried. Yield: 80% of theory, $C_{34}H_{41}N_7O_5$ (627.8); EKA mass spectrum: $(M+H)^+=628$; $(M+H+Na)^{++}=325.7$; $(M+Na)^+=650$; $(M+2Na)^{++}=337.7$.

EXAMPLE 105

1-Methyl-2-[N-[4-[N-(2-methylsulfonylethyloxycarbonyl) amidino]phenyl] aminomethyl]-benzimidazol-5-yl-carboxylic acid-N-(2-pyridyl)-N-(2-ethoxycarbonylethyl)amide Prepared analogously to Example 90 from 1-methyl-2-[N-(4-amidinophenyl) aminomethyl]-benzimidazol-5-yl-carboxylic acid-N-(2-pyridyl)-N-(2-ethoxycarbonylethyl) amide hydrochloride and 2-(methylsulfonyl)ethyl chloroformate. Yield: 65% of theory, $C_{31}H_{35}N_7O_7S$ (649.7); $R_f$ value: 0.54 (silica gel; dichloromethane/methanol=9:1); EKA mass spectrum: $(M+H)^+=650$; $(M+H+Na)^{++}=336.6$; $(M+Na)^+=672$; $(M+2Na)^{++}=347.6$.

EXAMPLE 106

1-Methyl -2-[N-[4-(N-n-butyloxycarbonylamidino) phenyl]aminomethyl]benzimidazol-5-yl-carboxylic acid-N-(2-pyridyl)-N-(2-methoxycarbonylethyl) amide Prepared analogously to Example 90 from 1-methyl-2-[N-(4-amidinophenyl)aminomethyl]benzimidazol-5-yl-carboxylic acid-N-(2-pyridyl)-N-(2-methoxycarbonylethyl) amide hydrochloride and n-butyl chloroformate. Yield: 30% of theory, $C_{31}H_{35}N_7O_5$ (585.7); $R_f$ value: 0.62 (silica gel; dichloromethane/methanol=9:1); EKA mass spectrum: $(M+H)^+=586$; $(M+H+Na)^{++}=304.7$; $(M+2H)^{++}=293.7$.

EXAMPLE 107

1-Methyl-2-[N-[4-(N-n-hexyloxycarbonylamidino) phenyl]aminomethyl]benzimidazol-5-yl-carboxylic acid-N-(2-pyridyl)-N-(2-methoxycarbonylethyl) amide Prepared analogously to Example 90 from 1-methyl-2-[N-(4-amidinophenyl)aminomethyl]benzimidazol-5-yl-carboxylic acid-N-(2-pyridyl)-N-(2-methoxycarbonylethyl) amide hydrochloride and n-hexyl chloroformate. Yield: 51% of theory, $C_{33}H_{39}N_7O_5$ (613.7); $R_f$ value: 0.56 (silica gel; dichloromethane/methanol=9:1); EKA mass spectrum: $(M+H)^+=614$; $(M+H+Na)^{++}=318.7$; $(M+2H)^{++}=307.6$.

EXAMPLE 108

1-Methyl-2-[N-[4-(N-n-heptyloxycarbonylamidino) phenyl]aminomethyl]benzimidazol-5-yl-carboxylic acid-N-(2-pyridyl)-N-(2-methoxycarbonylethyl) amide Prepared analogously to Example 90 from 1-methyl-2-[N-(4-amidinophenyl)aminomethyl]benzimidazol-5-yl-carboxylic acid-N-(2-pyridyl)-N-(2-methoxycarbonylethyl) amide hydrochloride and n-heptyl chloroformate. Yield: 21% of theory, $C_{34}H_{41}N_7O_5$ (627.8); $R_f$ value: 0.60 (silica gel; dichloromethane/methanol=9:1); EKA mass spectrum: $(M+H)^+=628$; $(M+H+Na)^{++}=325.7$; $(M+2H)^{++}=314.7$.

EXAMPLE 109

1-Methyl-2-[N-[4-(N-n-pentyloxycarbonylamidino) phenyl]aminomethyl]benzimidazol-5-yl-carboxylic acid-N-(2-pyridyl)-N-(2-methoxycarbonylethyl) amide Prepared analogously to Example 90 from 1-methyl-2-[N-(4-amidinophenyl)aminomethyl]benzimidazol-5-yl-carboxylic acid-N-(2-pyridyl)-N-(2-methoxycarbonylethyl) amide hydrochloride and n-pentyl chloroformate. Yield: 66% of theory, $C_{32}H_{37}N_7O_5$ (599.7); $R_f$ value: 0.58 (silica gel; dichloromethane/methanol=9:1); EKA mass spectrum: $(M+H)^+=600$; $(M+H+Na)^{++}=311.7$; $(M+Na)^+=622$.

EXAMPLE 110

1-Methyl-2-[N-[4-(N-n-nonyloxycarbonylamidino) phenyl]aminomethyl]benzimidazol-5-yl-carboxylic acid-N-(2-pyridyl)-N-(2-methoxycarbonylethyl) amide Prepared analogously to Example 90 from 1-methyl-2-[N-(4-amidinophenyl)aminomethyl]benzimidazol-5-yl-carboxylic acid-N-(2-pyridyl)-N-(2-methoxycarbonylethyl) amide hydrochloride and n-nonyl chloroformate. Yield: 60% of theory, $C_{36}H_{45}N_7O_5$ (655.8); $R_f$ value: 0.48 (silica gel; dichloromethane/methanol=9:1); EKA mass spectrum: $(M+H)^+=656$; $(M+H+Na)^{++}=339.8$; $(M+Na)^+=678$.

EXAMPLE 111

1-Methyl-2-[N-[4-(N-benzoylamidino)phenyl] aminomethyl]benzimidazol-5-yl-carboxylic acid-N-(2-pyridyl)-N-(2-methoxycarbonylethyl)amide Prepared analogously to Example 90 from 1-methyl-2-[N-(4-amidinophenyl)aminomethyl]benzimidazol-5-yl-carboxylic acid-N-(2-pyridyl)-N-(2-methoxycarbonylethyl) amide hydrochloride and benzoyl chloride. Yield: 62% of theory, $C_{33}H_{31}N_7O_4$ (589.7); $R_f$ value: 0.50 (silica gel; dichloromethane/methanol=9:1); EKA mass spectrum: $(M+H)^+=590$; $(M+Na)^+=612$.

EXAMPLE 112

1-Methyl-2-[N-[4-(N-nicotinoylamidino)phenyl] aminomethyl]benzimidazol-5-yl-carboxylic acid-N-(2-pyridyl)-N-(2-methoxycarbonylethyl)amide Prepared analogously to Example 90 from 1-methyl-2-[N-(4-amidinophenyl)aminomethyl]benzimidazol-5-yl-carboxylic acid-N-(2-pyridyl)-N-(2-methoxycarbonylethyl) amide hydrochloride and nicotinic acid chloride. Yield: 40% of theory, $C_{32}H_{30}N_8O_4$ (590.7); $R_f$ value: 0.47 (silica gel; dichloromethane/methanol=9:1); EKA mass spectrum: $(M+H)^+=591$; $(M+H+Na)^{++}=307$; $(M+Na)^+=613$.

EXAMPLE 113

1-Methyl-[N-[4-(N-n-hexyloxycarbonylamidino) phenyl]aminomethyl]benzimidazol-5-yl-carboxylic acid-N-(2-pyridyl)-N-(2-ethoxycarbonylethyl)amide Prepared analogously to Example 90 from 1-methyl-2-[N-(4-amidinophenyl)aminomethyl]benzimidazol-5-yl-carboxylic acid-N-(2-pyridyl)-N-(2-ethoxycarbonylethyl) amide hydrochloride and n-hexyl chloroformate. Yield: 51% of theory, $C_{34}H_{41}N_7O_5$ (627.8); $R_f$ value: 0.53 (silica gel; dichloromethane/methanol=9:1); EKA mass spectrum: $(M+H)^+=628$; $(M+H+Na)^{++}=325.7$; $(M+2H)^{++}=314.7$.

EXAMPLE 114

1-Methyl-2-[N-[4-(N-n-octyloxycarbonylamidino) phenyl]aminomethyl]benzimidazol-5-yl-carboxylic acid-N-(2-pyridyl)-N-(2-ethoxycarbonylethyl)amide Prepared analogously to Example 90 from 1-methyl-2-[N-(4-amidinophenyl)aminomethyl]benzimidazol-5-yl-carboxylic acid-N-(2-pyridyl)-N-(2-ethoxycarbonylethyl) amide hydrochloride and n-octyl chloroformate. Yield: 57% of theory, $C_{36}H_{45}N_7O_5$ (655.8); $R_f$ value: 0.46 (silica gel; dichloromethane/methanol=9:1); EKA mass spectrum: $(M+H)^+=656$; $(M+H+Na)^{++}=339.7$; $(M+2H)^{++}=328.7$.

EXAMPLE 115

1-Methyl-2-[N-[4-[N-(2-methylsulfonylethyloxycarbonyl) amidino]phenyl] aminomethyl]-benzimidazol-5-yl-carboxylic acid-N-(2-pyridyl)-N-ethoxycarbonylmethylamide Prepared analogously to Example 90 from 1-methyl-2-[N-(4-amidinophenyl)aminomethyl]benzimidazol-5-yl-carboxylic acid-N-(2-pyridyl)-N-ethoxycarbonylmethylamide hydrochloride and 2-(methylsulfonyl)ethyl chloroformate. Yield: 72% of theory, $C_{30}H_{33}N_7O_7S$ (635.7); $R_f$ value: 0.23 (silica gel; dichloromethane/ethanol=19:1); EKA mass spectrum: $(M+H)^+=636$; $(M+H+Na)^{++}=329.8$.

EXAMPLE 116

1-Methyl-2-[N-[4-(N-cyclohexyloxycarbonylamidino)phenyl] aminomethyl]benzimidazol-5-yl-carboxylic acid-N-(2-pyridyl-N-methoxycarbonylmethylamide Prepared analogously to Example 90 from 1-methyl-2-[N-(4-amidinophenyl)aminomethyl]benzimidazol-5-yl-carboxylic acid-N-(2-pyridyl)-N-methoxycarbonylmethylamide hydrochloride and cyclohexyl chloroformate. Yield: 40% of theory, $C_{32}H_{35}N_7O_5$ (597.7); $R_f$ value: 0.26 (silica gel; dichloromethane/ethanol=19:1); EKA mass spectrum: $(M+H)^+=598$; $(M+Na)^+=620$.

EXAMPLE 117

1-Methyl-2-[N-[4-(N-methoxycarbonylamidino) phenyl]aminomethyl]benzimidazol-5-yl-carboxylic acid-N-(2-pyridyl)-N-ethoxycarbonylmethylamide Prepared analogously to Example 90 from 1-methyl-2-[N-(4-amidinophenyl)aminomethyl]benzimidazol-5-ylcarboxylic acid-N-(2-pyridyl)-N-ethoxycarbonylmethylamide hydrochloride and methyl chloroformate. Yield: 62% of theory, $C_{28}H_{29}N_7O_5$ (543.6); $R_f$ value: 0.19 (silica gel; dichloromethane/ethanol=19:1); EKA mass spectrum: $(M+H)^+=544$; $(M+H+Na)^{++}=283.8$; $(M+Na)^+=566$.

EXAMPLE 118

1-Methyl-2-[N-[4-(N-ethoxycarbonylamidino)phenyl]aminomethyl]benzimidazol-5-yl-carboxylic acid-N-(2-pyridyl)-N-methoxycarbonylmethylamide Prepared analogously to Example 90 from 1-methyl-2-[N-(4-amidinophenyl)aminomethyl]benzimidazol-5-yl-carboxylic acid-N-(2-pyridyl)-N-methoxycarbonylmethylamide hydrochloride and ethyl chloroformate. Yield: 42% of theory, $C_{28}H_{29}N_7O_5$ (543.6); $R_f$ value: 0.20 (silica gel; dichloromethane/ethanol=19:1); EKA mass spectrum: $(M+H)^+=544$.

EXAMPLE 119

1-Methyl-2-[N-[4-(N-n-octyloxycarbonylamidino)phenyl]aminomethyl]benzimidazol-5-yl-carboxylic acid-N-(3-pyridyl)-N-(2-ethoxycarbonylethyl)amide Prepared analogously to Example 90 from 1-methyl-2-[N-(4-amidinophenyl)aminomethyl]benzimidazol-5-yl-carboxylic acid-N-(3-pyridyl)-N-(2-ethoxycarbonylethyl)amide hydrochloride and n-octyl chloroformate. Yield: 35% of theory, $C_{36}H_{45}N_7O_5$ (655.8); $R_f$ value: 0.28 (silica gel; dichloromethane/ethanol=19:1); EKA mass spectrum: $(M+H)^+=656$; $(M+2H)^{++}=328.7$.

EXAMPLE 120

1-Methyl-2-[N-[4-(N-n-hexyloxycarbonylamidino)phenyl]-N-methylaminomethyl]benzimidazol-5-yl-carboxylic acid-N-(2-pyridyl)-N-(2-ethoxycarbonylethyl)amide Prepared analogously to Example 90 from 1-methyl-2-[N-(4-amidinophenyl)-N-methylaminomethyl]benzimidazol-5-yl-carboxylic acid-N-(2-pyridyl)-N-(2-ethoxycarbonylethyl)amide hydrochloride and n-hexyl chloroformate. Yield: 58% of theory, $C_{35}H_{43}N_7O_5$ (641.2); $R_f$ value: 0.42 (silica gel; dichloromethane/ethanol=19:1); EKA mass spectrum: $(M+H)^+=642$; $(M+H+Na)^{++}=332.7$.

EXAMPLE 121

1-Methyl-2-[N-[4-(N-n-octyloxycarbonylamidino)phenyl]-N-methylaminomethyl]benzimidazol-5-yl-carboxylic acid-N-(2-pyridyl)-N-(2-ethoxycarbonylethyl)amide Prepared analogously to Example 90 from 1-methyl-2-[N-(4-amidinophenyl)-N-methylaminomethyl]benzimidazol-5-yl-carboxylic acid-N-(2-pyridyl)-N-(2-ethoxycarbonylethyl)amide hydrochloride and n-octyl chloroformate. Yield: 36% of theory, $C_{37}H_{47}N_7O_5$ (669.8); EKA mass spectrum: $(M+H)^+=670$; $(M+H+Na)^{++}=346.8$; $(M+2H)^{++}=335.6$.

EXAMPLE 122

1-Methyl-2-[N-[4-(N-n-butyloxycarbonylamidino)phenyl]-N-methylaminomethyl]benzimidazol-5-yl-carboxylic acid-N-(2-pyridyl)-N-(2-ethoxycarbonylethyl)amide Prepared analogously to Example 90 from 1-methyl-2-[N-(4-amidinophenyl)-N-methylaminomethyl]benzimidazol-5-yl-carboxylic acid-N-(2-pyridyl)-N-(2-ethoxycarbonylethyl)amide hydrochloride and n-butyl chloroformate. Yield: 34% of theory, $C_{33}H_{39}N_7O_5$ (613.7); EKA mass spectrum: $(M+H)^+=614$; $(M+H+Na)^{++}=318.7$; $(M+Na)^+=636$.

EXAMPLE 123

1-Methyl-2-[N-[4-(N-benzoylamidino)phenyl]-N-methylaminomethyl]benzimidazol-5-yl-carboxylic acid-N-(2-pyridyl)-N-(2-ethoxycarbonylethyl)amide Prepared analogously to Example 90 from 1-methyl-2-[N-(4-amidinophenyl)-N-methylaminomethyl]benzimidazol-5-yl-carboxylic acid-N-(2-pyridyl)-N-(2-ethoxycarbonylethyl)amide hydrochloride and benzoyl chloride. Yield: 63% of theory, $C_{35}H_{35}N_7O_4$ (617.7); EKA mass spectrum: $(M+H)^+=618$; $(M+H+Na)^{++}=320.7$; $(M+Na)^+=640$.

EXAMPLE 124

1-Methyl-2-[(4-amidinophenyl)oxymethyl]benzimidazol-5-yl-(1-ethoxycarbonylmethylcyclohex-1-yl) ketone hydrochloride a) 4-Chlorophenyl(1-hydroxycarbonylmethylcyclohex-1-yl) ketone 8.4 g (40 mmol) of 3-(4-chlorobenzoyl)propionic acid were dissolved in 300 mL of tetrahydrofuran and 5.8 g (120 mmol) of sodium hydride (50–60% suspension in paraffin oil) were added in batches. Then the mixture was refluxed for 1.5 hours with stirring, after which 8.9 mL (60 mmol) of 1,5-diiodopentane were added dropwise and boiling was continued for a further three hours. After cooling, the solution was stirred into 200 mL of ice-water, then the tetrahydrofuran was distilled off in vacuo, the resulting aqueous solution was acidified with 2N hydrochloric acid and extracted three times with 150 mL of dichloromethane. The organic phase was dried and evaporated down, the crude product thus obtained was purified by column chromatography (500 g silica gel; eluant: dichloromethane with 1–2% ethanol). Yield: 6.2 g (55% of theory) of oily product, $C_{15}H_{17}ClO_3$ (280.8); $R_f$ value: 0.56 (silica gel; dichloromethane/ethanol=19:1).

b) 4-Chloro-3-nitrophenyl-(1-hydroxycarbonylmethylcyclohex-1-yl) ketone 7.0 g (25 mmol) of 4-chlorophenyl-(1-hydroxycarbonylmethylcyclohex-1-yl) ketone were added in batches, with stirring, at $-5°$ C. to $-10°$ C., to 80 mL of fuming nitric acid. The solution was then stirred for a further 10 minutes, then stirred into 200 mL of ice-water, the precipitated product was then washed with water and dried. Yield: 7.8 g (96% of theory), $C_{15}H_{16}ClNO_5$ (325.8); $R_f$ value: 0.41 (silica gel; petroleum ether/ethyl acetate 4:6).

c) 4-Methylamino-3-nitrophenyl-(1-hydroxycarbonylmethylcyclohex-1-yl) ketone 7.8 g (23.9 mmol) of 4-chloro-3-nitrophenyl-(1-hydroxycarbonylmethylcyclohex-1-yl) ketone were stirred in 100 mL of a 40% aqueous methylamine solution at room temperature for 14 hours, then diluted with about 150 mL of water and made slightly acidic with glacial acetic acid. The precipitated product was suction filtered, washed with water and dried. Yield: 7.1 g (93% of theory), $C_{16}H_{20}N_2O_5$ (320.4); $R_f$ value: 0.34 (silica gel; dichloromethane/ethanol=19:1).

d) 4-Methylamino-3-nitrophenyl-(1-methoxycarbonylmethylcyclohex-1-yl) ketone 4.9 g (15 mmol) of 4-methylamino-3-hydroxycarbonylmethylcyclohex-1-yl) ketone were dissolved in 100 mL of tetrahydrofuran, 2.4 g (15 mmol) of 1,1'-carbonyldiimidazole were added and the mixture was refluxed for 15 minutes. Then the solvent was evaporated off, 30 mL of methanol were added and the mixture was boiled for three hours with stirring. After the methanol had been distilled off, the crude product thus obtained was purified by column chromatography (250 g silica gel, eluant: dichloromethane with 1 to 5% ethanol). Yield: 2.4 g (48% of theory), $C_{17}H_{22}N_2O_5$ (334.4); $R_f$ value: 0.76 (silica gel; dichloromethane/ethanol=19:1).

e) 3-Amino-4-methylaminophenyl-(1-methoxycarbonylmethylcyclohex-1-yl) ketone 2.4 g (7.2 mmol) of 4-methylamino-3-nitrophenyl-(1-methoxycarbonylmethylcyclohex-1-yl) ketone were catalytically hydrogenated in 100 mL of methanol at room temperature under 5 bar hydrogen pressure (10% palladium on charcoal). The crude product thus obtained was further reacted without purification. Yield: 2.1 g (96% of theory); $R_f$ value: 0.34 (silica gel; dichloromethane/ethanol=19:1).

f) 3-(4-Cyanophenyloxyacetylamino)-4-methylaminophenyl-(1-methoxycarbonylmethylcyclohex-1-yl) ketone 620 mg (3.5 mmol) of 4-cyanophenyloxyacetic acid and 570 mg (3.5 mmol) of 1,1'-carbonylduimidazole were refluxed in 50 mL of tetrahydrofuran for 15 minutes. Then 1.0 g (3.28 mmol) of 3-amino-4-methylaminophenyl-(1-methoxycarbonylmethylcyclohex-1-yl) ketone were added and the mixture was boiled for a further 4 hours. Then the solvent was evaporated off and the crude product thus obtained was purified by column chromatography (150 g silica gel; eluant: dichloromethane with 0 to 2% ethanol). Yield: 1.4 g (93% of theory), $C_{26}H_{29}N_3O_5$ (463.5); $R_f$ value: 0.44 (silica gel; dichloromethane/ethanol=19:1).

g) 1-Methyl-2-[(4-cyanophenyl)oxymethyl]benzimidazol-5-yl-(1-methoxycarbonylmethylcyclohex-1-yl) ketone 1.4 g (3.02 mmol) of 3-(4-cyanophenyloxyacetylamino)-4-methylaminophenyl-(1-methoxycarbonylmethylcyclohex-1-yl) ketone were refluxed in 50 mL of glacial acetic acid for one hour. Then the glacial acetic acid was distilled off, the residue was mixed with 20 mL of water and made alkaline with concentrated ammonia. This solution was extracted three times with 20 mL of dichloromethane, the organic extracts were dried and evaporated down. The crude product thus obtained was purified by column chromatography (100 g silica gel; eluant: dichloromethane with 0 to 2% ethanol). Yield: 700 mg (52% of theory), $C_{26}H_{27}N_3O_4$ (445.5).

h) 1-Methyl-2-[(4-amidinophenyl)oxymethyl]benzimidazol-5-yl-(1-ethoxycarbonylmethylcyclohex-1-yl) ketone hydrochloride Prepared analogously to Example 25d from 700 mg (1.57 mmol) of 1-methyl-2-(4-cyanophenyloxymethyl) benzimidazol-5-yl-(1-methoxycarbonylmethylcyclohex-1-yl) ketone with ethanolic hydrochloric acid and ammonium carbonate. Yield: 390 mg (50% of theory), $C_{27}H_{32}N_4O_4$ (476.6); EKA mass spectrum: $(M+H)^+=477$; $^1$H-NMR spectrum ($d_6$-DMSO): 1.10 (t,3H); 1.0–2.15 (m,10H); 3.36 (s,3H); 3.90 (s,2H); 3.94 (q,2H); 5.60 (s,2H); 7.25–7.40 (m,3H); 7.56–7.75 (m,2H); 7.90 (d,2H); 9.20 (broad s,4H) ppm.

EXAMPLE 125

1-Methyl-2-[N-(4-amidinophenyl)aminomethyl] benzimidazol-5-yl-tert-butyl ketone hydrochloride Prepared analogously to Example 25d from 1-methyl-2-[N-(4-cyanophenyl)aminomethyl]benzimidazol-5-yl-tert-butyl ketone, ethanolic hydrochloric acid, ethanol, and ammonium carbonate. Yield: 59% of theory, $C_{21}H_{25}N_5O$ (363.5); EKA mass spectrum: $(M+H)^+=364$.

EXAMPLE 126

1-Methyl-2-[N-(4-amidinophenyl)aminomethyl] benzimidazol-5-yl-(1-methylcyclopent-1-yl) ketone hydrochloride Prepared analogously to Example 25d from 1-methyl-2-[N-(4-cyanophenyl)aminomethyl]benzimidazol-5-yl-(1-methylcyclopent-1-yl) ketone, ethanolic hydrochloric acid, ethanol, and ammonium carbonate. Yield: 63.5% of theory, $C_{23}H_{27}N_5O$ (389.5); EKA mass spectrum: $(M+H)^+=390$.

EXAMPLE 127

2-[(4-amidinophenyl)sulfinylmethyl]benzothiazol-5-yl-carboxylic acid-N-phenyl-N-(2-ethoxycarbonylethyl)amide hydrochloride A solution of 0.15 g (0.27 mmol) of 2-[(4-amidinophenyl) thiomethyl]benzothiazol-5-yl-carboxylic acid-N-phenyl-N-(2-ethoxycarbonylethyl)amide hydrochloride in 10 mL of acetic acid was mixed with 0.09 mL (about 0.81 mmol) of 30% hydrogen peroxide solution and stirred at room temperature. After 4 days, a further 0.18 mL of hydrogen peroxide solution was added and the resulting mixture was stirred for a further two days. After removal of the solvent in vacuo, the crude product obtained was purified by flash chromatography (silica gel; methylene chloride/ethanol=10:1 to 4:1). Yield: 58% of theory, $C_{27}H_{26}N_4O_4S_2$ (534.66); $R_f$ value: 0.24 (silica gel; methylene chloride/ethanol=4:1+a few drops of acetic acid); EKA mass spectrum: $(M+H)^+=535$.

EXAMPLE 128

1-Methyl-2-[(4-amidinophenyl)sulfonylmethyl] benzimidazol-5-yl-carboxylic acid-N-(n-propyl)-N-(2-ethoxycarbonylethyl)amide hydrochloride A solution of 0.40 g (0.70 mmol) of 1-methyl-2-[(4-amidinophenyl)thiomethyl]benzimidazol-5-yl-carboxylic acid-N-(n-propyl)-N-(2-ethoxycarbonylethyl)amide hydrochloride in 10 mL of formic acid was mixed with 2 mL of 30% hydrogen peroxide solution and the mixture was stirred for 16 hours at room temperature. Then the solvent was distilled off in vacuo, whereupon the desired compound was obtained as a beige solid (contaminated with some 1-methyl-2-[(4-amidinophenyl)sulfinylmethyl]benzimidazol-5-yl-carboxylic acid-N-(n-propyl)-N-(2-ethoxycarbonylethyl) amide hydrochloride). Yield: 95% of theory, $C_{25}H_{31}N_6O_5S$ (513.62); $R_f$ value: 0.50 (silica gel; ethyl acetate/ethanol/1N hydrochloric acid=50:45:5); EKA mass spectrum: $(M+H)^+=514$.

EXAMPLE 129

2-[N-(4-amidinophenyl)aminomethyl]thiazolo[5,4-b]
pyridin-6-yl-carboxylic acid-N-phenyl-N-(2-
ethoxycarbonylethyl)amide hydrochloride a) Methyl 5-amino-6-chloronicotinate A solution of 1.08 g (5.00 mmol) of methyl 6-chloro-5-nitronicotinate (see A. H. Berrie, G. T. Newbold, and F. S. Spring in J. Chem. Soc., 2590, 1951) in 25 mL of absolute ethanol was mixed successively with 0.53 mL (29 mmol) of water, 3.2 g (57 mmol) of iron powder and 0.030 mL of concentrated hydrochloric acid and heated to boiling for one hour. Then equal quantities of water, iron powder and hydrochloric acid were added and the mixture was heated to boiling for 30 minutes. The precipitate formed on cooling was filtered off and washed with ethanol and the solvent was distilled off in vacuo. Yield: 0.75 g (81% of theory) of greenish-yellow solid, $C_7H_7ClN_2O_2$ (186.60); $R_f$ value: 0.31 (silica gel; ethyl acetate/petroleum ether=1:4); YEF-Mass spectrum: $M^+$=186 and 188 (chlorine isotopes).

b) Methyl 6-chloro-5-methoxyacetamidonicotinate

A solution of 0.75 g (4.02 mmol) of methyl 5-amino-6-chloronicotinate and 0.43 g=0.35 mL (4.5 mmol) of methoxyacetylchloride in 20 mL of chlorobenzene was stirred for one hour at 110° C. After the solvent had been removed in vacuo, the crude product obtained was purified by flash chromatography (silica gel; methylene chloride/ethanol=100:1), evaporated down again in vacuo and then digested with petroleum ether. Yield: 0.55 g (53% of theory) light yellow amorphous solid; $R_f$ value: 0.33 (silica gel; ethyl acetate/petroleum ether=1:4).

c) Methyl 2-methoxymethylthiazolo[5,4-b]pyridin-6-yl-carboxylate

A mixture of 0.53 g (2.05 mmol) of methyl 6-chloro-5-methoxyacetamidonicotinate and 0.42 g (1.0 mmol) of Lawesson's reagent was refluxed for 16 hours in 25 mL of xylene. After the solvent had been removed in vacuo, the crude product obtained was purified by flash chromatography (silica gel; methylene chloride/ethanol=100:1) and evaporated down again in vacuo. Yield: 0.33 g (67% of theory) of yellow amorphous solid; $R_f$ value: 0.52 (silica gel; ethyl acetate/petroleum ether=1:4).

d) 2-Methoxymethylthiazolo[5,4-b]pyridin-6-yl-carboxylic acid

A mixture of 1.1 g (4.62 mmol) of methyl-2-methoxymethylthiazolo[5,4-b]pyridine-6-carboxylate and 9.2 mL of 2N sodium hydroxide solution were stirred into 50 mL of ethanol for one hour at room temperature. Then 9.2 mL of 2N hydrochloric acid were added, the alcohol was distilled off, and it was diluted with 20 mL of water. The aqueous phase was acidified with concentrated hydrochloric acid whilst cooling with ice, the beige precipitate formed was filtered off, then washed with water and dried. Yield: 1.03 g (100% of theory); $R_f$ value: 0.10 (silica gel; ethyl acetate/petroleum ether=3:7).

e) 2-Methoxymethylthiazolo[5,4-b]pyridin-6-yl-carboxylic acid-N-phenyl-N-(2-ethoxycarbonylethyl)amide A suspension of 1.03 g (4.62 mmol) of 2-methoxymethylthiazolo[5,4-b]pyridin-6-yl-carboxylic acid in 40 mL of methylene chloride was mixed with 1.6 g=1.0 mL (13.5 mmol) of thionyl chloride and refluxed for 90 minutes, during which time the solid gradually dissolved. After the liquid components had been distilled off, the crude product was taken up twice more in methylene chloride and concentrated again. The resulting crude acid chloride (1.2 g) was taken up in 40 mL of tetrahydrofuran, added dropwise to a mixture of 0.94 g (4.86 mmol) of N-(2-ethoxycarbonylethyl)aniline and 2.1 mL (13.8 mmol) of triethylamine in 30 mL of tetrahydrofuran and stirred for 2 hours at room temperature. Then it was diluted with 200 mL of ethyl acetate, washed with 100 mL of 14% saline solution, and the organic phase was dried with sodium sulfate. After the solvent had been removed in vacuo, the crude product obtained was purified by flash chromatography (silica gel; methylene chloride/ethanol=100:1). Yield: 1.57 g (87% of theory)of yellow oil; $R_f$ value: 0.55 (silica gel; methylene chloride/ethanol=19:1).

f) 2-[N-(4-Cyanophenyl)aminomethyl]thiazolo[5,4-b]pyridin-6-yl-carboxylic acid-N-phenyl-N-(2-ethoxycarbonylethyl)amide A mixture of 1.54 g (3.85 mmol) of 2-methoxymethylthiazolo[5,4-b]pyridin-6-yl-carboxylic acid-N-phenyl-N-(2-ethoxycarbonylethyl)amide and 4.3 mL (4.3 mmol) of a 1 molar solution of boron tribromide in methylene chloride was dissolved in a further 30 mL of methylene chloride and stirred for 5 hours at room temperature. Then the mixture was washed with 40 mL of saturated sodium hydrogen carbonate solution, the organic phase was dried with sodium sulfate, and the solvent was distilled off. The crude product (1.9 g) was taken up in 15.0 mL of N,N-diisopropylethylamine, mixed with 0.50 g (4.2 mmol) of 4-aminobenzonitrile, and heated to boiling for one hour. Then the solvent was distilled off in vacuo, the crude product was taken up in 100 mL of methylene chloride, the organic phase was washed with 100 mL of water, and dried with sodium sulfate. After the solvent had been removed in vacuo, the crude product obtained was purified by flash chromatography (silica gel; ethyl acetate/petroleum ether= 35:65 to 1:1) and evaporated down again in vacuo. Yield: 0.45 g (24% of theory) of yellow amorphous solid; $R_f$ value: 0.34 (silica gel; ethyl acetate/petroleum ether=1:1).

g) 2-[N-(4-amidinophenyl)aminomethyl]thiazolo[5,4-b]pyridin-6-yl-carboxylic acid-N-phenyl-N-(2-ethoxycarbonylethyl)amide hydrochloride 0.39 g (0.803 mmol) of 2-[N-(4-cyanophenyl)aminomethyl]thiazolo[5,4-b]pyridin-6-yl-carboxylic acid-N-phenyl-N-(2-ethoxycarbonylethyl)amide were stirred in 40 mL of ethanol saturated with hydrogen chloride for 5 hours first at 0° C. and then at room temperature, until no more starting material could be detected by thin layer chromatography. Then the solvent was distilled off at a maximum bath temperature of 30° C., the oily residue was taken up in 40 mL of absolute ethanol and mixed with 0.5 g ammonium carbonate. After 18 hours, the solvent was removed in vacuo and the crude product obtained was purified by flash chromatography (silica gel; methylene chloride/ethanol=9:1 to 4:1). Yield: 78% of theory of yellow foam, $C_{26}H_{26}N_6O_3S$ (502.60); $R_f$ value: 0.19 (silica gel; methylene chloride/ethanol=4:1+a few drops of acetic acid); EKA mass spectrum: $(M+H)^+$=503.

EXAMPLE 130

1-Methyl-2-[(4-amidinophenyl)methylthio]
benzimidazol-5-yl-carboxylic acid-N-phenyl-N-(2-
ethoxycarbonylethyl)amide hydrochloride a) 1-Methyl-2-mercaptobenzimidazol-5-yl-carboxylic acid-N-phenyl-N-(2-ethoxycarbonylethyl)amide A solution of 6.5 g (19 mmol) of 3-amino-4-methylaminobenzoic acid-N-phenyl-N-(2-ethoxycarbonylethyl)amide and 4.5 g (22.8 mmol) of N,N'-thiocarbonyldiimidazole were dissolved in 100 mL of tetrahydrofuran under a nitrogen atmosphere, the solution was heated to 90° C. for 4 hours and left to stand for 16 hours at room temperature. After removal of the solvent in vacuo, the crude product obtained was purified by flash chromatography (silica gel; petroleum ether/ethyl acetate=100:0 to 65:35). Yield: 6.8 g (93% of theory) of beige crystalline solid; $R_f$ value: 0.55 (silica gel; ethyl acetate).

b) 1-Methyl-2-[(4-cyanophenyl)methylthio]benzimidazol-5-yl-carboxylic acid-N-phenyl-N-(2-ethoxycarbonylethyl)amide A solution of 1.30 g (3.4 mmol) of 1-methyl-2-mercaptobenzimidazol-5-yl-carboxylic acid-N-phenyl-N-(2-ethoxycarbonylethyl)amide, 0.52 g (3.74 mmol) of potassium carbonate and 0.66 g (3.4 mmol) of 4-bromomethylbenzonitrile were dissolved in 40 mL of absolute ethanol, stirred for 4 hours at 60° C. and 16 hours at room temperature. Then the solvent was distilled off in vacuo, the crude product was taken up in 30 mL of methylene chloride, washed with 40 mL of water and dried with sodium sulfate. After filtration and distillation of the solvent, the desired compound was obtained as a beige-white solid. Yield: 1.8 g (100% of theory); $R_f$ value: 0.64 (silica gel; ethyl acetate).

c) 1-Methyl-2-[(4-amidinophenyl)methylthio]benzimidazol-5-yl-carboxylic acid-N-phenyl-(2-ethoxycarbonylethyl)amide hydrochloride 1.5 g (3.0 mmol) of 1-methyl-2-[(4-cyanophenyl)methylthio]benzimidazol-5-yl-carboxylic acid-N-phenyl-N-(2-ethoxycarbonylethyl)amide were stirred in 80 mL of ethanol saturated with hydrogen chloride for 6.5 hours first at 0° C., then at room temperature, until no more starting material could be detected by thin layer chromatography. Then the solvent was distilled off at a maximum bath temperature of 30° C., the oily residue taken up in 80 mL of absolute ethanol and mixed with 1.0 g (10.5 mmol) of ammonium carbonate. After 18 hours, the solvent was distilled off in vacuo and the crude product obtained was purified by flash chromatography (silica gel; methylene chloride/ethanol=19:1 to 10:1). Yield: 78% of theory of light beige solid, $C_{28}H_{29}N_5O_3S$ (515.63); $R_f$ value: 0.19 (silica gel; methylene chloride/ethanol=4:1); EKA mass spectrum: $(M+H)^+=516$; $(M+H+Na)^{++}=269.7$; $(M+2H)^{++}=258.7$.

EXAMPLE 131

1-Methyl-2-[(4-amidinophenyl)methylthio]benzimidazol-5-yl-carboxylic acid-N-phenyl-N-(2-hydroxycarbonylethyl)amide hydrochloride Prepared analogously to Example 10 from 1-methyl-2-[(4-amidinophenyl)methylthio]benzimidazol-5-yl-carboxylic acid-N-phenyl-N-(2-ethoxycarbonylethyl)amide hydrochloride and sodium hydroxide solution. Yield: 57% of theory, $C_{26}H_{25}N_5O_3S$ (487.58); $R_f$ value: 0.23 (Reversed Phase silica gel RP-8; Methanol/5% saline solution=6:4); EKA mass spectrum: $(M+H)^+=488$; $(M+Na)^+=510$; $(M+Na+H)^{++}=255.6$.

EXAMPLE 132

1-Methyl-2-[N-(4-amidinophenyl)aminomethyl]benzimidazol-5-yl-carboxylic acid-N-propargyl-N-(2-ethoxycarbonylethyl)amide hydrochloride Prepared analogously to Example 25d from 1-methyl-2-[N-(4-cyanophenyl)aminomethyl]benzimidazol-5-yl-carboxylic acid-N-propargyl-N-(2-ethoxycarbonylethyl)amide, ethanolic hydrochloric acid, ethanol, and ammonium carbonate. Yield: 81% of theory, $C_{25}H_{28}N_6O_3$ (460.6); $R_f$ value: 0.094 (silica gel; dichloromethane/ethanol=4:1); EKA mass spectrum: $(M+H)^+=461$; $(M+H+Na)^{++}=242$; $(M+2H)^{++}=231$.

EXAMPLE 133

1-Methyl-2-[2-[4-(N-n-hexyloxycarbonylamidino)phenyl]ethyl]benzimidazol-5-yl-carboxylic acid-N-(2-pyridyl)-N-(2-ethoxycarbonylethyl)amide Prepared analogously to Example 90 from 1-methyl-2-[2-(4-amidinophenyl)ethyl]benzimidazol-5-yl-carboxylic acid-N-(2-pyridyl)-N-(2-ethoxycarbonylethyl)amide hydrochloride and n-hexyl chloroformate. Yield: 72% of theory, $C_{35}H_{42}N_6O_5$ (626.8); $R_f$ value: 0.54 (silica gel; dichloromethane/methanol=9:1); EKA mass spectrum: $(M+H)^+=627$; $(M+Na)^{+-}649$.

EXAMPLE 134

1-Methyl-2-[2-[4-(N-benzoylamidino)phenyl]ethyl]benzimidazol-5-yl-carboxylic acid-N-(2-pyridyl)-N-(2-ethoxycarbonylethyl)amide Prepared analogously to Example 90 from 1-methyl-2-[2-(4-amidinophenyl)ethyl]benzimidazol-5-yl-carboxylic acid-N-(2-pyridyl)-N-(2-ethoxycarbonylethyl)amide hydrochloride and benzoyl chloride. Yield: 79% of theory, $C_{35}H_{34}N_6O_4$ (602.7); $R_f$ value: 0.52 (silica gel; dichloromethane/methanol=9:1); EKA mass spectrum: $(M+H)^+=603$; $(M+Na)^+=625$.

EXAMPLE 135

1-Methyl-2-[2-[4-(N-nicotinoylamidino)phenyl]ethyl]benzimidazol-5-yl-carboxylic acid-N-(2-pyridyl)-N-(2-ethoxycarbonylethyl)amide Prepared analogously to Example 90 from 1-methyl-2-[2-(4-amidinophenyl)ethyl]benzimidazol-5-yl-carboxylic acid-N-(2-pyridyl)-N-(2-ethoxycarbonylethyl)amide hydrochloride and nicotinic acid chloride. Yield: 56% of theory, $C_{34}H_{33}N_7O_4$ (603.7); $R_f$ value: 0.52 (silica gel; dichloromethane/methanol=9:1); EKA mass spectrum: $(M+H)^+=604$; $(M+Na)^+=626$.

EXAMPLE 136

1-Cyclopropyl-2-[N-(4-amidinophenyl)aminomethyl]benzimidazol-5-yl-carboxylic acid-N-phenyl-N-(2-ethoxycarbonylethyl)amide hydrochloride Prepared analogously to Example 25d from 1-cyclopropyl-2-[N-(4-cyanophenyl)aminomethyl]benzimidazol-5-yl-carboxylic acid-N-phenyl-N-(2-ethoxycarbonylethyl)amide, ethanolic hydrochloric acid, ethanol, and ammonium carbonate. Yield: 31% of theory, $C_{30}H_{33}N_6O_3$ (524.6); $R_f$ value: 0.40 (silica gel; dichloromethane/methanol=5:1); EKA mass spectrum: $(M+H)^+=525$; $(M+H+Na)^{++}=274$; $(M+2H)^{++}=263$.

EXAMPLE 137

1-Cyclopropyl-2-[N-(4-amidinophenyl)aminomethyl]benzimidazol-5-yl-carboxylic acid-N-phenyl-N-(2-hydroxycarbonylethyl)amide Prepared analogously to Example 26 from 1-cyclopropyl-2-[N-(4-amidinophenyl)aminomethyl]benzimidazol-5-yl-carboxylic acid-N-phenyl-N-(2-ethoxycarbonylethyl)amide hydrochloride and sodium hydroxide solution. Yield: 64% of theory, $C_{28}H_{28}N_6O_3$ (496.6); EKA mass spectrum: $(M+H)^+=497$; $(M+H+Na)^{++}=260$; $(M+Na)^+=519$; $(M+2Na)^{++}=271$.

EXAMPLE 138

1-Methyl-2-[N-(4-amidinophenyl)-N-(n-butyl)aminomethyl]benzimidazol-5-yl-carboxylic acid-N-phenyl-N-(2-ethoxycarbonylethyl)amide hydrochloride Prepared analogously to Example 25d from 1-methyl-2-[N-(4-cyanophenyl)-N-(n-butyl)aminomethyl]

benzimidazol-5-yl-carboxylic acid-N-phenyl-N-(2-ethoxycarbonylethyl)amide, ethanolic hydrochloric acid, ethanol, and ammonium carbonate. Yield: 62% of theory, $C_{32}H_{38}N_6O_3$ (554.7); EKA mass spectrum: $(M+H)^+=555$; $(M+H+Na)^{++}=289$; $(M+2H)^{++}=278$.

EXAMPLE 139

1-Methyl-2-[N-(4-amidino-2-chlorophenyl)aminomethyl]benzimidazol-5-yl-carboxylic acid-N-phenyl-N-(2-ethoxycarbonylethyl)amide hydrochloride Prepared analogously to Example 25d from 1-methyl-2-[N-(4-cyano-2-chlorophenyl)aminomethyl]benzimidazol-5-yl-carboxylic acid-N-phenyl-N-(2-ethoxycarbonylethyl)amide, ethanolic hydrochloric acid, ethanol, and ammonium carbonate. Yield: 82% of theory, $C_{28}H_{29}ClN_6O_3$ (533.1); EKA mass spectrum: $(M+H)^+=533/5$; $(M+H+Na)^{++}=278/9$.

EXAMPLE 140

1-Methyl-2-[N-[4-(n-octyloxycarbonylamidino)phenyl]aminomethyl]benzimidazol-5-yl-carboxylic acid-N-phenyl-N-(2-ethoxycarbonylethyl)amide Prepared analogously to Example 90 from 1-methyl-2-[N-(4-amidinophenyl)aminomethyl]benzimidazol-5-yl-carboxylic acid-N-phenyl-N-(2-ethoxycarbonylethyl)amide hydrochloride and n-octyl chloroformate. Yield: 34% of theory, $C_{37}H_{46}N_6O_5$ (654.8); $R_f$ value: 0.15 (silica gel; dichloromethane/ethanol=19:1); EKA mass spectrum: $(M+H)^+=655$; $(M+H+Na)^{++}=339$; $(M+Na)^+=677$.

EXAMPLE 141

1-Methyl-2-[N-(4-amidino-2-ethylphenyl)aminomethyl]benzimidazol-5-yl-carboxylic acid-N-phenyl-N-(2-ethoxycarbonylethyl)amide hydrochloride Prepared analogously to Example 25d from 1-methyl-2-[N-(4-cyano-2-ethylphenyl)aminomethyl]benzimidazol-5-yl-carboxylic acid-N-phenyl-N-(2-ethoxycarbonylethyl)amide, ethanolic hydrochloric acid, ethanol, and ammonium carbonate. Yield: 61% of theory, $C_{30}H_{34}N_6O_3$ (526.6); EKA mass spectrum: $(M+H)^+=527$; $(M+H+Na)^{++}=275$; $(M+2H)^{++}=264$.

EXAMPLE 142

1-Methyl-2-[N-(4-amidinophenyl)aminomethyl]benzimidazol-5-yl-carboxylic acid-benzylamide hydrochloride Prepared analogously to Example 25d from 1-methyl-2-[N-(4-cyanophenyl)aminomethyl]benzimidazol-5-yl-carboxylic acid-benzylamide, ethanolic hydrochloric acid, ethanol, and ammonium carbonate. Yield: 63% of theory, $C_{24}H_{24}N_6O$ (412.5); $R_f$ value: 0.76 (silica gel; dichloromethane/ethanol=4:1); EKA mass spectrum: $(M+H)^+=413$.

EXAMPLE 143

1-Methyl-2-[N-[4-(N-(2-(2-ethoxyethoxy)ethyloxy)carbonylamidino)phenyl]aminomethyl]benzimidazol-5-yl-carboxylic acid-N-(2-pyridyl)-N-(2-ethoxycarbonylethyl)amide Prepared analogously to Example 90 from 1-methyl-2-[N-(4-amidinophenyl)aminomethyl]benzimidazol-5-yl-carboxylic acid-N-(2-pyridyl)-N-(2-ethoxycarbonylethyl)amide hydrochloride and diethyleneglycolmonoethylether chloroformate. Yield: 43% of theory, $C_{34}H_{41}N_7O_7$ (659.8); $R_f$ value: 0.56 (silica gel; dichloromethane/methanol=9:1); EKA mass spectrum: $(M+H)^+=660$; $(M+H+Na)^{++}=341.7$.

EXAMPLE 144

1-Methyl-2-[N-(4-amidinophenyl)aminomethyl]benzimidazol-5-yl-carboxylic acid-N-(1-methylpyrazol-4-yl)-N-(2-ethoxycarbonylethyl)amide hydrochloride Prepared analogously to Example 25d from 1-methyl-2-[N-(4-cyanophenyl)aminomethyl]benzimidazol-5-yl-carboxylic acid-N-(2-pyridyl)-N-(2-ethoxycarbonylethyl)amide, ethanolic hydrochloric acid, ethanol, and ammonium carbonate. Yield: 60% of theory, $C_{26}H_{30}N_8O_3$ (502.6); $R_f$ value: 0.13 (silica gel; dichloromethane/ethanol=4:1); EKA mass spectrum: $(M+H)^+=503$; $(M+H+Na)^{++}=263$; $(M+2H)^{++}=252$.

EXAMPLE 145

3-Methyl-2-[(4-amidinophenyl)thiomethyl]imidazo[4,5-b]pyridin-6-yl-carboxylic acid-N-phenyl-N-(2-ethoxycarbonylethyl)amide hydrochloride Prepared analogously to Example 1 from 3-methyl-2-[(4-cyanophenyl)thiomethyl]imidazo[4,5-b]pyridin-6-yl-carboxylic acid-N-phenyl-N-(2-methoxycarbonylethyl)amide, ethanolic hydrochloric acid, ethanol, and ammonium carbonate. Yield: 88% of theory, $C_{27}H_{28}N_6O_3S$ (516.63); $R_f$ value: 0.23 (silica gel; ethyl acetate/ethanol/ammonia=50:45:5); EKA mass spectrum: $(M+H)^+=517$; $(M+H+Na)^{++}=270$.

EXAMPLE 146

3-Methyl-2-[N-(4-amidinophenyl)aminomethyl]imidazo[4,5-b]pyridin-6-yl-carboxylic acid-N-phenyl-N-(2-ethoxycarbonylethyl)amide hydrochloride Prepared analogously to Example 1 from 3-methyl-2-[N-(4-cyanophenyl)aminomethyl]imidazo[4,5-b]pyridin-6-yl-carboxylic acid-N-phenyl-N-(2-methoxycarbonylethyl)amide, ethanolic hydrochloric acid, ethanol, and ammonium carbonate. Yield: 82% of theory, $C_{27}H_{29}N_7O_3$ (499.58); $R_f$ value: 0.20 (silica gel; ethyl acetate/ethanol/ammonia=50:45:5); EKA mass spectrum: $(M+H)^+=500$; $(M+H+Na)^{++}=261.7$.

EXAMPLE 147

3-Methyl-2-[(4-amidinophenyl)thiomethyl]imidazo[4,5-b]pyridin-6-yl-carboxylic acid-N-phenyl-N-(2-hydroxycarbonylethyl)amide hydrochloride Prepared analogously to Example 2 from 3-methyl-2-[(4-amidinophenyl)thiomethyl]imidazo[4,5-b]pyridin-6-yl-carboxylic acid-N-phenyl-N-(2-ethoxycarbonylethyl)amide hydrochloride and sodium hydroxide solution. Yield: 88% of theory, $C_{25}H_{24}N_6O_3S$ (488.56); $R_f$ value: 0.21 (silica gel; ethyl acetate/ethanol/ammonia=50:45:5); EKA mass spectrum: $(M+H)^+=489$; $(M+Na)^+=511$.

EXAMPLE 148

3-Methyl-2-[N-(4-amidinophenyl)aminomethyl]imidazo[4,5-b]pyridin-6-yl-carboxylic acid-N-phenyl-N-(2-hydroxycarbonylethyl)amide hydrochloride Prepared analogously to Example 2 from 3-methyl-2-[N-(4-amidinophenyl)aminomethyl]imidazo[4,5-b]pyridin-6- yl-carboxylic acid-N-phenyl-N-(2-ethoxycarbonylethyl) amide hydrochloride and sodium hydroxide solution. Yield: 80% of theory, $C_{25}H_{25}N_7O_3$ (471.52); $R_f$ value: 0.19 (silica gel; ethyl acetate/ethanol/ammonia=50:45:5); EKA mass spectrum: $(M+H)^+=472$; $(M+Na)^+=494$; $(M+2Na)^{++}=258.6$.

EXAMPLE 149

1-Methyl-2-[N-(4-amidinophenyl)aminomethyl] benzimidazol-5-yl-sulfonic acid-N-phenyl-N-(2-ethoxycarbonylethyl)amide hydrochloride a) 1-Methyl-2[N-(4-cyanophenyl)aminomethyl] benzimidazol-5-yl-sulfonic acid-N-phenyl-N-(2-ethoxycarbonylethyl)amide 2.54 g (6.2 mmol) of 3-nitro-4-methylaminobenzenesulfonic acid-N-phenyl-N-(2-ethoxycarbonylethyl)amide were hydrogenated at room temperature under 5 bar hydrogen pressure over palladium/charcoal (10%) in a mixture of 75 mL of ethanol and 75 mL of dichloromethane. The resulting crude 3-amino-4-methylaminobenzenesulfonic acid-N-phenyl-N-(2-ethoxycarbonylethyl)amide was taken up in 30 mL of phosphorus oxychloride, without purification, then 1.1 g (6.2 mmol) of N-(4-cyanophenyl)glycine were added and the mixture was refluxed for two hours. After cooling to room temperature, the reaction mixture was added to about 70 mL of water with cooling and in this way the excess phosphorus oxychloride was destroyed. The resulting solution was neutralized with solid sodium carbonate and extracted three times with 30 mL of ethyl acetate. After evaporation of the solvent, the crude product was purified by column chromatography (100 g silica gel; eluant: cyclohexane/ethyl acetate=2:3). Yield: 860 mg (26.8% of theory), $C_{27}H_{27}N_5O_3S$ (517.6); melting point: 188° C.–191° C.; $R_f$ value: 0.52 (silica gel; dichloromethane/methanol=9:1); EKA mass spectrum: $(M+H)^+=518$; $(M+Na)^+=540$.

b) 1-Methyl-2-[N-(4-amidinophenyl)aminomethyl] benzimidazol-5-yl-sulfonic acid-N-phenyl-N-(2-ethoxycarbonylethyl)amide hydrochloride Prepared analogously to Example 25d from 1-methyl-2-[N-(4-cyanophenyl)aminomethyl]benzimidazol-5-yl-sulfonic acid-N-phenyl-N-(2-ethoxycarbonylethyl)amide, ethanolic hydrochloric acid, ethanol, and ammonium carbonate. Yield: 87% of theory, $C_{27}H_{30}N_6O_4S$ (534.6); $R_f$ value: 0.13 (silica gel; dichloromethane/ethanol=9:1); EKA mass spectrum: $(M+H)^+=535$; $(M+H+Na)^{++}=279$.

EXAMPLE 150

1-Methyl-2-[N-(4-amidinophenyl)aminomethyl] benzimidazol-5-yl-sulfonic acid-N-(1-methylpyrazol-4-yl)-N-(2-ethoxycarbonylethyl) amide hydrochloride Prepared analogously to Example 25d from 1-methyl-2-[N-(4-cyanophenyl)aminomethyl]benzimidazol-5-yl-sulfonic acid-N-(1-methylpyrazol-4-yl)-N-(2-ethoxycarbonylethyl)amide, ethanolic hydrochloric acid, ethanol, and ammonium carbonate. Yield: 38% of theory, $C_{25}H_{30}N_8O_4S$ (538.6); $R_f$ value: 0.09 (silica gel; dichloromethane/ethanol=9:1); EKA mass spectrum: $(M+H)^+=539$.

EXAMPLE 151

1-Methyl-2-[N-(4-amidinophenyl)aminomethyl]-5-(2,3-dihydroindol-1-yl-sulfonyl)benzimidazole hydrochloride Prepared analogously to Example 25d from 1-methyl-2-[N-(4-cyanophenyl)aminomethyl]-5-(2,3-dihydroindol-1-yl-sulfonyl)benzimidazole and ethanolic hydrochloric acid, ethanol, and ammonium carbonate. Yield: 15% of theory, $C_{24}H_{24}N_6O_2S$ (460.6); $R_f$ value: 0.36 (silica gel; dichloromethane/methanol=4:1); EKA mass spectrum: $(M+H)^+=461$.

EXAMPLE 152

1-Methyl-2-[N-(4-amidinophenyl)aminomethyl] benzimidazole-5-yl-sulfonic acid-N-phenyl-N-(2-hydroxycarbonylethyl)amide Prepared analogously to Example 26 from 1-methyl-2-[N-(4-amidinophenyl)aminomethyl]benzimidazol-5-yl-sulfonic acid-N-phenyl-N-(2-ethoxycarbonylethyl)amide hydrochloride and sodium hydroxide solution. Yield: 24% of theory, $C_{25}H_{26}N_6O_4S$ (506.6); $R_f$ value: 0.55 (Reverse-Phase RP-18 silica gel; methanol/5% saline solution=3:2); EKA mass spectrum: $(M+H)^+=507$; $(M+Na)^+=529$; $(M+2Na)^{++}=276$.

EXAMPLE 153

1-Methyl-2-[N-(4-amidinophenyl)aminomethyl]-5-(isoindolin-2-yl-sulfonyl)benzimidazole hydrochloride Prepared analogously to Example 25d from 1-methyl-2-[N-(4-cyanophenyl)aminomethyl]-5-(isoindolin-2-yl-sulfonyl)benzimidazole and ethanolic hydrochloric acid, ethanol, and ammonium carbonate. Yield: 33% of theory, $C_{24}H_{24}N_6O_2S$ (460.6); $R_f$ value: 0.32 (silica gel; dichloromethane/methanol=4:1); EKA mass spectrum: $(M+H)^+=461$.

EXAMPLE 154

2-[2-(4-Amidinophenyl)ethyl]quinazolin-7-yl-carboxylic acid-N-phenyl-N-(2-ethoxycarbonylethyl)amide hydrochloride a. Ethyl 4-methyl-3-nitrobenzoate To a solution of 3 mL of concentrated hydrochloric acid and 4 mL of concentrated sulfuric acid, 4.9 g (0.03 mol) of ethyl p-tolylate were added dropwise with stirring at 5° C. and stirred for 1 hour whilst cooling in an ice-bath. After heating to ambient temperature, the mixture was poured onto ice-water and extracted with ethyl acetate. The organic extracts were washed with sodium hydrogen carbonate solution, dried, and evaporated down. Yield: 5.7 g (90% of theory); $R_f$ value: 0.81 (silica gel, ethyl acetate/cyclohexane=1:1).

b. Methyl 4-(2-dimethylaminovinyl)-3-nitrobenzoate 1.0 g (4.8 mmol) of ethyl 4-methyl-3-nitrobenzoate, 0.74 g (6.2 mmol) of dimethylformamide dimethylacetal and 2 mL of dimethylformamide were heated to 140° C. with stirring for 3 hours. Then the solvent was distilled off and the crude product thus obtained was reacted without any further purification. Yield: 1.2 g (100% of theory); $R_f$ value: 0.54 (silica gel, ethyl acetate/cyclohexane=1:1).

c. Methyl 4-formyl-3-nitrobenzoate 1.2 g (4.8 mmol) of methyl 4-(2-dimethylaminovinyl)-3-nitrobenzoate were dissolved in 120 mL of tetrahydrofuran/water (1:1) and after the addition of 3.0 g (14.3 mmol) of sodium metaperiodate the mixture was stirred for 20 hours at ambient temperature. The suspension was then diluted with water and methylene chloride and extracted with methylene chloride. The combined organic extracts were washed with sodium hydrogen carbonate solution, dried, and evaporated down. The residue was chromatographed on silica gel and eluted with ethyl acetate/cyclohexane (1:3). Yield: 0.6 g (63% of theory); $R_f$ value: 0.63 (silica gel, ethyl acetate/cyclohexane=1:1).

d. Methyl 3-Amino-4-formylbenzoate

To a solution of 25 mL of ethanol/glacial acetic acid/water (2:2:1) were added 0.6 g (2.9 mmol) of methyl 4-formyl-3-nitrobenzoate, 1.2 g (21.4 mmol) of iron powder and 0.01 mL of concentrated hydrochloric acid and the mixture was refluxed with stirring for 15 minutes. Then the iron was separated off, the solution was diluted with water and extracted with methylene chloride. The combined organic extracts were washed with water, dried, and evaporated down. Yield: 0.3 g (58% of theory); $R_f$ value: 0.74 (silica gel, methylene chloride/methanol=9.5:0.5).

e. Methyl 3-[3-(4-cyanophenyl)propionylamino]-4-formylbenzoate 1.0 g (5.6 mmol) of methyl 3-amino-4-formylbenzoate and 1.1 g (5.6 mmol) of 4-cyanophenylpropionic acid chloride were dissolved in 50 mL of methylene chloride and after the addition of 0.7 g (5.6 mmol) of N-ethyldiisopropylamine the mixture was stirred for 24 hours at ambient temperature. Then it was extracted with sodium hydrogen carbonate solution; the combined organic extracts were dried and evaporated down. The residue was chromatographed on silica gel and eluted with ethyl acetate/cyclohexane (1:3). Yield: 0.6 g (32% of theory); $R_f$ value: 0.60 (silica gel, ethyl acetate/cyclohexane=1:1).

f. Methyl 2-[2-(4-cyanophenyl)ethyl]quinazoline-7-carboxylate 0.6 g (1.8 mmol) of ethyl 3-[3-(4-cyanophenyl)propionylamino]-4-formylbenzoate and 10 mL of methanolic ammonia solution were agitated in a pressure vessel for 36 hours. Then the solvent was distilled off, the residue was chromatographed on silica gel and eluted with methylene chloride containing 0 to 1% methanol. Yield: 0.35 g (62% of theory); $R_f$ value: 0.38 (silica gel, ethyl acetate/cyclohexane=1:1).

g. 2-[2-(4-Cyanophenyl)ethyl]quinazolin-7-carboxylic acid 0.3 g (0.94 mmol) of methyl 2-[2-(4-cyanophenyl)ethyl]quinazoline-7-carboxylate were dissolved in 4.7 mL of 1N lithium hydroxide solution and 4 mL of tetrahydrofuran and stirred for 3 hours at ambient temperature. Then 4.7 mL of 1N hydrochloric acid were added and the mixture was stirred for 30 minutes. The product precipitated was suction filtered, washed with water, and dried. Yield: 0.30 g (100% of theory); $R_f$ value: 0.1 (silica gel, ethyl acetate/cyclohexane=1:1).

h. 2-[2-(4-Cyanophenyl)ethyl]quinazolin-7-yl-carboxylic acid-N-phenyl-N-(2-methoxycarbonylethyl)amide 0.4 g (1.3 mmol) of 2-[2-(4-cyanophenyl)ethyl]quinazoline-7-carboxylic acid and 5 mL of thionyl chloride were stirred for 60 minutes at 50° C. Then the thionyl chloride was distilled off, the residue was dissolved in methylene chloride, mixed with 0.24 g (1.3 mmol) of methyl 3-(N-phenylamino)propionate and 0.22 mL of (1.3 mmol) of N-ethyldiisopropylamine and stirred for 18 hours at ambient temperature. After evaporation of the solvent in vacuo, the residue was chromatographed on silica gel and eluted with methylene chloride containing 1% methanol. Yield: 230 mg (37% of theory); $R_f$ value: 0.64 (silica gel, methylene chloride/methanol=9:1).

i. 2-[2-(4-Amidinophenyl)ethyl]quinazolin-7-yl-carboxylic acid-N-phenyl-N-(2-ethoxycarbonylethyl)amide hydrochloride 230 mg (0.5 mmol) of 2-[2-(4-cyanophenyl)ethyl]quinazolin-7-yl-carboxylic acid-N-phenyl-N-(2-methoxycarbonylethyl)amide were stirred in 30 mL of saturated ethanolic hydrochloric acid for 8 hours at ambient temperature. Then the mixture was evaporated to dryness in vacuo, the residue was taken up in 20 mL of ethanol, combined with 0.5 g (5.0 mmol) of ammonium carbonate and stirred overnight at ambient temperature. After evaporation of the solvent, the crude product was chromatographed on silica gel and eluted with methylene chloride/ethanol (4:1). Yield: 100 mg (39% of theory), $C_{29}H_{29}N_5O_3$ (495.59); $R_f$ value: 0.5 (silica gel, methylene chloride/ethanol=4:1); mass spectrum: $(M+H)^+=496$.

EXAMPLE 155

1-Methyl-2-[N-(4-amidinophenyl)aminomethyl] benzimidazol-5-yl-sulfonic acid-N-(1-methylpyrazol-4-yl)-N-(2-hydroxycarbonylethyl) amide Prepared analogously to Example 26 from 1-methyl-2-[N-(4-amidinophenyl)aminomethyl]benzimidazol-5-yl-sulfonic acid-N-(1-methylpyrazol-4-yl)-N-(2-ethoxycarbonylethyl)amide hydrochloride and sodium hydroxide solution. Yield: 95% of theory, $C_{23}H_{26}N_8O_4S$ (510.6); $R_f$ value: 0.53 (Reversed Phase silica gel RP-18, methanol+5% saline solution); EKA mass spectrum: $(M+H)^+=511$; $(M+Na)^+=533$; $(M+2Na)^{++}=278$.

EXAMPLE 156

1-Methyl-2-[N-(3-amidinopyridin-6-yl) aminomethyl]benzimidazol-5-yl-carboxylic acid-N-(2-pyridyl)-N-(2-ethoxycarbonylethyl)amide hydrochloride a) 3-[(N-tert-Butoxycarbonylamino)acetylamino]-4-methylaminobenzoic acid-N-(2-pyridyl)-N-(2-ethoxycarbonylethyl)amide 19.2 g (0.11 mol) of N-tert-butyloxycarbonylglycine were dissolved in 175 mL of dimethylformamide, mixed with 35.2 g (0.11 mol) of O-benzotriazol-1-yl)-N,N,N',N'-tetramethyluronium tetrafluoroborate, 11.0 g of triethylamine, and 34.2 g (0.10 mol) of 3-amino-4-methylaminobenzoic acid-N-(2-pyridyl)-N-(2-ethoxycarbonylethyl)amide and stirred for 2.5 hours at ambient temperature. Then the reaction solution was mixed with 5 l of ice water and stirred for 2 hours. The grey precipitate formed was filtered off, washed with water, dried, and recrystallized from ethyl acetate with the addition of activated charcoal. Yield: 39.85 g (80% of theory), $C_{25}H_{33}N_5O_6$ (499.6); $R_f$ value: 0.55 (silica gel; methylene chloride/ethanol=19:1).

b) 1-Methyl-2-(N-tert-butoxycarbonylaminomethyl) benzimidazol-5-yl-carboxylic acid-N-(2-pyridyl)-N-(2-ethoxycarbonylethyl)amide 10.0 g (0.02 mol) of 3-[(N-tert-butoxycarbonylamino) acetylamino]-4-methylaminobenzoic acid-N-(2-pyridyl)-N-(2-ethoxycarbonylethyl)amide were dissolved in 50 mL of glacial acetic acid and refluxed for one hour. Then the solvent was distilled off, the residue was mixed with ice water and adjusted to pH 8 by the addition of 2N ammonia. After extraction three times with ethyl acetate, the combined organic phases were washed with saline solution and dried over sodium sulfate. After evaporation of the solvent, the crude product was chromatographed on silica gel, eluting first with methylene chloride, then with methylene chloride/ethanol (50:1) and (25:1). The desired fractions were combined and evaporated down. Yield: 5.85 g (61% of theory), $C_{25}H_{31}N_5O_5$ (481.6); $R_f$ value: 0.70 (silica gel; methylene chloride/ethanol=9:1).

c) 1-Methyl-2-aminomethylbenzimidazol-5-yl-carboxylic acid-N-(2-pyridyl)-N-(2-ethoxycarbonylethyl)amide trifluoroacetate 4.81 g (0.10 mol) of 1-methyl-2-(N-tert-butoxycarbonylaminomethyl)benzimidazol-5-yl-carboxylic acid-N-(2-pyridyl)-N-(2-ethoxycarbonylethyl)amide were dissolved in 25 mL of methylene chloride, mixed with 5 mL of trifluoroacetic acid and stirred for 5 hours at ambient temperature. Then the solvent was evaporated off and the residue was stirred with ether. The crystals thus formed were filtered off, washed with ether, and dried. Yield: 3.15 g (68% of theory), $C_{20}H_{23}N_5O_3$ (381.4); $R_f$ value: 0.18 (silica gel; methylene chloride/ethanol=9:1).

d) 1-Methyl-2-[N-(3-cyanopyridin-6-yl)aminomethyl]benzimidazol-5-yl-carboxlic acid-N-(2-pyridyl)-N-(2-ethoxycarbonylethyl)amide 1.5 g (3.25 mmol) of 1-methyl-2-aminomethylbenzimidazol-5-yl-carboxylic acid-N-(2-pyridyl)-N-(2-ethoxycarbonylethyl)amide trifluoroacetate were stirred into 10 mL of N-ethyldiisopropylamine and heated to 100° C. for 15 minutes. After the addition of 720 mg (5.25 mmol) of 2-chloro-5-cyanopyridine, the reaction mixture was heated to 125° C. for 2 hours. After cooling to ambient temperature and stirring with about 20 mL of water, the pH was adjusted to 4 by the addition of 1N hydrochloric acid and the mixture was extracted 3 times with ethyl acetate. The combined organic phases were washed with saline solution and dried over sodium sulfate. After evaporation of the solvent, the crude product was chromatographed on silica gel, eluting first with methylene chloride, later with methylene chloride/ethanol (25:1) and (19:1). The desired fractions were combined and evaporated down. Yield: 1.05 g (67% of theory), $C_{26}H_{25}N_7O$ (483.6); mass spectrum: $(M+H)^+=484$.

e) 1-Methyl-2-[N-(3-amidinopyridin-6-yl)aminomethyl]benzimidazol-5-yl-carboxylic acid-N-(2-pyridyl-N-(2-ethoxycarbonylethyl)amide hydrochloride Prepared analogously to Example 25d from 1-Methyl-2-[N-(3-cyanopyridin-6-yl)aminomethyl]benzimidazol-5-yl-carboxylic acid-N-(2-pyridyl)-N-(2-ethoxycarbonylethyl)amide and ethanolic hydrochloric acid, ethanol, and ammonium carbonate. Yield: 38% of theory, $C_{28}H_{28}N_8O_3$ (500.6); mass spectrum: $(M+H)^+=501$.

EXAMPLE 157

1-Methyl-2-[N-(4-amidinophenyl)aminomethyl]indol-5-yl-carboxylic acid-N-phenyl-N-(2-methoxycarbonylethyl)amide hydroiodide a) 4-Nitrobenzoic acid-N-phenyl-N-(2-methoxycarbonylethyl)amide 16.7 g (0.1 mol) of 4-nitrobenzoic acid were refluxed in 50 mL of thionyl chloride and 3 drops of dimethylformamide for 1 hour. After the solvent had been distilled off in vacuo, the crude product was dissolved in 150 mL of tetrahydrofuran and added dropwise to a solution of 18 g (0.1 mol) of N-(2-methoxycarbonylethyl)aniline in 250 mL of tetrahydrofuran and 42 mL (0.3 mol) of triethylamine. After being stirred for one hour at ambient temperature, the reaction mixture was diluted with 250 mL of ethyl acetate and washed 2× with 200 mL of 14% saline solution. After the solvent had been distilled off and the residue chromatographed (silica gel; methylene chloride), a yellow oil was obtained which slowly solidified. Yield: 32.6 g (100% of theory); $R_f$ value: 0.37 (silica gel; methylene chloride/methanol=50:1).

b) 4-Aminobenzoic acid-N-phenyl-N-(2-methoxycarbonylethyl)amide 22 g (67 mmol) of 4-nitrobenzoic acid-N-phenyl-N-(2-methoxycarbonylethyl)amide were hydrogenated in 500 mL of methanol with 2 g of 10% palladium on charcoal at 3 bar hydrogen pressure for 3 hours. After filtration and distillation of the solvent, the reaction mixture was washed with 100 mL of ether and the white crystalline product was further reacted directly. Yield: 18.6 g (94% of theory), $R_f$ value: 0.70 (silica gel; methylene chloride/ethanol=19:1).

c) 2-Methyl-3-thiomethylindol-5-yl-carboxylic acid-N-phenyl-N-(2-methoxycarbonylethyl)amide 26.8 g (91 mmol) of 4-aminobenzoic acid-N-phenyl-N-(2-methoxycarbonylethyl)amide were dissolved in 500 mL of methylene chloride, cooled to −70° C. and mixed within 30 minutes with freshly prepared tert-butylhypochlorite (M. J. Mintz et al., Organic Synthesis, Coll. Vol. 5, page 184). The mixture was stirred for 2 hours at −70° C., then 9.46 g (91 mmol) of methylthioacetone in 40 mL of methylene chloride were added dropwise within 10 minutes and stirring was continued for a further 1.5 hours. Then 12.7 mL (9.1 g, 91 mmol) of triethylamine in 25 mL of methylene chloride were added. The mixture was left for 30 minutes at −78° C. and then slowly warmed to ambient temperature overnight. After washing twice with 50 mL of water, the organic phase was separated off and dried with sodium sulfate. After removal of the solvent in vacuo, a white amorphous substance is obtained after purification by chromatography (silica gel; ethyl acetate/petroleum ether=2:8 to 3:7). Yield: 24.1 g (69% of theory), $C_{21}H_{22}N_2O_3S$ (382.49); $R_f$ value: 0.58 (silica gel; ethyl acetate/petroleum ether=1:1); mass spectrum: $(M)^+=382$.

d) 1-tert-Butoxycarbonyl-2-methylindol-5-yl-carboxylic acid-N-phenyl-N-(2-methoxycarbonylethyl)amide 8.9 g (23 mmol) of 2-methyl-3-thiomethylindol-5-yl-carboxylic acid-N-phenyl-N-(2-methoxycarbonylethyl)amide were dissolved in 600 mL of ethanol, mixed with about 150 mg of Raney nickel and stirred for 2 hours at ambient temperature (analogously to P. G. Gassman et al., Organic Synthesis Coll. Vol. 6, page 601). Then the mixture was filtered and the solvent eliminated in vacuo. The crude product thus obtained (8 g) was dissolved in 200 mL of absolute tetrahydrofuran, mixed with 150 mg of dimethylaminopyridine and 6.84 g (32 mmol) of di-tert-butyl pyrocarbonate, and stirred for 2.5 hours at 50° C. Then the solvent was distilled off in vacuo and the crude product was purified by chromatography (silica gel, ethyl acetate/petroleum ether=1:4). Yield: 10.0 g (98% of theory); $R_f$ value: 0.40 (silica gel; ethyl acetate/petroleum ether=3:7).

e) 2-[N-(4-Cyanophenyl)aminomethyl]indol-5-yl-carboxylic acid-N-phenyl-N-(2-methoxycarbonylethyl)amide 3.5 g (8 mmol) of 1-tert-butoxycarbonyl-2-methylindol-5-yl-carboxylic acid-N-phenyl-N-(2-methoxycarbonylethyl)amide were dissolved in 80 mL of carbon tetrachloride, mixed with 1.5 g (8.4 mmol) of N-bromosuccinimide and 20 mg of azobisisobutyronitrile and refluxed for 2.5 hours. Then the still warm solution was filtered, the filtrate obtained was washed with saturated sodium hydrogen carbonate solution and dried with sodium sulfate. After distillation of the solvent, the crude product was dissolved in 30 mL of N-ethyldiisopropylamine, mixed with 1.0 g (8 mmol) of 4-aminobenzonitrile and refluxed for 2.5 hours. The solvent was distilled off in vacuo and the residue obtained was purified by chromatography (silica gel; ethyl acetate/petroleum ether=1:4 to 1:1). Yield: 1.1 g (30% of theory); $R_f$ value: 0.21 (silica gel; ethyl acetate/petroleum ether=1:1).

f. 1-Methyl-2-[N-(4-thiocarbamoylphenyl)aminomethyl] indol-5-yl-carboxylic acid-N-phenyl-N-(2-methoxycarbonylethyl)amide 1.5 g (3.3 mmol) of 2-[N-(4-cyanophenyl)aminomethyl] indol-5-yl-carboxylic acid-N-phenyl-N-(2-methoxycarbonylethyl)amide were dissolved in 60 mL of xylene, mixed with 0.45 g (3.3 mmol) of potassium carbonate and 0.5 mL of (3.3 mmol) of methyl p-toluenesulfonate and refluxed for 4 hours. Then the same amounts of potassium carbonate and methyl toluenesulfonate were added a second time and the mixture was refluxed overnight. It was filtered and washed with acetone. After concentration of the filtrate thus obtained, the residue obtained was purified by chromatography (silica gel; ethyl acetate/petroleum ether= 1:4 to 2:3). The N-methylated indole obtained (yield: 0.64 g, 41% of theory) was dissolved in 20 mL of pyridine and mixed with 0.67 mL (1.37 mmol) of triethylamine. Then hydrogen sulfide gas was introduced into the solution thus obtained. After 4.5 days, nitrogen was passed through the reaction solution for 30 minutes, the solvent was distilled off and the residue obtained was purified by chromatography (silica gel; methylene chloride/ethanol 99:1 to 98:2). Yield: 0.30 g (43% of theory), $C_{28}H_{28}N_4O_3S$ (500.62); EKA mass spectrum: $(M+H)^+=501$; $(M+Na)^+=523$.

g) 1-Methyl-2-[N-(4-amidinophenyl)aminomethyl]indol-5-yl-carboxylic acid-N-phenyl-N-(2-methoxycarbonylethyl) amide hydroiodide 0.30 g (0.60 mmol) of 1-methyl-2-[N-(4-thiocarbamoyl) phenyl)aminomethyl]indol-5-yl-carboxylic acid-N-phenyl-N-(2-methoxycarbonylethyl)amide were dissolved in 20 mL of acetone together with 0.75 mL (12 mmol) of methyl iodide and stirred for 2 hours at ambient temperature. Then the solvent was distilled off and the crude product was stirred together with 1.0 g of ammonium acetate in 12 mL of ethanol and 5 mL of methylene chloride for 20 hours at 40° C. The solvent was distilled off in vacuo and the residue obtained was purified by chromatography (silica gel; methylene chloride/ethanol=9:1 to 4:1). Yield: 55% of theory, $C_{28}H_{29}N_5O_3$ (483.58); $R_f$ value: 0.20 (silica gel; methylene chloride/ethanol=4:1+1 drop of acetic acid); EKA mass spectrum: $(M+H)^+=484$.

EXAMPLE 158

1-Methyl-2-[N-(4-amidinophenyl)aminomethyl] thieno[2,3-d]imidazol-5-yl-carboxylic acid-N-phenyl-N-(2-ethoxycarbonylethyl)amide hydrochloride a) Iminoethyl Methoxyacetate Hydrochloride A solution of 35.5 g (0.50 mol) of methoxyacetonitrile in 29 mL (23 g, 0.50 mol) of ethanol and 30 mL of absolute diethylether was cooled to 0° C. and over 1 hour 22.5 g (0.62 mol) of hydrogen chloride gas was introduced, whilst towards the end of the introduction of gas the reaction product crystallized out. To complete the precipitation 130 mL of diethylether were added and the colorless needles were filtered off. Yield: 66.4 g (86% of theory); melting point: 117° C.–118° C.

b) 4-Hydroxymethyl-2-methoxymethylimidazole

A mixture of 30.6 g (0.20 mol) of iminoethyl methoxyacetate hydrochloride, 18 g (0.20 mol) of 1,3-dihydroxyacetone and 200 mL of liquid ammonia was heated to 68° C. for 3 hours in a stirred autoclave at a pressure of 27 bar (analogously to: P. Dziuron et al., Arch. Pharm. 307, 1974, p.470). Then the ammonia was eliminated and 200 mL of methylene chloride were added. The white precipitate formed was filtered off and washed with methylene chloride. The filtrate was evaporated down and the residue obtained was purified by chromatography (aluminium oxide; methylene chloride/ethanol=90:10 to 85:15). Yield: 26.7 g (94% of theory), $C_6H_{10}N_2O_2$ (142.20); $R_f$ value: 0.43 (silica gel; methylene chloride/ethanol=9:1); mass spectrum: $(M)^+=142$.

c) 4-Hydroxymethyl-2-methoxymethyl-1-methylimidazole as a 1:1 mixture with 5-hydroxymethyl-2-methoxymethyl-1-methylimidazole A mixture of 7.1 g (50 mmol) of 4-hydroxymethyl-2-methoxymethylimidazole, 3.0 g (53 mmol) of powdered potassium hydroxide and 3.4 mL (0.55 mmol) of methyl iodide was heated to 50° C. in 100 mL of dimethylformamide for 4 hours (analogously to I. Sinclair et al, J. Med. Chem., 29 1986, 261). Then the solvent was distilled off in vacuo and the crude product purified by column chromatography (aluminium oxide; methylene chloride/ethanol= 99:1 to 95:5). Yield: 6.1 g (78% of theory; 1:1 mixture of the two regioisomers); $R_f$ value: 0.32 (silica gel; methylene chloride/ethanol=19:1).

d) 5-Chloro-4-hydroxymethyl-2-methoxymethyl-1-methylimidazole

A 1:1 mixture of 7.7 g (49 mmol) of 4-hydroxymethyl-2-methoxymethyl-1-methylimidazole and 5-hydroxymethyl-2-methoxymethyl-1-methylimidazole and 7.3 g (55 mmol) of N-chlorosuccinimide was heated to 50° C. in 48 mL of ethylene glycol monoethylether and 70 mL of dioxane for 10 hours. Then the solvent was distilled off in vacuo and the crude product purified by chromatography (silica gel; methylene chloride/ethanol=99:1 to 90:10) to obtain the isomerically pure title compound. Yield: 3.4 g (36% of theory); $R_f$ value: 0.40 (silica gel; methylene chloride/ethanol=19:1).

e) 5-chloro-4-formyl-2-methoxymethyl-1-methylimidazole 3.4 g (18 mmol) of 5-chloro-4-hydroxymethyl-2-methoxymethyl-1-methylimidazole were dissolved in 100 mL of methylene chloride and at 2 hour intervals manganese dioxide was added (2×6.0 g, a total of 0.14 mol). After 4 hours, the inorganic component was filtered off, the solvent was eliminated and the crude product obtained was further reacted without any further purification. Yield: 3.0 g (89% of theory); $R_f$ value: 0.44 (silica gel; methylene chloride/ethanol=50:1).

f) Ethyl 1-methyl-2-methoxymethylthieno[2,3-d]imidazol-5-yl-carboxylate

To a freshly prepared sodium ethoxide solution (from 391 mg, 17 mmol of sodium) in 15 mL of ethanol were added dropwise 1.9 mL (2.1 g, 17 mmol) of ethyl thioglycolate. After 1 hour stirring at ambient temperature, 1.6 g (8.5 mmol) of 5-chloro-4-formyl-2-methoxymethyl-1-methylimidazole in 20 mL of absolute ethanol were added and the mixture was heated to 80° C. (analogously to B. Iddon et al., J. Chem. Soc. Perkin Trans. I, 1987, 1457). After 5 hours, the solvent was distilled off, the residue was taken up in 50 mL of methylene chloride and washed with 20 mL of water. The aqueous phase was washed again with 20 mL of methylene chloride and then the combined organic phases were dried with sodium sulfate. After removal of the solvent in vacuo, the crude product obtained was purified by column chromatography (aluminium oxide; methylene chloride). Yield: 1.0 g (46% of theory), $C_{11}H_{14}N_2O_3S$ (254.31); $R_f$ value: 0.48 (silica gel; methylene chloride/ethanol=50:1); EKA mass spectrum: $(M+H)^+=255$; $(M+Na)^+=277$.

g) 1-Methyl-2-methoxymethylthieno[2,3-d]imidazol-5-yl-carboxylic acid

To a solution of 0.90 g (3.54 mmol) of ethyl 1-methyl-2-methoxymethylthieno[2,3-d]imidazol-5-yl-carboxylate in 30 mL of ethanol were added dropwise 5 mL of 2 N sodium hydroxide solution and the mixture was stirred for 2 hours at ambient temperature. Then the solvent was distilled off in vacuo, the residue was taken up in 5 mL of water and washed with 10 mL of diethylether. The aqueous phase was acidified with 6 mL of 2N hydrochloric acid, cooled to 0° C. and the precipitated crystals are filtered off. Yield: 0.50 g (63% of theory), $C_9H_{10}N_2O_3S$ (226.26); $R_f$ value: 0.21 (silica gel; methylene chloride/ethanol=9:1+a few drops of acetic acid); mass spectrum: $(M)^+=226$.

h) 1-Methyl-2-methoxymethylthieno[2,3-d]imidazol-5-yl-carboxylic acid-N-phenyl-N-(2-methoxycarbonylethyl) amide A suspension of 0.50 g (2.2 mmol) of 1-methyl-2-methoxymethylthieno[2,3-d]imidazol-5-yl-carboxylic acid in 20 mL of methylene chloride was mixed with 2.0 mL (3.2 g, 27 mmol) of thionyl chloride and refluxed for 60 minutes, during which time the solid gradually dissolved. After distillation of the liquid components, the crude product was taken up twice more in methylene chloride. After the solvent had been eliminated once more, the crude acid chloride was taken up in 20 mL of tetrahydrofuran and added dropwise to a mixture of 0.42 g (2.3 mmol) of N-(2-methoxycarbonylethyl)aniline and 0.92 mL (6.6 mmol) of triethylamine in 30 mL of tetrahydrofuran. After 16 hours stirring at 50° C., the solvent was eliminated and the crude product obtained was purified by chromatography (silica gel; methylene chloride/ethanol=100:1). Yield: 0.66 g (77% of theory); $R_f$ value: 0.47 (silica gel; methylene chloride/ethanol=19:1).

i) 1-Methyl-2-(N-4-cyanophenylaminomethyl)thieno[2,3-d]imidazol-5-yl-carboxylic acid-N-phenyl-N-(2-methoxycarbonylethyl)amide To a solution of 0.73 g (1.88 mmol) of 1-methyl-2-methoxymethylthieno[2,3-d]imidazol-5-yl-carboxylic acid-N-phenyl-N-(2-methoxycarbonylethyl)amide in 30 mL of methylene chloride were added dropwise at 5° C. 2.9 mL (2.9 mmol) of a 1-molar solution of boron tribromide in methylene chloride. After 16 hours stirring at ambient temperature, the mixture was washed with 20 mL of saturated sodium hydrogen carbonate solution, the organic phase was separated off, dried with sodium sulfate and filtered. The filtrate was mixed with 14 mL of N-ethyldiisopropylamine and 0.43 g (3.64 mmol) of 4-aminobenzonitrile. Then the methylene chloride was distilled off in vacuo, the residue obtained was heated to 50° C. for 1 hour and then the residual solvent was distilled off in vacuo. After chromatography (silica gel; methylene chloride/ethanol=99:1 to 97:3), a yellow oil was obtained which slowly solidified. Yield: 0.37 g (42% of theory); $R_f$ value: 0.29 (silica gel; methylene chloride/ethanol=50:1+a few drops of ammonia).

j) 1-Methyl-2-[N-(4-amidinophenyl)aminomethyl]thieno[2,3-d]imidazol-5-yl-carboxylic acid-N-phenyl-N-(2-ethoxycarbonylethyl)amide hydrochloride 0.38 g (0.80 mmol) of 1-methyl-2-(N-4-cyanophenylaminomethyl)thieno[2,3-d]imidazol-5-yl-carboxylic acid-N-phenyl-N-(2-methoxycarbonylethyl) amide were stirred in 40 mL of ethanol saturated with hydrogen chloride for 5 hours first at 0° C., then later at ambient temperature until no more starting material could be detected by thin layer chromatography. Then the solvent was distilled off at a maximum 28° C. bath temperature, the oily residue was taken up in 40 mL of absolute ethanol and mixed with 1.1 g of ammonium carbonate. After 18 hours, the solvent was distilled off in vacuo and the crude product was purified by chromatography (silica gel; methylene chloride/ethanol=9:1 to 4:1). Yield: 57% of theory, $C_{26}H_{28}N_6O_3S$ (504.62); $R_f$ value: 0.21 (silica gel; methylene chloride/ethanol=4:1+a few drops of acetic acid); EKA mass spectrum: $(M+H)^+=505$; $(M+H+Na)^{++}=264$.

EXAMPLE 159

1-Methyl-2-[N-(4-amidinophenyl)aminomethyl] thieno[2,3-d]imidazol-5-yl-carboxylic acid-N-phenyl-N-(2-hydroxycarbonylethyl)amide hydrochloride Prepared analogously to Example 2 from 1-methyl-2-[N-(4-amidinophenyl)aminomethyl]thieno[2,3-d]imidazol-5-yl-carboxylic acid-N-phenyl-N-(2-ethoxycarbonylethyl) amide hydrochloride and sodium hydroxide solution. Yield: 85% of theory, $C_{24}H_{24}N_6O_3S$ (476.56); $R_f$ value: 0.36 (Reversed Phase silica gel RP-8; methanol+5% saline solution); EKA mass spectrum: $(M+H)^+=477$; $(M+Na)^+=499$; $(M+2Na)^{++}=250$.

EXAMPLE 160

1-Methyl-3-[N-(4-amidinophenyl)thiomethyl] quinoxalin-2-on-6-yl-carboxylic acid-N-phenyl-N-(2-ethoxycarbonylethyl)amide hydrochloride a) 1-Methyl-3-[N-(4-cyanophenyl)thiomethyl]quinoxalin-2-on-6-yl-carboxylic acid-N-phenyl-N-(2-methoxycarbonylethyl)amide A solution of 2.5 g (7.6 mmol) of 3-amino-4-methylaminobenzoic acid-N-phenyl-N-(2-methoxycarbonylethyl)amide and 2.4 g (9.6 mmol) of ethyl 3-(4-cyanophenyl)thio-2-oxo-propionate were heated to boiling in 50 mL of ethanol for 30 minutes. After removal of the solvent, the crude product obtained was purified by chromatography (silica gel; methylene chloride). Yield: 1.6 g (40% of theory); $R_f$ value: 0.63 (silica gel; EtOAc/EtOH/ammonia=90:10:1).

b) 1-Methyl-3-[N-(4-amidinophenyl)thiomethyl] quinoxalin-2-on-6-yl-carboxylic acid-N-phenyl-N-(2-ethoxycarbonylethyl)amide hydrochloride Prepared analogously to Example 1 from 1-methyl-3-[N-(4-cyanophenyl)thiomethyl]quinoxalin-2-on-6-yl-carboxylic acid-N-phenyl-N-(2-ethoxycarbonylethyl)amide and ethanolic hydrochloric acid, ethanol, and ammonium carbonate. Yield: 23% of theory, $C_{28}H_{27}N_5O_4S$ (543.64); $R_f$ value: 0.25 (silica gel; ethyl acetate/ethanol/ammonia= 50:45:5); EKA mass spectrum: $(M+H)^+=544$; $(M+Na)^+=566$.

EXAMPLE 161

3-Methyl-2-[2-(4-amidinophenyl)ethyl]imidazo[1,2-a]pyridin-7-yl-carboxylic acid-N-phenyl-N-(2-ethoxycarbonylethyl)amide hydrochloride a) 3-Methyl-2-[2-(4-cyanophenyl)ethyl]imidazo[1,2-a] pyridin-7-yl-carboxylic acid-N-phenyl-N-(2-ethoxycarbonylethyl)amide 1.4 g (4.6 mmol) of 3-methyl-2-[2-(4-cyanophenyl)ethyl] imidazo[1,2-a]pyridin-7-yl-carboxylic acid (prepared from 4-bromo-1-(4-cyanophenyl)-1-penten-3-one and methyl 2-aminopyridine-4-carboxylate analogously to Y. Katsura et al., Chem. Pharm. Bull. 1992, 40, 1424–1438) were suspended in 15 mL of thionyl chloride and heated to boiling for 1 hour until fully dissolved. After the thionyl chloride had been distilled off, the acid chloride was dissolved in 15 mL of pyridine without any further purification and at 0° C. mixed with 1.0 g (5.2 mmol) of N-(2-ethoxycarbonylethyl) aniline. After 1 hour, the solvent was distilled off, the residue was taken up in 30 mL of methylene chloride, washed with 15 mL of 1N hydrochloric acid, and dried with sodium sulfate. After distillation of the solvent and chromatography (silica gel; methylene chloride/ethanol=0 to 2%), a brown oil was obtained. Yield: 1.48 g (64% of theory); $R_f$ value: 0.73 (silica gel; ethyl acetate/ethanol/ammonia=90:10:1).

b) 3-Methyl-2-[2-(4-amidinophenyl)ethyl]imidazo[1,2-a]pyridin-7-yl-carboxylic acid-N-phenyl-N-(2-ethoxycarbonylethyl)amide hydrochloride Prepared analogously to Example 1 from 3-methyl-2-[2-(4-cyanophenyl)ethyl]imidazo[1,2-a]pyridin-7-yl-carboxylic acid-N-phenyl-N-(2-ethoxycarbonylethyl)amide and ethanolic hydrochloric acid, ethanol, and ammonium carbonate. Yield: 62% of theory, $C_{29}H_{31}N_5O_3$ (497.60); $R_f$ value: 0.23 (silica gel; ethyl acetate/ethanol/ammonia= 50:45:5); EKA mass spectrum: $(M+H)^+=498$.

EXAMPLE 162

3-Methyl-2-[2-(4-amidinophenyl)ethyl]imidazo[1,2-a]pyridin-7-yl-carboxylic acid-N-phenyl-N-(2-hydroxycarbonylethyl)amide hydrochloride Prepared analogously to Example 2 from 3-methyl-2-[2-(4-amidinophenyl)ethyl]imidazo[1,2-a]pyridin-7-yl-carboxylic acid-N-phenyl-N-(2-ethoxycarbonylethyl)amide hydrochloride and sodium hydroxide solution. Yield: 92% of theory, $C_{27}H_{27}N_5O_3$ (469.55); $R_f$ value: 0.19 (silica gel; ethyl acetate/ethanol/ammonia=50:45:5); EKA mass spectrum: $(M+H)^+=470$; $(M+Na)^+=492$; $(M+2H)^{++}=235.7$; $(M+H+Na)^{++}=246.7$; $(M+2Na)^{++}=257.7$.

EXAMPLE 163

1-Methyl-2-[N-(4-amidinophenyl)aminomethyl]benzimidazol-5-yl-carboxylic acid-N-phenyl-N-[(N-ethoxycarbonylethyl-N-methyl)-2-aminoethyl]amide dihydrochloride Prepared analogously to Example 25d from 1-methyl-2-[N-(4-cyanophenyl)aminomethyl]benzimidazol-5-yl-carboxylic acid-N-phenyl-N-[(N-ethoxycarbonylethyl-N-methyl)-2-aminoethyl]amide and ethanolic hydrochloric acid, ethanol, and ammonium carbonate. Yield: 80% of theory, $C_{31}H_{37}N_7O_3$ (555.7); $R_f$ value: 0.24 (silica gel; dichloromethane/methanol=4:1); EKA mass spectrum: $(M+H)^+=556$; $(M+H+Na)^{++}=289.8$; $(M+2H)^{++}=278.8$.

EXAMPLE 164

1-Methyl-2-[N-(4-amidinophenyl)aminomethyl]benzimidazol-5-yl-carboxylic acid-N-phenyl-N-[(N-hydroxycarbonylethyl-N-methyl)-2-aminoethyl]amide hydrochloride Prepared analogously to Example 26 from 1-methyl-2-[N-(4-amidinophenyl)aminomethyl]benzimidazol-5-yl-carboxylic acid-N-phenyl-N-[(N-ethoxycarbonylethyl-N-methyl)-2-aminoethyl]amide dihydrochloride and sodium hydroxide solution. Yield: 79% of theory, $C_{29}H_{33}N_7O_3$ (527.6); $R_f$ value: 0.43 (Reversed Phase silica gel RP-18; methanol/5% aqueous saline solution=6:4); EKA mass spectrum: $(M+H)^+=528$; $(M+H+Na)^{++}=275.6$; $(M+2H)^{++}=264.6$.

EXAMPLE 165

1-Methyl-2-[N-(4-amidinophenyl)aminomethyl]benzimidazol-5-yl-carboxylic acid-N-phenyl-N-(3-hydroxy-n-propyl)amide hydrochloride Prepared from 1-methyl-2-[N-(4-amidinophenyl)aminomethyl]benzimidazol-5-yl-carboxylic acid-N-phenyl-N-(3-benzyloxy-n-propyl)amide hydrochloride by hydrogenation over palladium/charcoal (10%) at 5 bar hydrogen pressure and at ambient temperature. Yield: 61% of theory, $C_{26}H_{28}N_6O_2$ (456.6); $R_f$ value: 0.70 (Reversed Phase silica gel RP-18; methanol/5% aqueous saline solution=9:1); EKA mass spectrum: $(M+H)^+=457$; $(M+H+Na)^{++}=240$.

EXAMPLE 166

1-Methyl-2-[N-[4-(N-n-hexyloxycarbonylamidino)phenyl]aminomethyl]benzimidazol-5-yl-carboxylic acid-N-(2-pyridyl)-N-(2-hydroxycarbonylethyl)amide Prepared analogously to Example 26 from 1-methyl-2-[N-[4-(N-n-hexyl-oxycarbonylamidino)phenyl]aminomethyl]benzimidazol-5-yl-carboxylic acid-N-(2-pyridyl)-N-(2-ethoxycarbonylethyl)amide and sodium hydroxide solution. Yield: 97% of theory, $C_{32}H_{37}N_7O_5$ (599.7); $R_f$ value: 0.22 (silica gel; dichloromethane/methanol=9:1); EKA mass spectrum: $(M+H)^+=600$; $(M+H+Na)^{++}=311.7$; $(M+2H)^{++}=300.8$; $(M+2Na)^{++}=322.8$.

EXAMPLE 167

1-Methyl-2-[N-[4-(N-n-hexyloxycarbonylamidino)phenyl]aminomethyl]benzimidazol-5-yl-carboxylic acid-N-phenyl-N-(3-hydroxy-n-propyl)amide Prepared analogously to Example 165 from 1-methyl-2-[N-[4-(N-n-hexyloxycarbonylamidino)phenyl]aminomethyl]benzimidazol-5-yl-carboxylic acid-N-phenyl-N-(3-benzyloxy-n-propyl)amide by catalytic debenzylation. Yield: 26% of theory, $C_{33}H_{40}N_6O_4$ (584.7); $R_f$ value: 0.39 (silica gel; dichloromethane/ethanol=9:1); EKA mass spectrum: $(M+H)^+=585$; $(M+H+Na)^{++}=304$; $(M+Na)^+=607$.

EXAMPLE 168

1-Methyl-2-[N-(4-amidinophenyl)aminomethyl]benzimidazol-5-yl-carboxylic acid-N-(3-fluorophenyl)-N-(2-ethoxycarbonylethyl)amide hydrochloride Prepared analogously to Example 25d from 1-methyl-2-[N-(4-cyanophenyl)aminomethyl]benzimidazol-5-yl-carboxylic acid-N-(3-fluorophenyl)-N-(2-ethoxycarbonylethyl)amide and ethanolic hydrochloric acid, ethanol, and ammonium carbonate. Yield: 42% of theory, $C_{28}H_{29}FN_6O_3$ (516.6); $R_f$ value: 0.31 (silica gel; dichloromethane/methanol 5:1); EKA mass spectrum: $(M+H)^+=517$; $(M+H+Na)^{++}=270$.

EXAMPLE 169

1-Methyl-2-[N-(4-amidinophenyl)aminomethyl]benzimidazol-5-yl-carboxylic acid-N-(4-fluorophenyl)-N-(2-ethoxycarbonylethyl)amide hydrochloride Prepared analogously to Example 25d from 1-methyl-2-[N-(4-cyanophenyl)aminomethyl]benzimidazol-5-yl-carboxylic acid-N-(4-fluorophenyl)-N-(2-ethoxycarbonylethyl)amide and ethanolic hydrochloric acid, ethanol, and ammonium carbonate. Yield: 90% of theory, $C_{28}H_{29}FN_6O_3$ (516.6); $R_f$ value: 0.29 (silica gel; dichloromethane/methanol=5:1); EKA mass spectrum: $(M+H)^+=517$; $(M+H+Na)^{++}=270$.

EXAMPLE 170

1-Methyl-2-[N-(4-amidinophenyl)aminomethyl]benzimidazol-5-yl-carboxylic acid-N-(3-fluorophenyl)-N-(2-hydroxycarbonylethyl)amide Prepared analogously to Example 26 from 1-methyl-2-[N-(4-amidinophenyl)aminomethyl]benzimidazol-5-ylcarboxylic acid-N-(3-fluorophenyl)-N-(2-ethoxycarbonylethyl)amide hydrochloride and sodium hydroxide solution. Yield: 97% of theory, $C_{26}H_{25}FN_6O_3$ (488.5); $R_f$ value: 0.13 (silica gel; dichloromethane/ethanol= 4:1); EKA mass spectrum: $(M+H)^+=489$; $(M+Na)^+=511$; $(M+2Na)^{++}=267$.

EXAMPLE 171

1-Methyl-2-[N-4-amidinophenyl)aminomethyl] benzimidazol-5-yl-carboxylic acid-N-(4-fluorophenyl)-N-(2-hydroxycarbonylethyl)amide Prepared analogously to Example 26 from 1-methyl-2-[N-(4-amidinophenyl)aminomethyl]benzimidazol-5-yl-carboxylic acid-N-(4-fluorophenyl)-N-(2-ethoxycarbonylethyl)amide hydrochloride and sodium hydroxide solution. Yield: 89% of theory, $C_{26}H_{25}FN_6O_3$ (488.5); $R_f$ value: 0.15 (silica gel; dichloromethane/ethanol= 4:1); EKA mass spectrum: $(M+H)^+=489$; $(M+Na)^+=511$; $(M+2Na)^{++}=267$.

EXAMPLE 172

1-Methyl-2-[-(4-amidino-2-methoxyphenyl) aminomethyl]benzimidazol-5-yl-carboxylic acid-N-phenyl-N-(2-ethoxycarbonylethyl)amide hydrochloride Prepared analogously to Example 25d from 1-methyl-2-[N-(4-cyano-2-methoxyphenyl)aminomethyl]benzimidazol-5-yl-carboxylic acid-N-phenyl-N-(2-ethoxycarbonylethyl) amide and ethanolic hydrochloric acid, ethanol, and ammonium carbonate. Yield: 89% of theory, $C_{29}H_{32}N_6O_4$ (528.6); $R_f$ value: 0.13 (silica gel; dichloromethane/ethanol= 4:1); EKA mass spectrum: $(M+H)^+=529$; $(M+H+Na)^{++}=276$; $(M+2H)^{++}=265$.

EXAMPLE 173

1-Methyl-2-[N-[4-(N-4-ethylbenzoylamidino) phenyl]aminomethyl]benzimidazol-5-yl-carboxylic acid-N-(2-pyridyl)-N-(2-ethoxycarbonylethyl)amide Prepared analogously to Example 90 from 1-methyl-2-[N-(4-amidinophenyl)aminomethyl]benzimidazol-5-yl-carboxylic acid-N-(2-pyridyl)-N-(2-ethoxycarbonylethyl) amide hydrochloride and 4-ethylbenzoylchloride. Yield: 64% of theory, $C_{36}H_{37}N_7O_4$ (631.7); $R_f$ value: 0.78 (silica gel; dichloromethane/methanol=9:1); EKA mass spectrum: $(M+H)^+=632$; $(M+H+Na)^{++}=327.8$; $(M+Na)^+=654$.

EXAMPLE 174

1-Methyl-2-[N-[4-(N-benzyloxycarbonyl)amidino) phenyl]aminomethyl]benzimidazol-5-yl-carboxylic acid-N-(2-pyridyl)-N-(2-ethoxycarbonylethyl)amide Prepared analogously to Example 90 from 1-methyl-2-[N-(4-amidinophenyl)aminomethyl]benzimidazol-5-yl-carboxylic acid-N-(2-pyridyl)-N-(2-ethoxycarbonylethyl) amide hydrochloride and benzyl chloroformate. Yield: 64% of theory, $C_{35}H_{35}N_7O_5$ (633.6); $R_f$ value: 0.60 (silica gel; dichloromethane/methanol=9:1); EKA mass spectrum: $(M+H)^+=634$; $(M+H+Na)^{++}=328.8$; $(M+Na)^+=656$.

EXAMPLE 175

1-Methyl-2-[N-(4-amidino-2-methoxyphenyl) aminomethyl]benzimidazol-5-yl-carboxylic acid-N-phenyl-N-(2-hydroxycarbonylethyl)amide Prepared analogously to Example 26 from 1-methyl-2-[N-(4-amidino-2-methoxyphenyl)aminomethyl] benzimidazol-5-yl-carboxylic acid-N-phenyl-N-(2-ethoxycarbonylethyl)amide hydrochloride and sodium hydroxide solution. Yield: 71% of theory, $C_{27}H_{28}N_6O_4$ (500.6); $R_f$ value: 0.15 (silica gel; dichloromethane/ethanol= 4:1); EKA mass spectrum: $(M+H)^+=501$; $(M+Na)^+=523$; $(M+2Na)^{++}=273$.

EXAMPLE 176

1-Methyl-2-[N-(4-amidino-2-methoxyphenyl) aminomethyl]benzimidazol-5-yl-carboxylic acid-N-(2-pyridyl)-N-(2-ethoxycarbonylethyl)amide hydrochloride Prepared analogously to Example 25d from 1-methyl-2-[N-(4-cyano-2-methoxyphenyl)aminomethyl]benzimidazol-5-yl-carboxylic acid-N-(2-pyridyl)-N-(2-methoxycarbonylethyl)amide and ethanolic hydrochloric acid, ethanol, and ammonium carbonate. Yield: 67% of theory, $C_{28}H_{31}N_7O_4$ (529.6); $R_f$ value: 0.16 (silica gel; dichloromethane/ethanol=4:1); EKA mass spectrum: $(M+H)^+=530$.

EXAMPLE 177

1-Methyl-2-[N-(4-amidino-2-methoxyphenyl) aminomethyl]benzimidazol-5-yl-carboxylic acid-N-(2-pyridyl)-N-(2-hydroxycarbonylethyl)amide Prepared analogously to Example 26 from 1-methyl-2-[N-(4-amidino-2-methoxyphenyl)aminomethyl] benzimidazol-5-yl-carboxylic acid-N-(2-pyridyl)-N-(2-ethoxycarbonylethyl)amide hydrochloride and sodium hydroxide solution. Yield: 78% of theory, $C_{26}H_{27}N_7O_4$ (501.6); $R_f$ value: 0.12 (silica gel; dichloromethane/ethanol= 4:1); EKA mass spectrum: $(M+H)^+=502$.

EXAMPLE 178

1-Methyl-2-[N-[4-(N-benzyloxycarbonyl)amidino) phenyl]aminomethyl]benzimidazol-5-yl-carboxylic acid-N-(2-pyridyl)-N-(2-hydroxycarbonylethyl) amide Prepared analogously to Example 104 from 1-methyl-2-[N-[4-(N-benzyloxycarbonylamidino)phenyl]aminomethyl] benzimidazol-5-yl-carboxylic acid-N-(2-pyridyl)-N-(2-ethoxycarbonylethyl)amide and sodium hydroxide solution. Yield: 62% of theory, $C_{33}H_{31}N_7O_5$ (605.7); $R_f$ value: 0.26 (silica gel; dichloromethane/methanol=9:1); EKA mass spectrum: $(M+H)^+=606$; $(M+Na)^+=628$; $(M—H+2Na)^+=650$; $(M+2H)^{++}=303.8$; $(M+H+Na)^{++}=314.8$; $(M+2Na)^{++}=325.7$.

EXAMPLE 179

1-Methyl-2-[N-(4-amidinophenyl)aminomethyl] benzimidazol-5-yl-carboxylic acid-N-phenyl-N-(3-benzyloxy-n-propyl)amide hydrochloride Prepared analogously to Example 25 from 1-methyl-2-[N-(4-cyanophenyl)aminomethyl]benzimidazol-5-yl-carboxylic acid-N-phenyl-N-(3-benzyloxy-n-propyl)amide and ethanolic hydrochloric acid, ethanol, and ammonium carbonate. Yield: 61% of theory, $C_{33}H_{34}N_6O_2$ (546.7); $R_f$ value: 0.19 (silica gel; dichloromethane/ethanol=4:1); EKA mass spectrum: $(M+H)^+=547$; $(M+H+Na)^{++}=285$.

EXAMPLE 180

1-Methyl-2-[N-[4-(N-n-hexyloxycarbonylamidino) phenyl]aminomethyl]benzimidazol-5-yl-carboxylic acid-N-phenyl-N-(3-benzyloxy-n-propyl)amide Prepared analogously to Example 90 from 1-methyl-2-[N-(4-amidinophenyl)aminomethyl]benzimidazol-5-ylcarboxylic acid-N-phenyl-N-(3-benzyloxy-n-propyl)amide hydrochloride and n-hexyl chloroformate. Yield: 73% of theory, $C_{40}H_{46}N_6O_4$ (674.9); $R_f$ value: 0.46 (silica gel; dichloromethane/ethanol=9:1); EKA mass spectrum: $(M+H)^+=675$; $(M+H+Na)^{++}=349$; $(M+Na)^+=697$; $(M+K)^+=713$.

EXAMPLE 181

3-Methyl-2-[2-(4-amidinophenyl)ethyl]imidazo[1,2-a]pyridin-7-yl-carboxylic acid-N-(2-pyridyl)-N-(2-ethoxycarbonylethyl)amide hydrochloride Prepared analogously to Example 1 from 3-methyl-2-[2-(4-cyanophenyl)ethyl]imidazo[1,2-a]pyridin-7-yl-carboxylic acid-N-(2-pyridyl)-N-(2-methoxycarbonylethyl) amide hydrochloride and ethanolic hydrochloric acid, ethanol, and ammonium carbonate. Yield: 53% of theory, $C_{28}H_{30}N_6O_3$ (498.59); $R_f$ value: 0.42 (silica gel; ethyl acetate/ethanol/ammonia=50:45:5); EKA mass spectrum: $(M+H)^+=499$; $(M+2Na)^{++}=272$; $(M+H+Na)^{++}=261$; $(M+2H)^{++}=250$.

EXAMPLE 182

1-Methyl-2-[N-(3-amidinopyridin-6-yl)-aminomethyl]benzimidazol-5-yl-carboxylic acid-N-(2-pyridyl)-N-(2-hydroxycarbonylethyl)amide Prepared analogously to Example 26 from 1-methyl-2-[N-(3-cyanopyridin-6-yl)-aminomethyl]benzimidazol-5-yl-carboxylic acid-N-(2-pyridyl)-N-(2-hydroxycarbonylethyl) amide and sodium hydroxide solution. Yield: 40% of theory, $C_{24}H_{24}N_8O_3$ (472.9); $R_f$ value: 0.67 (Reversed Phase silica gel RP-8; methanol/5% saline solution=1:1); EKA mass spectrum: $(M+H)^+=473$.

EXAMPLE 183

1-Methyl-2-[N-[4-(N-hydroxyamidino)phenyl]aminomethyl]benzimidazol-5-yl-carboxylic acid-N-(2-pyridyl)-N-[2-(methanesulfonylaminocarbonyl)ethyl]amide a. 1-Methyl-2-[N-(4-cyanophenyl)aminomethyl]benzimidazol-5-yl-carboxylic acid-N-(2-pyridyl)-N-[2-(methanesulfonylaminocarbonyl)ethyl]amide 2.0 g (4.5 mmol) of 1-methyl-2-[N-(4-cyanophenyl) aminomethyl]benzimidazol-5-yl-carboxylic acid-N-(2-pyridyl)-N-(2-hydroxycarbonylethyl)amide and 0.73 g (4.7 mmol) of carbonyldiimidazole were dissolved in 80 mL of tetrahydrofuran and 5 mL of dimethylformamide and stirred for 30 minutes at ambient temperature and for 2 hours at 90° C. In parallel, 0.55 g (5.8 mmol) of methanesulfonic acid amide and 0.28 g (5.8 mmol) of sodium hydride were suspended in 15 mL of dimethylformamide and stirred for 2 hours at ambient temperature. Then this suspension was added at ambient temperature to the tetrahydrofuran solution. After 12 hours at ambient temperature, 50 mL of water were added and the pH value was adjusted to 6.8. The solution was extracted 4× with methylene chloride, the combined organic phases were dried over sodium sulfate and evaporated down. The crude product was chromatographed on silica gel (methylene chloride/ethanol (40:1)). The desired fractions were combined and evaporated down. Yield: 1.05 g (44% of theory), $C_{26}H_{25}N_7O_4S$ (531.6); $R_f$ value: 0.72 (silica gel; dichloromethane/methanol=9:1).

b. 1-Methyl-2-[N-[4-(N-hydroxylamidino)phenyl] aminomethyl]benzimidazol-5-yl-carboxylic acid-N-(2-pyridyl)-N-[2-(methanesulfonylaminocarbonyl)ethyl]amide Prepared analogously to Example 96 from 1-methyl-2-[N-(4-cyanophenyl)aminomethyl]benzimidazol-5-yl-carboxylic acid-N-(2-pyridyl)-N-[2-(methanesulfonylaminocarbonyl)ethyl]amide and hydroxylamine. Yield: 27% of theory, $C_{26}H_{28}N_8O_5S$ (564.6); $R_f$ value: 0.75 (silica gel; dichloromethane/ethanol=7:3+1% glacial acetic acid); EKA mass spectrum: $(M+H)^+=565$; $(M+Na)^+=587$.

EXAMPLE 184

1-Methyl-2-[N-(5-amidinothiazol-2-yl-aminomethyl] benzimidazol-5-yl-carboxylic acid-N-(2-pyridyl)-N-(2-ethoxycarbonylethyl)amide hydrochloride Prepared analogously to Example 25d from 1-methyl-2-[N-(5-cyanothiazol-2-yl)aminomethyl]benzimidazol-5-yl-carboxylic acid-N-(2-pyridyl)-N-(2-ethoxycarbonylethyl) amide and ethanolic hydrochloric acid, ethanol, and ammonium carbonate.

EXAMPLE 185

1-Methyl-2-[N-(5-amidinothiazol-2-yl)aminomethyl] benzimidazol-5-yl-carboxylic acid-N-(2-pyridyl)-N-(2-hydroxycarbonylethyl)amide Prepared analogously to Example 26 from 1-methyl-2-[N-(5-amidinothiazol-2-yl)aminomethyl]benzimidazol-5-yl-carboxylic acid-N-(2-pyridyl)-N-(2-ethoxycarbonylethyl)amide hydrochloride and sodium hydroxide solution.

EXAMPLE 186

1-Methyl-2-[N-(2-amidinopyrazin-5-yl) aminomethyl]benzimidazol-5-yl-carboxylic acid-N-(2-pyridyl)-N-(2-ethoxycarbonylethyl)amide hydrochloride Prepared analogously to Example 25d from 1-methyl-2-[N-(2-cyanopyrazin-5-yl)aminomethyl]benzimidazol-5-yl-carboxylic acid-N-(2-pyridyl)-N-(2-ethoxycarbonylethyl) amide and ethanolic hydrochloric acid, ethanol, and ammonium carbonate. Yield: 19% of theory, $C_{25}H_{27}N_9O_3$ (501.6); $R_f$ value: 0.28 (silica gel; dichloromethane/methanol=4:1+1% glacial acetic acid); EKA mass spectrum: $(M+H)^+=502$; $(M+H+Na)^+=262.5$.

EXAMPLE 187

1-Methyl-2-[N-(2-amidinopyrazin-5-yl) aminomethyl]benzimidazol-5-yl-carboxylic acid-N-(2-pyridyl)-N-(2-hydroxycarbonylethyl)amide Prepared analogously to Example 26 from 1-methyl-2-[N-(2-amidinopyrazin-5-yl)aminomethyl]benzimidazol-5-yl-carboxylic acid-N-(2-pyridyl)-N-(2-ethoxycarbonylethyl)amide hydrochloride and sodium hydroxide solution. Yield: 11% of theory, $C_{23}H_{23}N_9O_3$ (473.5); $R_f$ value: 0.55 (Reversed Phase silica gel RP-8; 5% saline solution/methanol=6:4); EKA mass spectrum: $(M+H)^+=474$; $(M+H+Na)^+=496.6$.

EXAMPLE 188

1-Methyl-2-[2-[4-(N-n-hexyloxycarbonylamidino) phenyl]ethyl]benzimidazol-5-yl-carboxylic acid-N-phenyl-N-[2-(1H-tetrazol-5-yl)ethyl]amide Prepared analogously to Example 90 from 1-methyl-2-[2-(4-amidinophenyl)ethyl]benzimidazol-5-yl-carboxylic acid-N-phenyl-N-[2-(1H-tetrazol-5-yl)ethyl]amide and n-hexyl chloroformate.

EXAMPLE 189

1-Methyl-2-[N-(2-methoxy-4-n-pentoxycarbonylamidinophenyl)aminomethyl] benzimidazol-5-yl-carboxylic acid-N-phenyl-N-(2-ethoxycarbonylethyl)amide Prepared analogously to Example 90 from 1-methyl-2-[N-(4-amidino-2-methoxyphenyl)aminomethyl] benzimidazol-5-yl-carboxylic acid-N-phenyl-N-(2-ethoxycarbonylethyl)amide hydrochloride and n-pentyl chloroformate. Yield: 53% of theory, $C_{35}H_{42}N_6O_6$ (642.7); $R_f$ value: 0.54 (silica gel; dichloromethane/ethanol=9:1); EKA mass spectrum: $(M+H)^+=643$; $(M+H+Na)^{++}=333.4$.

EXAMPLE 190

1-Methyl-2-[N-(4-n-heptyloxycarbonylamidino-2-methoxyphenyl)aminomethyl]benzimidazol-5-yl-carboxylic acid-N-phenyl-N-(2-ethoxycarbonylethyl)amide Prepared analogously to Example 90 from 1-methyl-2-[N-(4-amidino-2-methoxyphenyl)aminomethyl] benzimidazol-5-yl-carboxylic acid-N-phenyl-N-(2-ethoxycarbonylethyl)amide hydrochloride and n-heptyl chloroformate. Yield: 68% of theory, $C_{37}H_{46}N_6O_6$ (670.8); $R_f$ value: 0.56 (silica gel; dichloromethane/ethanol=9:1); EKA mass spectrum: $(M+H)^+=671$; $(M+H+Na)^{++}=347.4$.

EXAMPLE 191

1-Methyl-2-[N-(4-ethoxycarbonylamidino-2-methoxyphenyl)aminomethyl]benzimidazol-5-yl-carboxylic acid-N-(2-pyridyl)-N-(2-ethoxycarbonylethyl)amide Prepared analogously to Example 90 from 1-methyl-2-[N-(4-amidino-2-methoxyphenyl)aminomethyl] benzimidazol-5-yl-carboxylic acid-N-(2-pyridyl)-N-(2-ethoxycarbonylethyl)amide hydrochloride and ethyl chloroformate. Yield: 43% of theory, $C_{31}H_{35}N_7O_6$ (601.7); $R_f$ value: 0.44 (silica gel; dichloromethane/ethanol=9:1); EKA mass spectrum: $(M+H)+=602$; $(M+H+Na)^{++}=312.8$.

EXAMPLE 192

1-Methyl-2-[N-(2-methoxy-4-n-pentoxycarbonylamidinophenyl)aminomethyl] benzimidazol-5-yl-carboxylic acid-N-(2-pyridyl)-N-(2-ethoxycarbonylethyl)amide Prepared analogously to Example 90 from 1-methyl-2-[N-(4-amidino-2-methoxyphenyl)aminomethyl] benzimidazol-5-yl-carboxylic acid-N-(2-pyridyl)-N-(2-ethoxycarbonylethyl)amide hydrochloride and n-pentyl chloroformate. Yield: 72% of theory, $C_{34}H_{41}N_7O_6$ (643.7); $R_f$ value: 0.49 (silica gel; dichloromethane/ethanol=9:1); EKA mass spectrum: $(M+H)^+=644$; $(M+H+Na)^{++}=333.9$.

EXAMPLE 193

1-Methyl-2-[N-(2-methoxy-4-n-heptyloxycarbonylamidinophenyl)aminomethyl] benzimidazol-5-yl-carboxylic acid-N-(2-pyridyl)-N-(2-ethoxycarbonylethyl)amide Prepared analogously to Example 90 from 1-methyl-2-[N-(4-amidino-2-methoxyphenyl)aminomethyl] benzimidazol-5-yl-carboxylic acid-N-(2-pyridyl)-N-(2-ethoxycarbonylethyl)amide hydrochloride and n-heptyl chloroformate. Yield: 55% of theory, $C_{36}H_{45}N_7O_6$ (671.8); $R_f$ value: 0.54 (silica gel; dichloromethane/ethanol=9:1); EKA mass spectrum: $(M+H)^+=672$; $(M+H+Na)^{++}=347.9$.

EXAMPLE 194

Dry Ampoule Containing 75 mg of Active Substance per 10 mL

| Composition: | |
|---|---|
| Active substance | 75.0 mg |
| Mannitol | 50.0 mg |
| water for injections | ad 10.0 mL |

Preparation:

Active substance and mannitol are dissolved in water. After packaging, the solution is freeze-dried. To produce the solution ready for use, the product is dissolved in water for injections.

EXAMPLE 195

Dry Ampoule Containing 35 mg of Active Substance per 2 mL

| Composition: | |
|---|---|
| Active substance | 35.0 mg |
| Mannitol | 100.0 mg |
| water for injections | ad 2.0 mL |

Preparation:

Active substance and mannitol are dissolved in water. After packaging, the solution is freeze-dried. To produce the solution ready for use, the product is dissolved in water for injections.

EXAMPLE 196

Tablet Containing 50 mg of Active Substance

| Composition: | |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2), and (3) are mixed together and granulated with an aqueous solution of (4). (5) is added to the dried granulated material. From this mixture, tablets are pressed, biplanar, faceted on both sides, and with a dividing notch on one side. Diameter of the tablets: 9 mm.

EXAMPLE 197
Tablet Containing 350 mg of Active Substance

| Preparation: | |
|---|---|
| (1) Active substance | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Preparation:

(1), (2), and (3) are mixed together and granulated with an aqueous solution of (4). (5) is added to the dried granulated material. From this mixture tablets are pressed, biplanar, faceted on both sides, and with a dividing notch on one side. Diameter of the tablets: 12 mm.

EXAMPLE 198
Capsules Containing 50 mg of Active Substance

| Composition: | |
|---|---|
| (1) Active substance | 50.0 mg |
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing. This powder mixture is packed into size 3 hard gelatin capsules in a capsule filling machine.

EXAMPLE 199
Capsules Containing 350 mg of Active Substance

| Composition: | |
|---|---|
| (1) Active substance | 350.0 mg |
| (2) Dried maize starch | 46.0 mg |
| (3) Powdered lactose | 30.0 mg |
| (4) Magnesium stearate | 4.0 mg |
| | 430.0 mg |

Preparation:

(1) is triturated with (3). This trituration is added to the mixture of (2) and (4) with vigorous mixing. This powder mixture is packed into size 0 hard gelatin capsules in a capsule filling machine.

EXAMPLE 200
Suppositories Containing 100 mg of Active Substance

| 1 suppository contains: | |
|---|---|
| Active substance | 100.0 mg |
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

What is claimed is:

1. A compound of the formula I:

$$R_a\text{—}A\text{—}Het\text{—}B\text{—}Ar\text{—}E \qquad (I)$$

wherein:

A is a carbonyl or sulfonyl group linked to the pyridino moiety of the group Het;

B is an ethylene group, wherein a methylene group linked to the group Ar, is optionally replaced by an oxygen or sulfur atom or by an —$NR_1$— group, wherein $R_1$ is a hydrogen atom or a methyl group;

E is an $R_b$NH—C(=NH)— group, wherein
$R_b$ is a hydrogen atom or a hydroxy, $C_{1-9}$-alkoxycarbonyl, cyclohexyloxycarbonyl, benzyloxycarbonyl, benzoyl, p-$C_{1-3}$-alkylbenzoyl or nicotinoyl group, wherein the ethoxy moiety in the 2-position of the abovementioned $C_{1-9}$-alkoxycarbonyl group is unsubstituted or additionally substituted by a $C_{1-3}$-alkylsulfonyl or 2-($C_{1-3}$-alkoxy)-ethyl group, Ar is a 1,4-phenylene group optionally substituted by a chlorine atom or by a methyl, ethyl, or methoxy group, or is a 2,5-thienylene group;

Het is a 3-methyl-2,6-imidazo[4,5-b]pyridinylene group; and $R_a$ is a $C_{1-6}$-alkyl group, a $C_{3-7}$-cycloalkyl group optionally substituted by a $C_{1-3}$-alkyl group, wherein the $C_{1-3}$-alkyl group may additionally be substituted by a carboxyl, $C_{1-6}$-alkoxycarbonyl, cyclohexyloxcarbonyl, or phenyl-$C_{1-3}$-alkoxycarbonyl group, or $R_a$ is a $R_2NR_3$— group, wherein
$R_2$ is a $C_{1-4}$-alkyl group optionally substituted by a carboxy, $C_{1-6}$-alkyloxycarbonyl, benzyloxycarbonyl, methylsulfonylaminocarbonyl, or 1H-tetrazol-5-yl group,
a $C_{2-4}$-alkyl group substituted at a carbon which is other than the one at the α-position relative to the adjacent nitrogen atom, by a hydroxy, benzyloxy, carboxy-$C_{1-3}$-alkyl-amino, $C_{1-3}$-alkoxycarbonyl-$C_{1-3}$-alkylamino, N—($C_{1-3}$-alkyl)-carboxy-$C_{1-3}$-alkylamino, or N—($C_{1-3}$-alkyl)-$C_{1-3}$-alkoxycarbonyl-$C_{1-3}$-alkylamino group, and $R_3$ is a propargyl group, wherein the unsaturated moiety is not linked directly to the nitrogen atom of the $R_2NR_3$— group, is a phenyl group optionally substituted by a fluorine or chlorine atom, or by a methyl or methoxy group, or is a pyridinyl group, and or a tautomer or salt thereof.

2. The compound of the formula I according to claim 1, wherein $R_a$ is a $R_2NR_3$— group, wherein:
$R_2$ is a $C_{1-4}$-alkyl group optionally substituted by a carboxy, $C_{1-6}$-alkyloxycarbonyl, benzyloxycarbonyl, methylsulfonylaminocarbonyl or 1H-tetrazol-5-yl group,
a $C_{2-4}$-alkyl group substituted at a carbon which is other than the one at the α-position relative to the adjacent nitrogen atom, by a hydroxy, benzyloxy, carboxy-$C_{1-3}$-alkyl-amino, $C_{1-3}$-alkoxycarbonyl-$C_{1-3}$-alkylamino, N—($C_{1-3}$-alkyl)-carboxy-$C_{1-3}$-alkylamino, or N—($C_{1-3}$-alkyl)-$C_{1-3}$-alkoxycarbonyl-$C_{1-3}$-alkylamino group, and $R_3$ is a propargyl group, wherein the unsaturated moiety is not linked directly to the nitrogen atom of the $R_2NR_3$— group, is a phenyl group optionally substituted by a fluorine or chlorine atom, or by a methyl or methoxy group, or is a pyridinyl group, and or a tautomer or salt thereof.

3. The compound of the formula I according to claim 1, wherein $R_3$ is a phenyl group optionally substituted by a fluorine or chlorine atom, or by a methyl or methoxy group, or is a pyridinyl group, or a tautomer or salt thereof.

4. The compound of the formula I according to claim 1, wherein $R_3$ is a propargyl group, wherein the unsaturated moiety is not linked directly to the nitrogen atom of the $R_2NR_3$— group, or a tautomer or salt thereof.

5. The compound of the formula I according to claim 1, wherein $R_3$ is a phenyl group optionally substituted by a fluorine or chlorine atom, or by a methyl or methoxy group, or a tautomer or salt thereof.

6. The compound of the formula I according to claim 1, wherein $R_3$ is a pyridinyl group, or a tautomer or salt thereof.

7. The compound of the formula I according to claim 1, wherein A is a carbonyl group linked to the benzo moiety of the group Het, or a tautomer or salt thereof.

8. The compound of the formula I according to claim 1, wherein A is a sulfonyl group linked to the benzo moiety of the group Het, or a tautomer or salt thereof.

9. The compound of the formula I according to claim 1, wherein $R_b$ is a hydrogen atom, or a tautomer or salt thereof.

10. The compound of the formula I according to claim 1, wherein $R_b$ is a hydroxy, $C_{1-9}$-alkoxycarbonyl, cyclohexyloxycarbonyl, benzyloxycarbonyl, benzoyl, p-$C_{1-3}$-alkylbenzoyl or nicotinoyl group, wherein the ethoxy moiety in the 2-position of the abovementioned $C_{1-9}$-alkoxycarbonyl group is unsubstituted or additionally substituted by a $C_{1-3}$-alkylsulfonyl or 2-($C_{1-3}$-alkoxy)-ethyl group, or a tautomer or salt thereof.

11. 3-Methyl-2-[(4-amidinophenyl)thiomethyl]imidazo[4,5-b]pyridin-6-yl-carboxylic acid-N-phenyl-N-(2-ethoxycarbonylethyl)amide, or a tautomer or salt thereof.

12. 3-Methyl-2-[N-(4-amidinophenyl)aminomethyl]imidazo[4,5-b]-pyridin-6-yl-carboxylic acid-N-phenyl-N-(2-ethoxycarbonylethyl)amide, or a tautomer or salt thereof.

13. 3-Methyl-2-[(4-amidinophenyl)thiomethyl]imidazo[4,5-b]pyridin-6-yl-carboxylic acid-N-phenyl-N-(2-hydroxycarbonylethyl)amide, or a tautomer or salt thereof.

14. 3-Methyl-2-[N-(4-amidinophenyl)aminomethyl]imidazo[4,5-b]-pyridin-6-yl-carboxylic acid-N-phenyl-N-(2-hydroxycarbonylethyl)amide, or a tautomer or salt thereof.

15. A physiologically acceptable salt of a compound according to one of claims 1, 2, 3, 4, 5, 6, 7, 8, 9, 10, 11, 12, 13, or 14.

16. A pharmaceutical composition comprising a compound according to one of claims 1, 2, 3, 4, 5, 6, 7, 8, 9, 10, 11, 12, 13 or 14, or a tautomer or salt thereof and a pharmaceutically acceptable carrier or diluent.

17. A method for the prophylaxis or treatment of venous and arterial thrombotic disease which comprises administering an antithrombotic amount of a compound according one of claims 1, 2, 3, 4, 5, 6, 7, 8, 9, 10, 11, 12, 13 or 14, or a physiologically acceptable salt thereof.

18. The method of claim 17, wherein the thrombotic disease is selected from the group consisting of: deep leg vein thrombosis, reocclusion after a bypass operation or angioplasty (PT(C)A), occlusion in peripheral arterial disease, pulmonary embolism, disseminated intravascular coagulation, coronary thrombosis, stroke, and the occlusion of a shunt or stent.

19. A method for providing antithrombotic support in thrombolytic treatment utilizing rt-PA or streptokinase, which comprises administering a therapeutically effective amount of a compound according one of claims 1, 2, 3, 4, 5, 6, 7, 8, 9, 10, 11, 12, 13 or 14, or a physiologically acceptable salt thereof.

20. A method for preventing metastasis or the growth of clot-dependent tumors, which comprises administering a therapeutically effective amount of a compound according one of claims 1, 2, 3, 4, 5, 6, 7, 8, 9, 10, 11, 12, 13 or 14, or a physiologically acceptable salt thereof.

21. A method for treating or preventing fibrin-dependent inflammatory processes, which comprises administering a therapeutically effective amount of a compound according one of claims 1, 2, 3, 4, 5, 6, 7, 8, 9, 10, 11, 12, 13 or 14, or a physiologically acceptable salt thereof.

* * * * *